US006825350B2

(12) United States Patent
Crooks et al.

(10) Patent No.: US 6,825,350 B2
(45) Date of Patent: Nov. 30, 2004

(54) SULFONAMIDE AND SULFAMIDE SUBSTITUTED IMIDAZOQUINOLINES AND METHODS FOR THE TREATMENT OF PERIODONTAL DISEASE USING THESE AND OTHER IMMUNE RESPONSE MODIFIERS

(75) Inventors: Stephen L. Crooks, Mathomedi, MN (US); Byron A. Merrill, River Falls, WI (US)

(73) Assignee: 3M Innovative Properties Company, St. Paul, MN (US)

( * ) Notice: Subject to any disclaimer, the term of this patent is extended or adjusted under 35 U.S.C. 154(b) by 451 days.

(21) Appl. No.: 10/166,321

(22) Filed: Jun. 15, 2001

(65) Prior Publication Data

US 2003/0130299 A1 Jul. 10, 2003

Related U.S. Application Data

(63) Continuation-in-part of application No. 09/589,216, filed on Jun. 7, 2000, now Pat. No. 6,331,539.
(60) Provisional application No. 60/138,365, filed on Jun. 10, 1999.

(51) Int. Cl.[7] .................. C07D 471/04; A61K 31/4745; A61P 37/02
(52) U.S. Cl. ......................................... 546/82; 514/293
(58) Field of Search ............................. 546/82; 514/293

(56) References Cited

U.S. PATENT DOCUMENTS

| | | | |
|---|---|---|---|
| 3,314,941 A | 4/1967 | Littell et al. |
| 4,689,338 A | 8/1987 | Gerster |
| 4,698,348 A | 10/1987 | Gerster |
| 4,929,624 A | 5/1990 | Gerster et al. |
| 4,988,815 A | 1/1991 | Andre et al. |
| 5,037,986 A | 8/1991 | Gerster |
| 5,175,296 A | 12/1992 | Gerster |
| 5,238,944 A | 8/1993 | Wick et al. |
| 5,266,575 A | 11/1993 | Gerster et al. |
| 5,268,376 A | 12/1993 | Gester |
| 5,346,905 A | 9/1994 | Gerster |
| 5,352,784 A | 10/1994 | Nikolaides et al. |
| 5,367,076 A | 11/1994 | Gerster |
| 5,389,640 A | 2/1995 | Gerster et al. |
| 5,395,937 A | 3/1995 | Nikolaides et al. |
| 5,446,153 A | 8/1995 | Lindstrom et al. |
| 5,482,936 A | 1/1996 | Lindstrom |
| 5,494,916 A | 2/1996 | Lindstrom et al. |
| 5,500,228 A | 3/1996 | Lawter et al. |
| 5,525,612 A | 6/1996 | Gerster |
| 5,693,811 A | 12/1997 | Lindstrom |
| 5,741,908 A | 4/1998 | Gerster et al. |
| 5,750,134 A | 5/1998 | Scholz et al. |
| 5,756,747 A | 5/1998 | Gerster et al. |
| 5,780,045 A | 7/1998 | McQuinn et al. |
| 5,854,257 A | 12/1998 | Armitage et al. |
| 5,939,047 A | 8/1999 | Jernberg |
| 5,939,090 A | 8/1999 | Beaurline et al. |
| 6,039,969 A | 3/2000 | Tomai et al. |
| 6,069,149 A | 5/2000 | Nanba et al. |
| 6,083,505 A | 7/2000 | Miller et al. |
| 6,110,929 A | 8/2000 | Gerster et al. |
| 6,123,957 A | 9/2000 | Jernberg |
| 6,194,425 B1 | 2/2001 | Gerster et al. |
| 6,245,776 B1 | 6/2001 | Skwierczynski et al. |
| 6,331,539 B1 | 12/2001 | Crooks et al. |
| 6,376,669 B1 | 4/2002 | Rice et al. |
| 2002/0055517 A1 | 5/2002 | Smith |
| 2002/0058674 A1 | 5/2002 | Hedenstrom et al. |

FOREIGN PATENT DOCUMENTS

| | | |
|---|---|---|
| EP | 0 394 026 | 10/1990 |
| EP | 1 104 764 | 6/2001 |
| JP | 9-208584 | 8/1997 |
| JP | 9-255926 | 3/1999 |
| JP | 11-222432 | 8/1999 |
| JP | 2002-247884 | 9/2000 |
| WO | WO 00/19987 | 4/2000 |
| WO | WO 00/47719 | 8/2000 |
| WO | WO 00/76505 | 12/2000 |
| WO | WO 00/76518 | 12/2000 |
| WO | WO 01/74343 | 10/2001 |
| WO | WO 02/07725 | 1/2002 |
| WO | WO 02/36592 | 5/2002 |
| WO | WO 02/46188 | 6/2002 |
| WO | WO 02/46189 | 6/2002 |
| WO | WO 02/46190 | 6/2002 |
| WO | WO 02/46191 | 6/2002 |
| WO | WO 02/46192 | 6/2002 |
| WO | WO 02/46193 | 6/2002 |
| WO | WO 02/46194 | 6/2002 |
| WO | WO 02/46749 | 6/2002 |

OTHER PUBLICATIONS

Wozniak, et al, "The Animation of 3–nitro–1, 5–naphthyridines by Liquid Ammonia/Potassium Permanganate[1,2]. A New and Convenient Animation Method.", *Journal of the Royal Netherlands Chemical Society*, 102, pp 511–513, Dec. 12, 1983.

Brennan, et al, "Automated Bioassay of Interferons in Micro–test Plates", *Biotechniques*, Jun./Jul., 78, 1983.

Testerman, et al., "Cytokine Induction by the Immunomodulators Imiquimod and S–27609", *Journal of Leukocyte Biology*, vol. 58, pp. 365–372, Sep. 1995.

(List continued on next page.)

*Primary Examiner*—Evelyn Mei Huang
(74) *Attorney, Agent, or Firm*—Dean A. Ersfeld

(57) ABSTRACT

The disclosure provides methods for the treatment and prevention of periodontal disease. In preferred embodiments, the invention provides for local treatment of periodontal tissues with a pharmaceutical composition including an immune response modifier (IRM) selected from the group of immune response modifiers comprising imidazoquinoline amines, imidazopyridine amines, 6,7-fused cycloalkylimidazopyridine amines, imidazonaphthyridine amines, oxazoloquinoline amines, thiazoloquinoline amines and 1,2-bridged imidazoquinoline amines.

1 Claim, 4 Drawing Sheets

OTHER PUBLICATIONS

Bachman, et al, "Synthesis of Substituted Quinolylamines. Derivatives of 4–Amino–7–Chloroquinoline", *J. Org. Chem*, 15, pp 1278–1284 (1950).

Jain, et al, "Chemical and Pharmacological Investigations of Some ω–Substituted Alkylamino–3–aminopyridines", *J. Med. Chem.*, 11 pp 87–92 (1968).

Baranov, et al., *Chem. Abs.* 85, 94371, (1976).

Berényi, et al, "Ring Transformation of Condensed Dihydro–as–triazines", *J. Heterocyclic Chem.*, 18, pp 1537–1540 (1981).

Chollet, et al, "Development of a Topically Active Imiquimod Formulation", *Pharmaceutical Development and Technology*, 4(1), pp 35–43 (1999).

Loesche et al., "Treatment Paradigms in Periodontal Disease", *Compend.Contin.Educ Dental*, 18(3):221–6, 228–30 (1997).

Page et al., "Advances in the Pathogenesis of Periodontitis: Summary of Developments, Clinical Implications and Future Directions", *Periodontology 2000*, 14:216–248 (1997).

Mathur et al., "Cell–mediated Immune System Regulation in Periodontal Disease", *Critical Rev.Oral.Bio. Med.*, 8:76–89 (1997).

Seymour G. J. et al., "Celluar immunity and hypersensitivity as components of periodontal destruction,"*Oral Dis.*, 2(1):96–101 (1996).

Bartova et al., "TH1 and TH2 cytokine profile in patients with early onset periodontitis and their healthy siblings," *Mediators Inflamm.*, 9(2):115–20 (2000).

Assuma et al., "IL–1 and TNF antagonists inhibit the inflammatory response and bone loss in experimental periodontitis", *J. of Immunology*, 160:403–409 (1998).

Baker P.J., et al., "Oral infection with *Porphyromonas gingvalis* and induced alveolar bone loss in immnocompetant and severe combined immunodefecient mice,"*Arch. Oral Biol.*, 39(12):1035–40 (Dec. 1994).

Takeichi et al., "Cytokine profiles of T–lymphocytes from gingival tissues with pathological pocketing," *J. Dent. Res.*, 79(8):1548–55 (Aug. 2000).

Kornman, Kenneth S., "Host Modulation as a Therapeutic Strategy in the Treatment of Periodontal Disease", *Clinical Infectious Diseases*, 28:520–6 (1999).

SULFONAMIDE AND SULFAMIDE SUBSTITUTED IMIDAZOQUINOLINES AND METHODS FOR THE TREATMENT OF PERIODONTAL DISEASE USING THESE AND OTHER IMMUNE RESPONSE MODIFIERS

CROSS REFERENCE TO RELATED APPLICATIONS

This application is a continuation-in-part of U.S. application Ser. No. 09/589,216, filed Jun. 7, 2000, issued as U.S. Pat. No. 6,331,539 B1, which claims the benefit of U.S. Provisional Application No. 60/138,365, filed Jun. 10, 1999.

FIELD OF THE INVENTION

This invention relates to imidazoquinoline compounds that have sulfonamide or sulfamide substitution at the 1-position and to pharmaceutical compositions containing the compounds. A further aspect of this invention relates to the use of these compounds as immunomodulators, for inducing cytokine biosynthesis in animals and in the treatment of diseases including viral and neoplastic diseases.

The invention is directed to methods for the treatment or prevention of periodontal conditions. Specifically the invention includes the novel use of immune response modifier compounds to treat or prevent periodontal disease. Preferred immune response modifiers are selected from the group of immune response modifiers comprising imidazoquinoline amines, imidazopyridine amines, 6,7-fused cycloalkylimidazopyridine amines, imidazonaphthyridine amines, oxazoloquinoline amines, thiazoloquinoline amines and 1,2-bridged imidazoquinoline amines.

BACKGROUND OF THE INVENTION

The first reliable report on the 1H-imidazo[4,5-c]quinoline ring system, Backman et al., *J. Org. Chem.* 15, 1278–1284 (1950) describes the synthesis of 1-(6-methoxy-8-quinolinyl)-2-methyl-1H-imidazo[4,5-c]quinoline for possible use as an antimalarial agent. Subsequently, syntheses of various substituted 1H-imidazo[4,5-c]quinolines were reported. For example, Jain et al., *J. Med. Chem.* 11, pp. 87–92 (1968), synthesized the compound 1-[2-(4-piperidyl)ethyl]-1H-imidazo[4,5-c]quinoline as a possible anticonvulsant and cardiovascular agent. Also, Baranov et al., *Chem. Abs.* 85, 94362 (1976), have reported several 2-oxoimidazo[4,5-c]quinolines, and Berenyi et al., *J Heterocyclic Chem.* 18, 1537–1540 (1981), have reported certain 2-oxoimidazo[4,5-c]quinolines.

Certain 1H-imidazo[4,5-c]quinolin-4-amines and 1- and 2-substituted derivatives thereof were later found to be useful as antiviral agents, bronchodilators and immunomodulators. These are described in, inter alia, U.S. Pat. Nos. 4,689,338; 4,698,348; 4,929,624; 5,037,986; 5,268,376; 5,346,905; and 5,389,640, all of which are incorporated herein by reference.

There continues to be interest in the imidazoquinoline ring system, as seen for example in WO 98/30562, EP 894 797 and WO 00/09506. EP 894 797 discloses amide substituted imidazoquinoline compounds that are disclosed to be useful as immune response modifying compounds, while WO 00/09506 discloses imidazoquinoline compounds that contain a sulfonamide substituent wherein the sulfonamide nitrogen is part of a saturated heterocyclic ring. Despite these efforts, however, there is a continuing need for compounds that have the ability to modulate the immune response, by induction of cytokine biosynthesis or other mechanisms.

Periodontal disease or periodontitis is an inflammatory disease that results in the destruction of both the hard and soft tissues supporting the teeth and has recently been hypothesized as a risk factor for cardiovascular disease. Beck et al. "Dental Infections and atherosclerosis, "*American Heart Journal,* 13:S528–533 (1999). It is estimated that over 10 million people in the United States are currently being treated for the more serious forms of this disease, with approximately 8 billion dollars spent for treatment each year.

Clinically, periodontitis is an inflammation of the periodontium that results in inflammation of the gingiva and may result in resorption of alveolar bone and recession of the gingiva. Recession of the gingiva can lead to exposure of the periodontal ligament allowing microorganisms to invade and destroy the ligament.

Infection by a few essential species of bacteria is important in initiating the host inflammatory response that is responsible for the tissue destruction and ultimate loss of teeth. Zambon, J. J., "Periodontal Disease, Microbial Factors,"*Ann. Periodontol.,* 1:879–825 (1996). The major pathogens associated with the disease have been identified and include *Porphyromonas gingivalis, Bacteroides forsythus* and *Actinobacillus actinomycetemcomitans.* Although essential to the pathogenesis, bacteria alone are insufficient to cause the disease. Host factors such as hereditary predisposition and environmental factors such as smoking are believed to equally effect disease occurrence and severity of outcome.

Forms of periodontitis include early onset periodontitis (EOP), chronic adult periodontitis (AP), and refractory periodontitis (RP). Localized juvenile periodontitis is a form of EOP which occurs in otherwise seemingly healthy adolescents and is associated with infection by *A. actinomycetemcomitans.* "Chronic adult periodontitis" is commonly associated with the presence of *B. forsythus, P. gingivalis,* many gram-negative asaccharolytic rods, and oral spirochetes. It typically occurs in patients over 35 years of age. Clinically, it resembles acute necrotizing ulcerative gingivitis imposed on rapidly progressive periodontitis. Patients may lose 9 to 12 mm of gingival attachment in as little as six months.

Current treatment for periodontal disease is almost exclusively mechanical and surgical in nature most frequently including scaling and root planing to remove calculus deposits. However, the mechanical treatments do not affect the underlying cause of disease. Antibiotics have also been used as an adjunct therapy, Loesche et al, "Treatment paradigms in periodontal disease", *Compend. Contin. Educ Dental,* 18(3):221–6, 228–30 (1997). Unfortunately, results have been disappointing because the antibiotic may not eliminate the bacteria responsible for the inflammatory component, and patients are subject to re-infection.

Accordingly, there is a continuing need for new and effective treatment and preventive measures for periodontal disease. The present invention is directed to this need.

SUMMARY OF THE INVENTION

We have found a new class of compounds that are useful in inducing cytokine biosynthesis in animals. Accordingly, this invention provides compounds of Formula I:

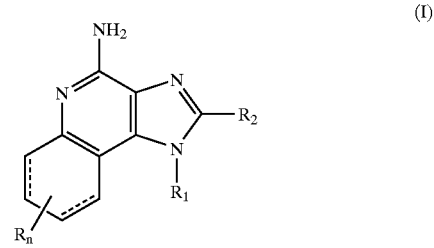

wherein R, $R_1$ and $R_2$ are as defined herein.

The compounds of Formula I are useful as immune response modifiers due to their ability to induce cytokine biosynthesis and otherwise modulate the immune response when administered to animals. This makes the compounds useful in the treatment of a variety of conditions such as viral diseases and tumors that are responsive to such changes in the immune response.

The invention further provides pharmaceutical compositions containing a therapeutically effective amount of a compound of Formula I and methods of inducing cytokine biosynthesis in an animal, treating a viral infection and/or treating a neoplastic disease in an animal by administering a effective amount of a compound of Formula I to the animal.

In addition, methods of synthesizing compounds of Formula I and intermediates useful in the synthesis of these compounds are provided.

The present invention provides methods for treating or preventing a periodontal condition comprising administering a therapeutically effective amount of an immune response modifier (IRM) compound directly to periodontal tissue in a patient affected by the periodontal condition. In preferred embodiments the IRM compound is selected from the group comprising imidazoquinoline amines, imidazopyridine amines, 6,7-fused cycloalkylimidazopyridine amines, imidazonaphthyridine amines, oxazoloquinoline amines, thiazoloquinoline amines and 1,2-bridged imidazoquinoline amines.

DETAILED DESCRIPTION

Figure 1:
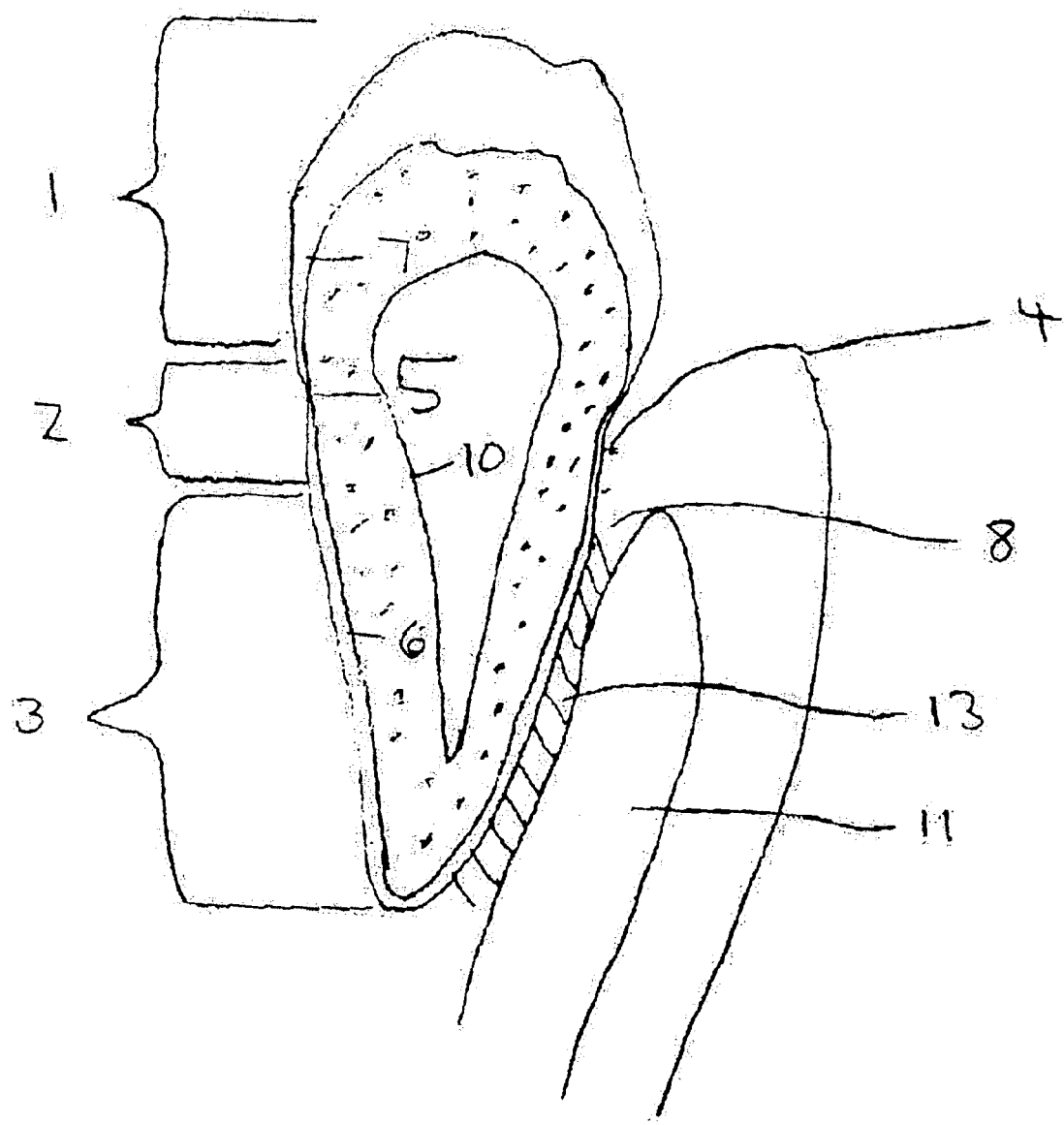
FIG. 1 is a diagram illustrating periodontal anatomy.

As mentioned earlier, the invention provides compounds of Formula I:

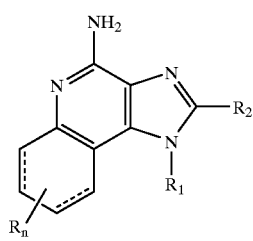

(I)

wherein
$R_1$ is -alkyl-$NR_3$—$SO_2$—X—$R_4$ or -alkenyl-$NR_3$—$SO_2$—X—$R_4$;
X is a bond or —$NR_5$—;
$R_4$ is aryl, heteroaryl, heterocyclyl, alkyl or alkenyl, each of which may be unsubstituted or substituted by one or more substituents selected from the group consisting of:
-alkyl;
-alkenyl;
-aryl;
-heteroaryl;
-heterocyclyl;
-substituted aryl;
-substituted heteroaryl;
-substituted heterocyclyl;
—O-alkyl;
—O-(alkyl)$_{0-1}$-aryl;
—O-(alkyl)$_{0-1}$-substituted aryl;
—O-(alkyl)$_{0-1}$-heteroaryl;
—O-(alkyl)$_{0-1}$-substituted heteroaryl;
—O-(alkyl)$_{0-1}$-heterocyclyl;
—O-(alkyl)$_{0-1}$-substituted heterocyclyl;
—COOH;
—CO—O-alkyl;
—CO-alkyl;
—S(O)$_{0-2}$-alkyl;
—S(O)$_{0-2}$-(alkyl)$_{0-1}$-substituted aryl;
—S(O)$_{0-2}$-(alkyl)$_{0-1}$-heteroaryl;
—S(O)$_{0-2}$-(alkyl)$_{0-1}$-substituted heteroaryl;
—S(O)$_{0-2}$(alkyl)$_{0-1}$-heterocyclyl;
—S(O)$_{0-2}$-(alkyl)$_{0-1}$-substituted heterocyclyl;
-(alkyl)$_{0-1}$-$NR_3R_3$;
-(alkyl)$_{0-1}$-$NR_3$—CO—O-alkyl;
-(alkyl)$_{0-1}$-$NR_3$—CO-alkyl;
-(alkyl)$_{0-1}$-$NR_3$—CO-aryl;
-(alkyl)$_{0-1}$-$NR_3$—CO-substituted aryl;
-(alkyl)$_{0-1}$-$NR_3$—CO-heteroaryl;
-(alkyl)$_{0-1}$-$NR_3$—CO-substituted heteroaryl;
—$N_3$;
-halogen;
-haloalkyl;
-haloalkoxy;
—CO-haloalkoxy;
—$NO_2$;
—CN;
—OH;
—SH; and in the case of alkyl, alkenyl, or heterocyclyl, oxo;

$R_2$ is selected from the group consisting of:
-hydrogen;
-alkyl;
-alkenyl;
-aryl;
-substituted aryl;
-heteroaryl;
-substituted heteroaryl;
-alkyl-O-alkyl;
-alkyl-O-alkenyl; and
-alkyl or alkenyl substituted by one or more substituents selected from the group consisting of:
—OH;
-halogen;
—N($R_3$)$_2$;
—CO—N($R_3$)$_2$;
—CO—C$_{1-10}$alkyl;
—CO—O—C$_{1-10}$ alkyl;
—$N_3$;
-aryl;
-substituted aryl;
-heteroaryl;
-substituted heteroaryl;
-heterocyclyl;
-substituted heterocyclyl;
—CO-aryl;

—CO-(substituted aryl);
—CO-heteroaryl; and
—CO-(substituted heteroaryl);

each $R_3$ is independently selected from the group consisting of hydrogen and $C_{1-10}$ alkyl;

$R_5$ is selected from the group consisting of hydrogen and $C_{1-10}$ alkyl, or $R_4$ and $R_5$ can combine to form a 3 to 7 membered heterocyclic or substituted heterocyclic ring;

n is 0 to 4 and each R present is independently selected from the group consisting of $C_{1-10}$ alkyl, $C_{1-10}$ alkoxy, halogen and trifluoromethyl, or a pharmaceutically acceptable salt thereof.

Preparation of the Compounds

Imidazoquinolines of the invention can be prepared according to Reaction Scheme I where R, $R_1$, $R_2$ and n are as defined above.

In step (1) of Reaction Scheme I a 4-chloro-3-nitroquinoline of Formula II is reacted with an amine of Formula $R_1NH_2$ where $R_1$ is as defined above to provide a 3-nitroquinolin-4-amine of Formula III. The reaction can be carried out by adding amine to a solution of a compound of Formula II in a suitable solvent such as chloroform or dichloromethane and optionally heating. Many quinolines of Formula II are known compounds (see for example, U.S. Pat. No. 4,689,338 and references cited therein).

In step (2) of Reaction Scheme I a 3-nitroquinolin-4-amine of Formula III is reduced to provide a quinoline-3,4-diamine of Formula IV. Preferably, the reduction is carried out using a conventional heterogeneous hydrogenation catalyst such as platinum on carbon or palladium on carbon. The reaction can conveniently be carried out on a Parr apparatus in a suitable solvent such as isopropyl alcohol or toluene.

In step (3) of Reaction Scheme I a quinoline-3,4-diamine of Formula IV is reacted with a carboxylic acid or an equivalent thereof to provide a 1H-imidazo[4,5-c]quinoline of Formula V. Suitable equivalents to carboxylic acid include acid halides, orthoesters, and 1,1-dialkoxyalkyl alkanoates. The carboxylic acid or equivalent is selected such that it will provide the desired $R_2$ substituent in a compound of Formula V. For example, triethyl orthoformate will provide a compound where $R_2$ is hydrogen and triethyl orthoacetate will provide a compound where $R_2$ is methyl. The reaction can be run in the absence of solvent or in an inert solvent such as toluene. The reaction is run with sufficient heating to drive off any alcohol or water formed as a byproduct of the reaction.

In step (4) of Reaction Scheme I a 1H-imidazo[4,5-c]quinoline of Formula V is oxidized to provide a 1H-imidazo[4,5-c]quinoline-5N-oxide of Formula VI using a conventional oxidizing agent that is capable of forming N-oxides. Preferred reaction conditions involve reacting a solution of a compound of Formula V in chloroform with 3-chloroperoxybenzoic acid at ambient conditions.

In step (5) of Reaction Scheme I a 1H-imidazo[4,5-c]quinoline-5N-oxide of Formula VI is aminated to provide a 1H-imidazo[4,5-c]quinolin-4-amine of Formula VII which is a subgenus of Formula I. Step (5) involves (i) reacting a compound of Formula VI with an acylating agent and then (ii) reacting the product with an aminating agent. Part (i) of step (5) involves reacting an N-oxide of Formula VI with an acylating agent. Suitable acylating agents include alkyl- or arylsulfonyl chlorides (e.g., benezenesulfonyl chloride, methanesulfonyl chloride, p-toluenesulfonyl chloride). Arylsulfonyl chlorides are preferred. Para-toluenesulfonyl chloride is most preferred. Part (ii) of step (5) involves reacting the product of part (i) with an excess of an animating agent. Suitable aminating agents include ammonia (e.g., in the form of animonium hydroxide) and ammonium salts (e.g., animonium carbonate, ammonium bicarbonate, ammonium phosphate). Ammonium hydroxide is preferred. The reaction is preferably carried out by dissolving the N-oxide of Formula VI in an inert solvent such as dichloromethane, adding the aminating agent to the solution, and then slowly adding the acylating agent. The product or a pharmaceutically acceptable salt thereof can be isolated using conventional methods.

Alternatively, step (5) maybe carried out by (i) reacting an N-oxide of Formula VI with an isocyanate and then (ii) hydrolyzing the resulting product. Part (i) involves reacting the N-oxide with an isocyanate wherein the isocyanato group is bonded to a carbonyl group. Preferred isocyanates include trichloroacetyl isocyanate and aroyl isocyanates such as benzoyl isocyanate. The reaction of the isocyanate with the N-oxide is carried out under substantially anhydrous conditions by adding the isocyanate to a solution of the N-oxide in an inert solvent such as chloroform or dichloromethane. Part (ii) involves hydrolysis of the product from part (i). The hydrolysis can be carried out by conventional methods such as heating in the presence of water or a lower alkanol optionally in the presence of a catalyst such as an alkali metal hydroxide or lower alkoxide.

Reaction Scheme I

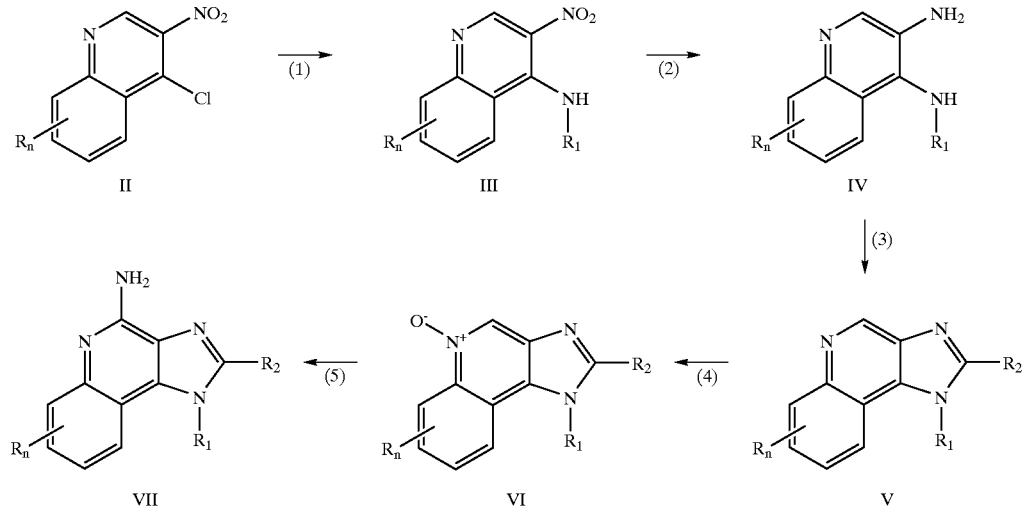

Compounds of the invention where the $R_1$ substituent contains a sulfonamide can also be prepared according to Reaction Scheme II where R, $R_2$, $R_4$ and n are as defined above and m is 1–20.

In Reaction Scheme II an aminoalkyl substituted 1H-imidazo[4,5-c]quinolin-4-amine of Formula VIII is reacted with a sulfonyl chloride of Formula IX to provide a compound of Formula X which is a subgenus of Formula I. The reaction can be run at ambient temperature in an inert solvent such as dichloromethane in the presence of a base such as pyridine or N,N-diisopropylethylamine. Many 1H-imidazo[4,5-c]quinolin-4-amines of Formula VIII are known compounds, see for example U.S. Pat. No. 6,069,149 (Namba); others can be readily prepared using known synthetic methods. Many sulfonyl chlorides of Formula IX are commercially available; others can be readily prepared using known synthetic methods. The product or a pharmaceutically acceptable salt thereof can be isolated using conventional methods.

Reaction Scheme II

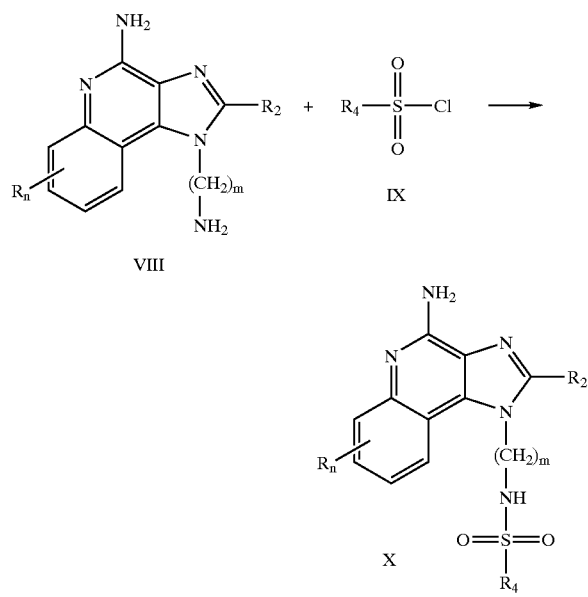

Compounds of the invention where the $R_1$ substituent contains a sulfonamide can also be prepared according to Reaction Scheme III where R, $R_2$, $R_4$ and n are as defined above and m is 1–20.

In Reaction Scheme III an aminoalkyl substituted 1H-imidazo[4,5-c]quinolin-4-amine of Formula VIII is reacted with a sulfonic anhydride of Formula XI to provide a compound of Formula X which is a subgenus of Formula I. The reaction can be run at ambient temperature in an inert solvent such as dichloromethane in the presence of a base such as pyridine or N,N-diisopropylethylamine. Alternatively, the reaction can be run at ambient temperature in acetonitrile. Many sulfonic anhydrides of Formula XI are commercially available; others can be readily prepared using known synthetic methods. The product or a pharmaceutically acceptable salt thereof can be isolated using conventional methods.

Reaction Scheme III

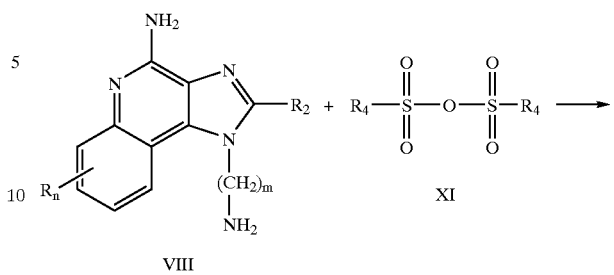

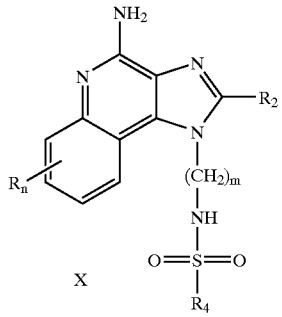

Tertiary sulfonamides of the invention can be prepared according to Reaction Scheme IV where R, $R_2$, $R_3$, $R_4$ and n are as defined above and m is 1–20.

In Reaction Scheme IV a 1H-imidazo[4,5-c]quinolinyl sulfonamide of Formula X is reacted with a halide of Formula XII to provide a compound of Formula XIII which is a subgenus of Formula I. The reaction can be carried out at ambient temperature by adding sodium hydride to a solution of a compound of Formula X in N,N-dimethylformamide and then adding the halide. Many halides of Formula XII are commercially available; others can be readily prepared using known synthetic methods. The product or a pharmaceutically acceptable salt thereof can be isolated using conventional methods.

Reaction Scheme IV

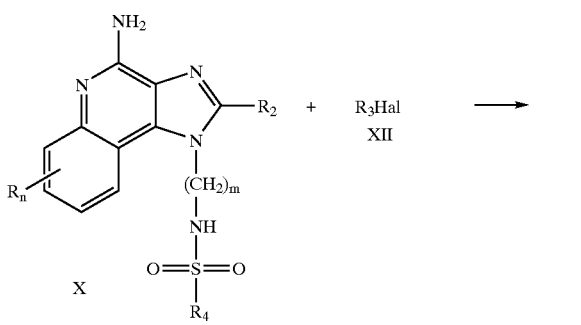

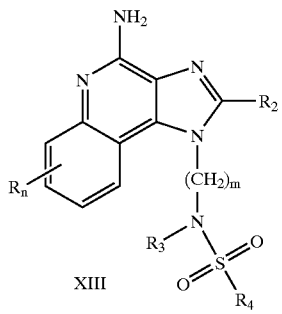

Compounds of the invention where $R_1$ contains a sulfamide group can be prepared according to Reaction Scheme V wherein R, $R_2$, $R_4$, $R_5$ and n are as defined above and m is 1–20.

In step (1) of Reaction Scheme V an aminoalkyl substituted 1H-imidazo[4,5-c]quinolin-4-amine of Formula VIII is reacted with sulfuryl chloride to generate in situ a sulfamoyl chloride of Formula XIV. The reaction can be carried out by adding a solution of sulfuryl chloride in dichloromethane to a solution of a compound of Formula VIII in dichloromethane in the presence of one equivalent of 4-(dimethylamino)pyridine. The reaction is preferably carried out at a reduced temperature (−78° C.). Optionally, after the addition is complete the reaction mixture can be allowed to warm to ambient temperature.

In step (2) of Reaction Scheme V an amine of Formula $R_5R_4NH$ is reacted with the sulfamoyl chloride of Formula XLV to provide a 1H-imidazo[4,5-c]quinolinyl sulfamide of Formula XV which is a subgenus of Formula I. The reaction can be carried out by adding a solution containing 2 equivalents of the amine and 2 equivalents of triethylamine in dichloromethane to the reaction mixture from step (1). The addition is preferably carried out at a reduced temperature (−78° C.). After the addition is complete the reaction mixture can be allowed to warm to ambient temperature. The product or a pharmaceutically acceptable salt thereof can be isolated using conventional methods.

Reaction Scheme V

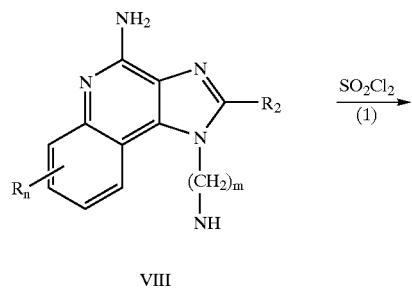

VIII

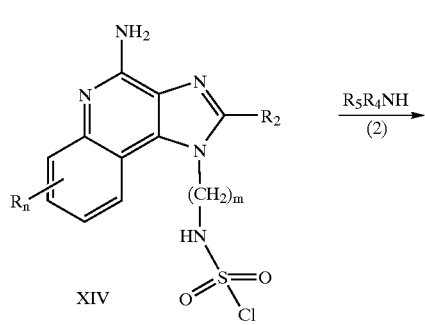

XIV

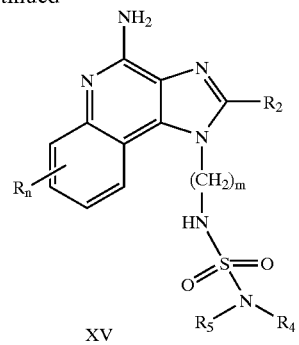

XV

Tetrahydroimidazoquinolines of the invention can be prepared according to Reaction Scheme VI where $R_2$, $R_3$, $R_4$, and $R_5$ are as defined above and m is 1–20.

In step (1) of Reaction Scheme VI an aminoalkyl substituted 1H-imidazo[4,5-c]quinolin-4-amine of Formula XVI is reduced to provide an aminoalkyl substituted 6,7,8,9-tetrahydro-1H-imidazo[4,5-c]quinolin-4-amine of Formula XVII. Preferably the reduction is carried out by suspending or dissolving the compound of Formula XVI in trifluoroacetic acid, adding a catalytic amount of platinum (IV) oxide, and then subjecting the mixture to hydrogen pressure. The reaction can conveniently be carried out on a Parr apparatus. The product or a salt thereof can be isolated using conventional methods.

In step (2a) of Reaction Scheme VI an aminoalkyl substituted 6,7,8,9-tetrahydro-1H-imidazo[4,5-c]quinolin-4-amine of Formula XVII is reacted to provide a compound of Formula XVIII which is a subgenus of Formula I. When $R_3$ is hydrogen, the reaction can be carried out in one step according to the methods described in Reaction Schemes II and III above using a tetrahydroimidazoquinoline of Formula XVII in place of the imidazoquinoline of Formula VIII. When $R_3$ is other than hydrogen, the reaction can be carried out in two steps with step one being carried out according to the methods of Reaction Schemes II and III and step two being carried out according to the method of Reaction IV using the tetrahydroimidazoquinoline analog of the imidazoquinoline. The product or a pharmaceutically acceptable salt thereof can be isolated using conventional methods.

In step (2b) of Reaction Scheme VI an aminoalkyl substituted 6,7,8,9-tetrahydro-1H-imidazo[4,5-c]quinolin-4-amine of Formula XVII is reacted to provide a compound of Formula XIX which is a subgenus of Formula I. The reaction can be carried out according to the method described in Reaction Scheme V using a tetrahydroimidazoquinoline of Formula XVII in place of the imidazoquinoline of Formula VIII. The product or a pharmaceutically acceptable salt thereof can be isolated using conventional methods.

Reaction Scheme VI

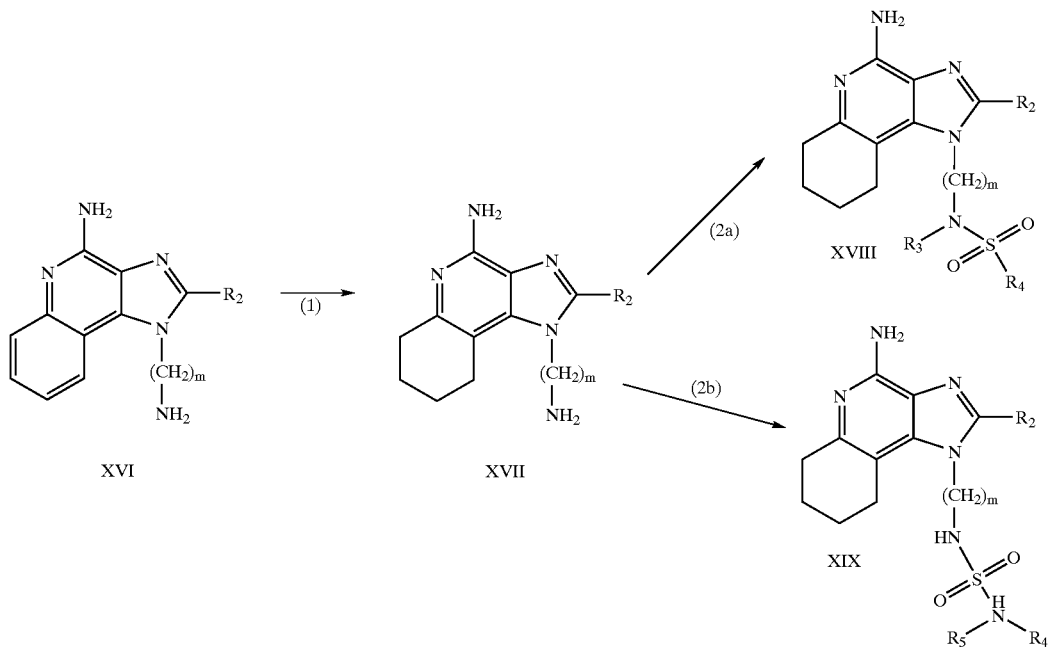

Tetrahydroimidazoquinolines of the invention can also be prepared according to Reaction Scheme VII where R, $R_2$, $R_3$, $R_4$, $R_5$ and n are as defined above and m is 1–20.

In step (1) of Reaction Scheme VII a 6,7,8,9-tetrahydro-1H-imidazo[14,5-c]quinolinyl tert-butylcarbamate of Formula XX is hydrolyzed to provide an aminoalkyl substituted 6,7,8,9-tetrahydro-1H-imidazo[4,5-c]quinolin-4-amine of Formula XXI. The reaction can be carried out dissolving the compound of Formula XX in a mixture of trifluoroacetic acid and acetonitrile and stirring at ambient temperature. Alternatively, the compound of Formula XX can be combined with dilute hydrochloric acid and heated on a steam bath. Tetrahydro-1H-imidazo[4,5-c]quinolinyl tert-butylcarbamates of Formula XX can be prepared using the synthetic route disclosed in U.S. Pat. No. 5,352,784 (Nikolaides). The product or a salt thereof can be isolated using conventional methods.

Steps (2a) and (2b) can be carried out in the same manner as in Reaction Scheme VI.

Reaction Scheme VII

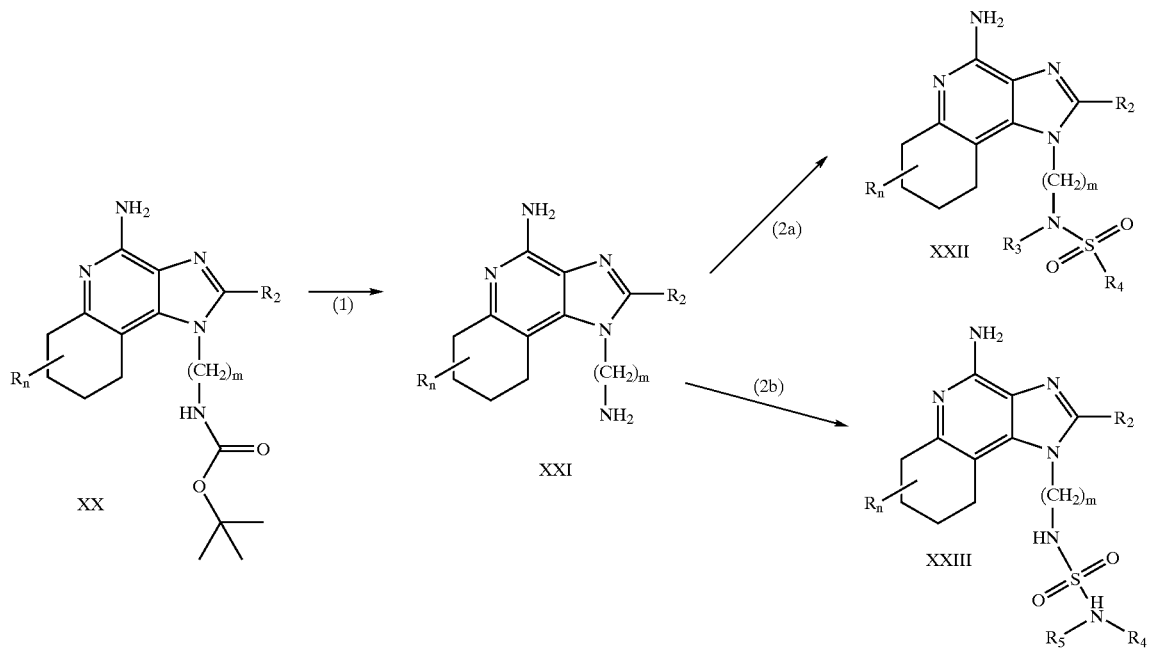

Some compounds of Formula I can be readily prepared from other compounds of Formula I. For example, compounds wherein the $R_4$ substituent contains a chloroalkyl group can be reacted with an amine to provide an $R_4$ substituent substituted by a secondary or teriary amino group; compounds wherein the $R_4$ substituent contains a nitro group can be reduced to provide a compound wherein the $R_4$ substituent contains a primary amine.

As used herein, the terms "alkyl", "alkenyl", "alkynyl" and the prefix "-alk" are inclusive of both straight chain and branched chain groups and of cyclic groups, i.e. cycloalkyl and cycloalkenyl. Unless otherwise specified, these groups contain from 1 to 20 carbon atoms, with alkenyl and alkynyl groups containing from 2 to 20 carbon atoms. Preferred groups have a total of up to 10 carbon atoms. Cyclic groups can be monocyclic or polycyclic and preferably have from 3 to 10 ring carbon atoms. Exemplary cyclic groups include cyclopropyl, cyclopentyl, cyclohexyl and adamantyl.

The term "haloalkyl" is inclusive of groups that are substituted by one or more halogen atoms, including groups wherein all of the available hydrogen atoms are replaced by halogen atoms. This is also true of groups that include the prefix "haloalk-". Examples of suitable haloalkyl groups are chloromethyl, trifluoromethyl, and the like.

The term "aryl" as used herein includes carbocyclic aromatic rings or ring systems. Examples of aryl groups include phenyl, naphthyl, biphenyl, fluorenyl and indenyl. The term "heteroaryl" includes aromatic rings or ring systems that contain at least one ring hetero atom (e.g., O, S, N). Suitable heteroaryl groups include furyl, thienyl, pyridyl, quinolinyl, tetrazolyl, imidazo, pyrazolo, thiazolo, oxazolo, and the like.

"Heterocyclyl" includes non-aromatic rings or ring systems that contain at least one ring hetero atom (e.g., O, S, N). Exemplary heterocyclic groups include pyrrolidinyl, tetrahydrofuranyl, morpholinyl, thiomorpholinyl, piperidinyl, piperazinyl, thiazolidinyl, imidazolidinyl, and the like.

Unless otherwise specified, the terms "substituted cycloalkyl", "substituted aryl", "substituted heteroaryl" and "substituted heterocyclyl" indicate that the rings or ring systems in question are further substituted by one or more substituents independently selected from the group consisting of alkyl, alkoxy, alkylthio, hydroxy, halogen, haloalkyl, haloalkylcarbonyl, haloalkoxy (e.g., trifluoromethoxy), nitro, alkylcarbonyl, alkenylcarbonyl, arylcarbonyl, heteroarylcarbonyl, aryl, arylalkyl, heteroaryl, heteroarylalkyl, heterocyclyl, heterocycloalkyl, nitric, alkoxycarbonyl, alkanoyloxy, alkanoylthio, and in the case of cycloalkyl and heterocyclyl, oxo.

In structural formulas representing compounds of the invention certain bonds are represented by dashed lines. These lines mean that the bonds represented by the dashed line can be present or absent. Accordingly, compounds of Formula I can be either imidazoquinoline compounds or tetrahydroimidazoquinoline compounds.

The invention is inclusive of the compounds described herein in any of their pharmaceutically acceptable forms, including isomers such as diastereomers and enantiomers, salts, solvates, polymorphs, and the like.

Pharmaceutical Compositions and Biological Activity

Pharmaceutical compositions of the invention contain a therapeutically effective amount of a compound of Formula I in combination with a pharmaceutically acceptable carrier.

As used herein, the term "a therapeutically effective amount" means an amount of the compound sufficient to induce a therapeutic effect, such as cytokine induction, antitumor activity and/or antiviral activity. Although the exact amount of active compound used in a pharmaceutical composition of the invention will vary according to factors known to those of skill in the art, such as the physical and chemical nature of the compound as well as the nature of the carrier and the intended dosing regimen, it is anticipated that the compositions of the invention will contain sufficient active ingredient to provide a dose of about 100 ng/kg to about 50 mg/kg, preferably about 10 µg/kg to about 5 mg/kg of the compound to the subject. Any of the conventional dosage forms maybe used, such as tablets, lozenges, parenteral formulations, syrups, creams, ointments, aerosol formulations, transdermal patches, transmucosal patches and the like.

The compounds of the invention have been shown to induce the production of certain cytokines in experiments performed according to the tests set forth below. These results indicate that the compounds are useful as immune response modifiers that can modulate the immune response in a number of different ways, rendering them useful in the treatment of a variety of disorders.

Cytokines that may be induced by the administration of compounds according to the invention generally include interferon-α (IFN-α) and tumor necrosis factor-α (TNF-α) as well as certain interleukins (IL). Cytokines whose biosynthesis may be induced by compounds of the invention include IFN-α, TNF-α, IL-1, 6, 10 and 12, and a variety of other cytokines. Among other effects, cytokines inhibit virus production and tumor cell growth, making the compounds useful in the treatment of viral diseases and tumors.

In addition to the ability to induce the production of cytokines, the compounds of the invention affect other aspects of the innate immune response. For example, natural killer cell activity may be stimulated, an effect that may be due to cytokine induction. The compounds may also activate macrophages, which in turn stimulates secretion of nitric oxide and the production of additional cytokines. Further, the compounds may cause proliferation and differentiation of B-lymphocytes.

Compounds of the invention also have an effect on the acquired immune response. For example, although there is not believed to be any direct effect on T cells or direct induction of T cell cytokines, the production of the T helper type 1 (Th1) cytokine IFN-γ is induced indirectly and the production of the T helper type 2 (Th2) cytokines IL-4, IL-5 and IL-13 are inhibited upon administration of the compounds. This activity means that the compounds are useful in the treatment of diseases where upregulation of the TH1 response and/or downregulation of the Th2 response is desired. In view of the ability of compounds of Formula Ia to inhibit the Th2 immune response, the compounds are expected to be useful in the treatment of atopic diseases, e.g., atopic dermatitis, asthma, allergy, and allergic rhinitis; and systemic lupus erythematosis; as a vaccine adjuvant for cell mediated immunity; and possibly as a treatment for recurrent fungal diseases and chlamydia.

The immune response modifying effects of the compounds make them useful in the treatment of a wide variety of conditions. Because of their ability to induce the production of cytokines such as IFN-α and/or TNF-α, the compounds are particularly useful in the treatment of viral diseases and tumors. This immunomodulating activity suggests that compounds of the invention are useful in treating diseases such as, but not limited to, viral diseases including genital warts; common warts; plantar warts; Hepatitis B; Hepatitis C; Herpes Simplex Virus Type I and Type II; molluscum contagiosum; HIV; CMV; VZV; intraepithelial neoplasias such as cervical intraepithelial neoplasia; human papillomavirus (HPV) and associated neoplasias; fungal diseases, e.g. candida, aspergillus, and cryptococcal meningitis; neoplastic diseases, e.g., basal cell carcinoma, hairy cell leukemia, Kaposi's sarcoma, renal cell carcinoma, squamous cell carcinoma, myelogenous leukemia, multiple myeloma, melanoma, non-Hodgkin's lymphoma, cutaneous T-cell lymphoma, and other cancers; parasitic diseases, e.g. pneumocystis carnii, cryptosporidiosis, histoplasmosis, toxoplasmosis, trypanosome infection, leishmaniasis; and bacterial infections, e.g., tuberculosis, mycobacterium avium. Additional diseases or conditions that can be treated using the compounds of the invention include eczema; eosinophilia; essential thrombocythaemia leprosy; multiple sclerosis; Ommen's syndrome; discoid lupus; Bowen's disease; Bowenoid papulosis; and to enhance or stimulate the healing of wounds, including chronic wounds.

Accordingly, the invention provides a method of inducing cytokine biosynthesis in an animal comprising administering an effective amount of a compound of Formula I to the animal. An amount of a compound effective to induce cytokine biosynthesis is an amount sufficient to cause one or more cell types, such as monocytes, macrophages, dendritic cells and B-cells to produce an amount of one or more cytokines such as, for example, IFN-α, TNF-α, IL-1,6,10 and 12 that is increased over the background level of such cytokines. The precise amount will vary according to factors known in the art but is expected to be a dose of about 100 ng/kg to about 50 mg/kg, preferably about 10 μg/kg to about 5 mg/kg. The invention also provides a method of treating a viral infection in an animal, and a method of treating a neoplastic disease in an animal, comprising administering an effective amount of a compound of Formula I to the animal. An amount effective to treat or inhibit a viral infection is an amount that will cause a reduction in one or more of the manifestations of viral infection, such as viral lesions, viral load, rate of virus production, and mortality as compared to untreated control animals. The precise amount will vary according to factors known in the art but is expected to be a dose of 100 ng/kg to about 50 mg/kg, preferably about 10 μg/kg to about 5 mg/kg. An amount of a compound effective to treat a neoplastic condition is an amount that will cause a reduction in tumor size or in the number of tumor foci. Again, the precise amount will vary according to factors known in the art but is expected to be a dose of about 100 ng/kg to about 50 mg/kg, preferably about 100 μg/kg to about 5 mg/kg.

The present disclosure provides methods for treatment or prevention of an oral condition, such as periodontal disease, using an immune response modifier (IRM) compound. As used herein, "immune response modifier compound", means a compound which induces the production of one or more cytokines, e.g., Interferon (α), Tumor Necrosis Factor, and Interleukin-12, from hematopoietec cells including dendritic cells and/or monocyte/macrophages. Examples of such compounds include the CpG oligonucleotides, lipopolysaccharides, polyinosic:polycytidylic acid complexes, and polypeptides and proteins known to induce cytokine production from dendritic cells and/or monocyte/macrophages.

In preferred embodiments, the IRM compound is selected from the group comprising imidazoquinoline amines, imidazopyridine amines, 6,7-fused cycloalkylimidazopyridine amines, imidazonaphthyridine amines, oxazoloquinoline amines, thiazoloquinoline amines and 1,2-bridged imidazoquinoline amines. Methods for preparing such IRMs and pharmaceutical compositions containing them are disclosed in, for example, U.S. Pat. Nos. 4,689,338; 5,389,640; 5,268, 376; 4,929,624; 5,266,575; 5,352,784; 5,494,916; 5,482, 936; 5,346,905; 5,395,937; 5,238,944; 5,525,612; 5,175, 296; 5,693,811; 5,741,908; 5,939,090; 6,110,929; 4,988, 815; 5,376,076; and PCT Publications WO 99/29693; WO 00/76505; WO 00/76518; and WO 00/76519. The entire disclosure of each of these patents and patent applications is incorporated herein by reference.

As used herein, "periodontitis" is an inflammation or degeneration, or both, of the dental periodontium, alveolar bone, cementum, and adjacent gingival tissue. Referring to FIG. 1, by way of review, each tooth consists of three parts, a crown 1, neck 2 and root 3. The crown 1 is the part of the tooth that projects above the gingiva 4 and occludes with one or more other teeth in the opposite jaw. The neck 2 is the part of the tooth between the crown 1 and the root 3. The cemento-enamel junction (CEJ) 5 is the location where the cementum 6 of the root 3 and enamel 7 of the crown 1 meet. The root 3 is fixed in the tooth socket 8, or "alveolus". Most of the tooth is composed of dentin 10 that is covered by enamel 7 over the crown 1 and cementum 6 over the root 3. The cementum 6 over the root 3 is attached to the alveolar bone 11 by periodontal ligament 13 to form a fibrous joint between the tooth and its alveolus 8.

Thus, as used herein, "periodontal tissues" are the tissues surrounding and supporting a tooth and include the periodontal ligament, alveolar bone and gingiva. A "periodontal pocket" is a pathologically induced space extending below the cemento-enamel junction (CEJ) and resulting from break down of the alveolar bone and/or periodontal ligament.

The inflammatory nature of periodontitis is not yet fully understood, although a general model has been advanced, Page et al., "Advances in the pathogenesis of periodontitis: summary of developments, clinical implications and future directions", *Periodontology* 2000, 14:216–248 (1997). One hypothesis is that the normal immune response against the initiating bacteria, which would prevent the bacteria from causing disease, has been altered and becomes not just ineffective but contributory to the disease process, Mathur et al., "Cell-mediated immune system regulation in periodontal disease,"*Critical Rev. Oral. Bio. Med.,* 8:76–89 (1997). According to this hypothesis, in patients with minimal or no periodontal disease, the immune response is skewed towards a TH1 immune response, which is generally involved with controlling viruses and tumors. In patients with progressive periodontal disease, the immune response pathway is skewed towards a TH2 response, characterized by activation of B cells to secrete antibodies. It is believed that the antibody response is ineffective against the bacteria, is usually of short duration, and does not lead to immune "memory". In addition, cytokines that are secreted by TH2 cells can activate inappropriate host tissue remodeling enzymes that contribute to the destruction of the connective tissue that holds the teeth to the jaw, and enzymes that cause the resorption of the alveolar bone around the teeth.

Another report sets forth a model of periodontal disease based on the T-cell dichotomy characterized by a higher proportion of IL-4 producing cells in periodontitis tissues, and hypothesize a role for TH2 cells in progressive lesions of the disease, Seymour G. J. et al., "Cellular immunity and hypersensitivity as components of periodontal destruction, "*Oral Dis.,* 2(1):96–101 (1996) This report has been recently supported by work by Bartova et al., "TH1 and TH2 cytokine profile in patients with early onset periodontitis and their healthy siblings,"*Mediators Inflamm.*, 9(2):115–20 (2000).

A different hypothesis that has been advanced is that the TH1 response, which activates a number of typical cytokines, can result in bone resorption as a result of osteoclast activation. Assuma et al., "IL-1 and TNF antagonists inhibit the inflammatory response and bone loss in experimental periodontitis", *J. of Immunology*, 160:403–409 (1998).

In another report, a cumulative cytokine profile has been observed in periodontitis consistent with the predominance of TH1-type cells in pathological tissues and with TH2-type cells, when present, being up-regulated under appropriate stimulation. Takeichi et al., "Cytokine profiles of T-lymphocytes from gingival tissues with pathological pocketing,"*J. Dent. Res.*, 79(8):1548–55 (August 2000). Both CD4 and CD8+lymphocytes were shown to express TH1- and TH2-type cytokine messages.

The foregoing reports emphasize the relative lack of agreement on the mechanisms responsible for periodontal disease pathogenesis, and the lack of consensus for any medicinal approach to disease management.

Many imidazoquinoline amine, imidazopyridine amine, 6,7-fused cycloalkylimidazopyridine amine, imidazonaphthyridine amines, oxazoloquinoline amines, thiazoloquinoline amines and 1,2-bridged imidazoquinoline amine compounds have demonstrated potent immunomodulating, antiviral and antitumor (including anticancer) activity, and have also been shown to be useful as vaccine adjuvants to enhance protective immune system response to vaccines. Recently, it has been found that many of these IRM compounds can inhibit TH2 immune responses, as well as enhance TH1 immune responses. See, eg., U.S. Pat. No. 6,039,969, the entire disclosure of which is incorporated herein by reference.

Although the immunology of periodontal disease remains controversial the inventors have discovered that treatment with immune response modifying compounds may benefit patients with periodontitis and treat the underlying infection. Specifically, treatment with IRM compounds can reduce the destruction of the alveolar bone or periodontal ligament. If treatment is administered at an appropriate time before destruction of periodontal tissue begins, the invention can also be used to modulate the patient's immune response to effectively prevent clinical signs of periodontal disease. Thus the IRM compositions can have both therapeutic and prophylactic value.

A "patient" includes humans and animals.

A pharmaceutical composition useful in the method of the invention includes an immune response modifier (IRM) compound. Preferred compositions include compounds selected from the group of immune response modifiers comprising imidazoquinoline amines, imidazopyridine amines, 6,7-fused cycloalkylimidazopyridine amines, imidazonaphthyridine amines, oxazoloquinoline amines, thiazoloquinoline amines and 1,2-bridged imidazoquinoline amines. Preferred compounds include 1-(2-methylpropyl)-1H-imidazo[4,5-c]quinolin-4-amine (imiquimod), 4-amino-2-ethoxymethyl-α, α-dimethyl-1H-imidazo[4,5-c] quinoline-1-ethanol (resiquimod), and 2-propyl[1,3]thiazolo [4,5-c]quinolin-4-amine.

The pharmaceutical compositions can be provided in a form suitable for systemic application or in a form suitable for local delivery to the affected site. The latter mode is presently preferred. The pharmaceutical compositions can be formulated to provide for delivery of the IRM compound to the treatment site at a predetermined rate for a predetermined duration, alone or in combination with other therapeutic or prophylactic agents. Examples of such additional agents include antibiotics, fluoride sources etc. Excipients commonly used to formulate drugs into a suitable vehicle can be incorporated as necessary provided that the excipient does not substantially interfere with the function or stability of the composition. Non-limiting examples of forms suitable for the pharmaceutical compositions include enhanced viscosity formulations such as disclosed in U.S. Pat. Nos. 5,939,047 and 6,123,957; transmucosal patches such as disclosed in U.S. Pat. Nos. 5,780,045 and 5,750,134 and PCT Publication WO 00/19987; microcapsules such as disclosed in U.S. Pat. No. 5,500,228; biodegradable cross-linked hydrolyzed gelatin matrices such as those used in the PerioChip™ (available from Perio Products Ltd., Jerusalem, Israel); dental rinses and dentifrices. Excipients such as flavorings, colorants, surfactants, binders can be employed as needed.

A "treatment site" means the site where the pharmaceutical composition is delivered to the patient. Treatment sites are typically local sites proximate to a lesion and generally include the gingival surfaces, periodontal pockets, or any other site from which the drug could be delivered to the maxillary or mandibular tissue. The composition is typically delivered topically or by placing the composition in the subgingival space (periodontal pocket).

As used herein, the term "therapeutically effective amount" means an amount of an IRM compound sufficient to prevent, reduce or reverse periodontal disease. The therapeutically effective amount of an IRM compound for periodontitis will vary depending on such things as the activity of the particular compound, the particular composition administered, the duration of delivery, the frequency of administration, the treatment site, and any other therapeutic agents being coadministered.

In general, a pharmaceutical composition useful for practicing the methods of the invention can contain from about 0.001% to 5.0% of an IRM compound based on the total weight of the pharmaceutical composition. Typically the composition will contain from about 0.01% to 1% of an IRM compound.

The IRM compound may be present in the pharmaceutical composition as the sole therapeutically active ingredient or in combination with other therapeutic agents such as antibiotics, e.g., penicillins, tetracycline; antiseptics, e.g., chlorhexidine; corticosteroids, e.g., hydrocortisone, betamethasone; and nonsteroidal antiinflammatories, e.g., flurbiprofen, ibuprofen, naproxen.

The frequency and duration of administration can vary as needed for prevention or treatment of the disease. Treatment regimens may include administration at least one time per week, typically two to three times per week, or even daily for at least one week, typically two weeks and in some cases three to four weeks. The patient can be rechecked according to the common standards of care. Thus recalls can be monthly, every two months and typically every three months. Repeated administration can be provided as needed.

Typically, the IRM compound can be applied to a treatment site in some type of sustained release formulation, such as gels, capsules, patches, biodegradable matrices, etc. for delivery of the IRM compound to the treatment site over a period of about 1–24 hours, typically about 1–8 hours, and in some embodiments, about 1–3 hours. It is also foreseen that in certain situations, a burst of IRM compound can be provided by direct administration, such as by subgingival placement, use of a dentifrice or mouth wash, etc. at the discretion of the clinician.

The following Examples are provided to further explain the invention through specific description of some embodiments of the invention. The Examples, however, are not intended to limit the scope of the invention.

EXAMPLE 1

N$^1$-[4-(4-Amino-2-butyl-1H-imidazo[4,5-c]quinolin-1-yl)butyl]-5-(dimethylamino)-1-naphthalenesulfonamide

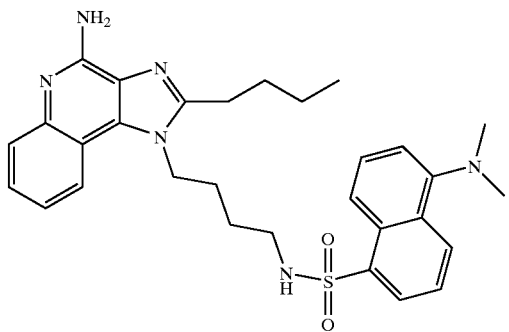

5-Dimethylamino-1-naphthalenesulfonyl chloride (1.82 g, 6.74 mmol) was added to a mixture of N,N-diisopropylethylamine (1.23 mL, 7.06 mmol), dichloromethane (15 mL) and 1-(4-aminobutyl)-2-butyl-1H-imidazo[4,5-c]quinolin-4-amine (2.0 g, 6.42 mmol). The reaction mixture was allowed to stir at ambient temperature overnight. Methanol was added to the reaction mixture until a clear solution was obtained. Silica gel was added to the reaction mixture and then the solvents were removed. The silica gel was placed in a column and then eluted with chloroform in a stepwise gradient to 9:1 chloroform:methanol. The resulting product was recrystallized from N,N-dimethylformamide and deionized water to provide 2.5 g of N$^1$-[4-(4-amino-2-butyl-1H-imidazo [4,5-c]quinolin-1-yl)butyl]-5-(dimethylamino)-1-naphthalenesulfonamide as a yellow crystalline solid, m.p. 223–224° C. Analysis: Calculated for $C_{30}H_{36}N_6O_2S$: % C, 66.15; % H, 6.66; % N, 15.43; Found: % C, 66.36; % H, 6.34; % N, 15.23.

EXAMPLE 2

N$^1$-[4-(4-Amino-1H-imidazo[4,5-c]quinolin-1-yl)butyl]-5-(dimethylamino)-1-naphthalenesulfonamide

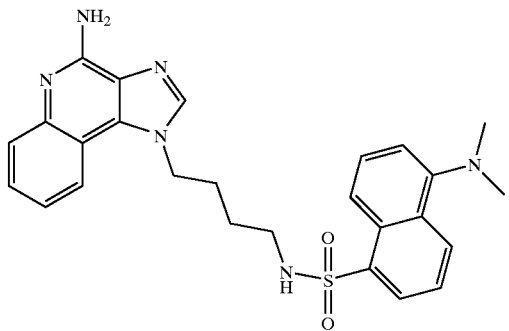

A suspension of 1-(4-aminobutyl)-1H-imidazo[4,5-c]quinolin-4-amine (0.5 g, 2.0 mmol) in pyridine (250 mL) was warmed to 60° C. to dissolve the amine. The solution was allowed to cool to about 30° C. and then 5-dimethylamino-1-naphthaleneslfonyl chloride (0.5 g, 1.8 mmol) was slowly added. After 1 hour 0.3 g of 5-dimethylamino-1-naphthalenesulfonyl chloride was added. The reaction mixture was warmed to 60° C. and maintained at that temperature overnight. The reaction mixture was concentrated under vacuum. The residue was recrystallized from propyl acetate to provide N$^1$-(4-(4-amino-1H-imidazo[4,5-c]quinolin-1-yl)butyl]-5-(dimethylamino)-1-naphthalenesulfonamide as a solid, m.p. 200–201° C.

EXAMPLE 3

N$^2$-[4-(4-Amino-2-butyl-1H-imidazo[4,5-c]quinolin-1-yl)butyl]-2-thiophenesulfonamide

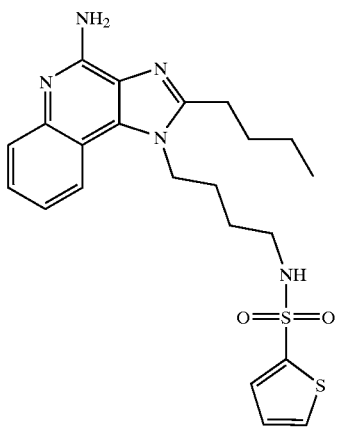

2-Thiophenesulfonyl chloride (0.3 g in 10 ml dichloromethane, 1.6 mmol) was added dropwise to a stirring solution of 1-(4-aminobutyl)-2-butyl-1H-imidazo[4,5-c]quinoline-4-amine (0.5 g, 1.6 mmol), dichloromethane (40 ml), and pyridine (0.8 ml). The reaction was maintained at room temperature for a few hours and then an additional portion of 2-thiophenesulfonyl chloride (0.1 g, 0.6 mmol) was added. The reaction was maintained overnight and then concentrated in vacua. The resulting residue was purified by flash column chromatography (silica gel, 9:1 dichloromethane/methanol) and the fractions containing product were washed with saturated aqueous sodium bicarbonate. The organic layer was dried (MgSO$_4$, filtered, and concentrated to provide 0.2 g of N$^2$-[4-(4-amino-2-butyl-1H-imidazo[4,5-c]quinolin-1-yl)butyl]-2-thiophenesulfonamide as an off white powder, m.p. 137.5–141.5° C. $^1$H NMR (300 MHz, DMSO-d$_6$) δ 8.00 (d, J=8.0 Hz, 1H), 7.89 (dd, J=5.0, 1.3 Hz, 1H), 7.83 (broad s, 1H), 7.61 (dd, J=8.3, 1.1 Hz, 1H), 7.54 (dd, J=3.7, 1.3 Hz, 1H), 7.42 (t, J=7.2 Hz, 1H), 7.25 (m, 1H), 7.15 (m, 1H), 6.44 (broad s, 2H), 4.47 (t, J=7.4 Hz, 2H), 2.87 (m, 4H), 1.80 (m, 4H), 1.58–1.38 (m, 4H), 0.96 (t, J=7.4 Hz, 3H); IR (KBr) 3467, 3361, 3167, 3091, 2957, 2933, 2870, 1644, 1617, 1585, 1533, 1478, 1405, 1336, 1154, 1095, 1014, 854, 761, 733 cm$^{-1}$; MS (EI)m/e 457.1606 (457.1606 calcd for $C_{22}H_{27}N_5O_2S_2$); Anal calcd for $C_{22}H_{27}N_5O_2S_2$: C, 57.74; H 5.95; N, 15.30. Found: C, 57.50; H, 5.98; N, 15.15.

EXAMPLE 4

N-[4-(4-Amino-2-butyl-1H-imidazo[4,5-c]quinolin-1-yl)butyl]phenylmethanesulfonainide

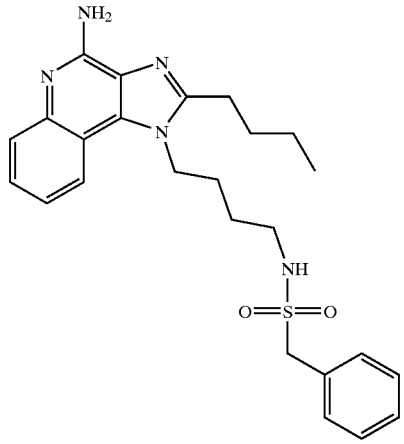

α-Toluenesulfonyl chloride (0.5 g in 10 ml dichloromethane, 2.7 mmol) was added dropwise to a stirring solution of 1-(4-aminobutyl)-2-butyl-1H-imidazo[4,5-c]quinoline-4-amine (0.75 g, 2.4 mmol), dichloromethane (115 ml), and pyridine (1 ml). The reaction was maintained at room temperature for 4 hours and then concentrated in vacuo. The residue was purified by flash column chromatography (silica gel, 9:1 dichloromethane/methanol, Rf 0.16). The fractions containing product were combined and washed with saturated aqueous bicarbonate. The organic layer was dried (MgSO4), filtered, and concentrated. A final recrystallization from dichloromethane/diethyl ether provided 0.65 g of N-[4-(4-amino-2-butyl-1H-imidazo[4,5-c]quinolin-1-yl)butyl]phenylmethanesulfonamide as a white crystalline solid, m.p. 197.0–199.5° C. $^1$H NMR (300 MHz, DMSO-$d_6$) δ 8.02 (d, J=7.6 Hz, 1H), 7.62 (dd, J=8.3, 1.1 Hz, 1H), 7.42 (dt, J=7.5, 1.1 Hz, 1H), 7.35–7.23 (m, 7H), 7.12 (t, J=5.4 Hz, 1H), 6.46 (broad s, 2H), 4.49 (t, J=7.5 Hz, 2H), 4.29 (s, 2H), 2.91 (m, 4H), 1.83–1.42 (m, 8H), 0.96 (t, J=7.4 Hz, 3H); IR (KBr) 3460, 3293, 3226, 3158, 2955, 2931, 2867, 1632, 1586, 1534, 1482, 1437, 1389, 1331, 1152, 1094, 752, 700 cm$^{-1}$; MS (EI) m/e 465.2204 (465.2198 calcd for $C_{25}H_{31}N_5O_2S$); Anal calcd for $C_{25}H_{31}N_5O_2S$: C, 64.49; H, 6.71; N, 15.04. Found: C, 64.15; H, 6.71; N, 15.00.

EXAMPLE 5

$N^1$-[4-(4-Amino-2-butyl-1H-imidazo [4,5-c]quinolin-1-yl)butyl]-1-benzenesulfonamide

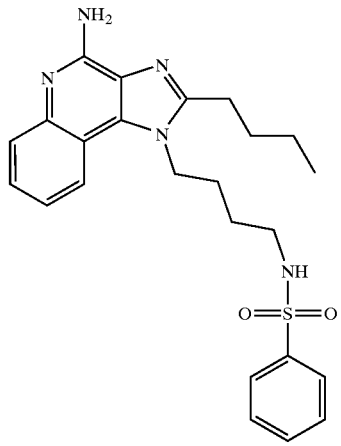

Benzenesulfonyl chloride (0.45 ml in 10 ml dichloromethane, 3.5 mmol) was added dropwise to a stirring solution of 1-(4-aminobutyl)-2-butyl-1H-imidazo[4,5-c]quinoline-4-amine (1.0 g, 3.2 mmol), dichloromethane (140 ml), and pyridine (0.8 ml). The reaction was maintained at room temperature for four hours and then concentrated in vacuo. The residue was purified by flash column chromatography (silica gel, 9:1 dichloromethane/methanol, $R_f$ 0.28) followed by recrystallization from dichloromethane/diethyl ether to provide 1.14 g of $N^1$-[4-(4-amino-2-butyl-1H -imidazo[4,5-c]quinolin-1-yl)butyl]-1-benzenesulfonamide as a white powder, m.p. 75.5–79.0° C. $^1$H NMR (500 MHz, DMSO-$d_6$) δ 7.99 (d, J=7.7 Hz, 1H), 7.76 (d, J=7.2, 2H), 7.63–7.53 (m, 5H), 7.42 (m, 1H), 7.25 (m, 1H), 6.43 (broad s, 2H), 4.45 (t, J=7.6 Hz, 2H), 2.87 (t, J=7.7 Hz, 2H), 2.78 (m, 2H), 1.79 (m, 4H), 1.55–1.40 (m, 4H), 0.95 (t, J=7.4 Hz, 3H); MS (EI) m/e 451.2036 (451.2042 calcd for $C_{21}H_{29}N_5O_2S$); Anal calcd for $C_{24}H_{29}N_5O_2S$ C, 63.83; H, 6.47; N, 15.51. Found: C, 63.89; H, 6.42; N, 15.30.

EXAMPLE 6

$N^1$-[4-(4-Amino-2-butyl-1H-imidazo[4,5-c]quinolin-1-yl)butyl]methanesulfonamide

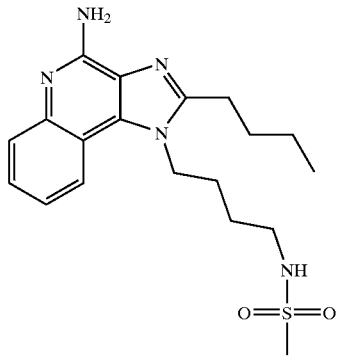

Methanesulfonic anhydride (0.6 g, 3.4 mmol) was added dropwise to a stirring solution of 1-(4-aminobutyl)-2-butyl-1H-imidazo[4,5-c]quinoline-4amine (1.0 g, 3.2 mmol) and acetonitrile (200 ml). A precipitate formed within a few minutes. The solvent was removed in vacuo and the residue was partitioned between dichioroinethane and saturated aqueous sodium bicarbonate. The fractions were separated and the organic fraction was dried (MgSO$_4$), filtered and concentrated to yield the crude product as a white solid. Recrystallization from methyl acetate provided N-[4-(4-amino-2-butyl-1H-imidazo[4,5-c]quinolin-1-yl)butyl] methanesulfonamide as a white crystalline solid, m.p. 195.1–196.0° C. $^1$H NMR (300 MHz, DMSO-$d_6$) δ 8.04 (d, J=7.4 Hz, 1H), 7.61 (dd, J=8.3, 1.2 Hz, 1H ), 7.50 (dt, J=7.5, 1.1 Hz, 1H ), 7.26 (dt, J=7.5, 1.2 Hz, 1H), 6.99 (t, J=5.7 Hz, 1H ), 6.44 (broad s, 2H ), 4.52 (t, J=7.5 Hz, 2H ), 3.02–2.86 (m, 7H) 1.82 (m, 4H), 1.62 (m, 2H ), 1.46 (q, J=7.4 Hz, 2H ), 0.96 (t, J=7.4 Hz, 3H); IR (KBr) 3348, 3299, 3152, 2952, 2931, 2869, 1642, 1584, 1530, 1480, 1323, 1155, 1142, 1094, 982, 765 cm$^{-1}$; MS (EI) m/e 389.1889 (389.1885 calcd for $C_{19}H_{27}N_5O_2S$); Anal calcd for $C_{19}H_{27}N_5O_2S$: C, 58.59; H, 6.99; N, 17.98. Found: C, 58.26; H, 6.64; N, 17.69

EXAMPLE 7

N[1]-[4-(4-Amino-2-butyl-1H-imidazo[4,5-c]quinolin-1-yl)butyl]-3-nitro-1-benzenesulfonamide Hydrochloride

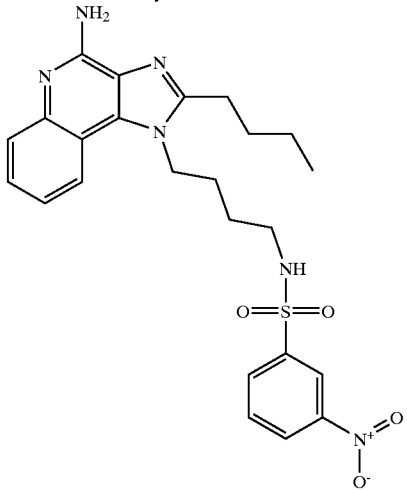

According to the general method of Example 5, 3-nitrobenzenesulfonyl chloride and 1-(4-aminobutyl)-2-butyl-1H-imidazo[4,5-c]quinoline-4-amine were combined. N[1]-[4-(4-Amino-2-butyl-1H-imidazo[4,5-c]quinolin-1-yl)butyl]-3-nitro-1-benzenesulfonamide was isolated as the hydrochloride salt (white solid), m.p. 176.0–178.2° C. $^1$H NMR (300 MHz, DMSO-$d_6$) δ 8.70 (very broad s, 2H), 8.49–8.42 (m, 2H), 8.21–8.17 (m, 2H), 8.06 (t, J=5.7 Hz, 1H), 7.88–7.81 (m, 2H), 7.71 (t, J=7.7 Hz, 1H), 7.57 (t, J=7.7 Hz, 1H), 4.56 (t, J=7.3 Hz, 2H), 2.94 (t, J=7.7 Hz, 2H), 2.86 (m, 2H) 1.81 (m, 4H), 1.60–1.42 (m, 4H), 0.96 (t, J=7.3 Hz, 3H); IR (KBr) 3096, 2954, 2869, 2771, 1671, 1607, 1528, 1351, 1335, 1163, 1128, 1083, 879, 758, 735, 672, 661 cm$^{-1}$; MS (EI) m/e 496.1897 (496.1893 calcd for $C_{24}H_{28}N_6O_4S$). Anal calcd for $C_{24}H_{28}N_6O_4S*HCl*H_2O$: C, 52.31; H, 5.67; N, 15.25. Found: C, 52.26; H, 5.46; N, 15.09.

EXAMPLE 8

N[1]-[4-(4-Amino-2-butyl-1H-imidazo[4,5-c]quinolin-1-yl)butyl]-3-amino-1-benzenesulfonamide Hydrochloride

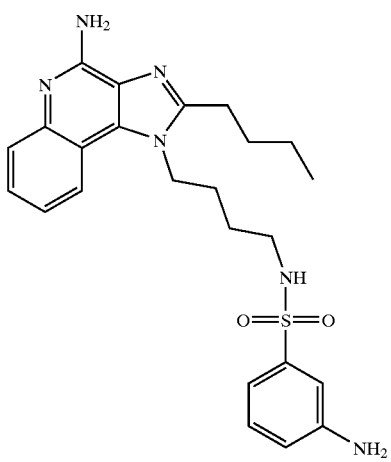

A solution N[1]-[4-(4-Amino-2-butyl-1H-imidazo[4,5-c]quinolin-1-yl)butyl]-3-nitro-1-benzenesulfonamide hydrochloride (0.4 g) in methanol (250 ml) was charged with a catalytic amount of 10% palladium on carbon (0.085 g). The reaction was placed under an atmosphere of hydrogen (50 psi; 3.44×10$^5$ Pa) and shaken on a Parr apparatus for 2 hours. The reaction mixture was filtered and the solvent removed in vacua. The solid product was recrystallized from 2-propanol to provide 0.18 g of N[1]-[4-(4-amino-2-butyl-1H-imidazo[4,5-c]quinolin-1-yl)butyl]-3-amino-1-benzenesulfonamide hydrochloride as an off white crystalline solid, m.p. 110.2° C. (decomposition). $^1$H NMR (300 MHz, DMSO-$d_6$) δ 8.70 (very broad s, 2H), 8.22 (d, J=8.2 Hz, 1H), 7.83 (d, J=7.8 Hz, 1H), 7.72 (t, J=7.6 Hz, 1H), 7.59 (t, J=7.7 Hz, 1H), 7.43 (t, J=5.9 Hz, 1H), 7.15 (t, J=7.9 Hz, 1H), 6.95 (t, J=1.9 Hz, 1H), 6.84 (d, J=7.7 Hz, 1H), 6.73 (dd, J=8.0, 1.5 Hz, 1H), 5.63 (broad s, 2H), 4.56 (t, J=7.5 Hz, 2H), 2.96 (t, J=7.7 Hz, 2H), 2.77 (q, J=6.3 Hz, 2H), 1.83 (m, 4H), 1.60–1.40 (m, 4H), 0.97 (t, J=7.3 Hz, 3H); IR (KBr) 3313, 3135, 2957, 2870, 2782, 1671, 1599, 1485, 1454, 1313, 1155, 1084, 754, 686 cm$^{-1}$; MS (EI) m/e 466.2150 (466.2151 calcd for $C_{24}H_{30}N_6O_2S$). Anal calcd for $C_{24}H_{30}N_6O_2S*HCl*0.25H_2O$: C, 56.79; H, 6.26; N, 16.56; Cl, 6.98. Found: C, 56.87; H, 6.22; N, 16.19; Cl, 7.22.

EXAMPLE 9

N[1]-[4-(4-Amino-2-butyl-1H-imidazo[4,5-c]quinolin-1-yl)butyl]-4-nitro-1-benzenesulfonamide Hydrochloride

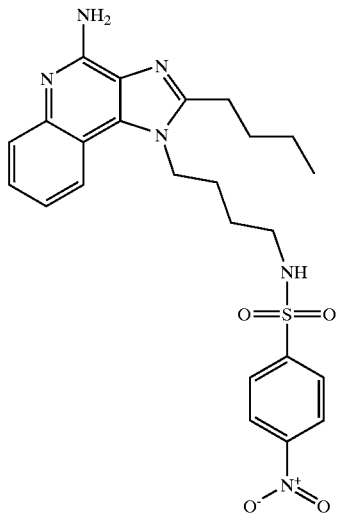

According to the general method of Example 5, 4-nitrobenzenesulfonyl chloride and 1-(4-aminobutyl)-2-butyl-1H-imidazo[4,5-c]quinoline-4-amine were combine. N[1]-[4-(4-Amino-2-butyl-1H-imidazo[4,5-c]quinolin-1-yl)butyl]-4-nitro-1-benzenesulfonamide was isolated as the hydrochloride salt (white solid), m.p. 96.0° C. (decomposition). $^1$H NMR (300 MHz, DMSO-$d_6$) δ 8.70 (very broad s, 2H), 8.38–8.34 (m, 2H), 8.19 (d, J=8.2 Hz, 1H), 8.09 (t, J=5.6 Hz, 1H), 8.03–7.99 (m, 2H), 7.80 (d, J=7.4 Hz, 1H), 7.68 (t, J=7.4 Hz, 1H), 7.54 (t, J=7.2 Hz, 1H), 4.55 (t, J=7.4 Hz, 2H), 2.94 (t, J=7.7 Hz, 2H), 2.86 (q, J=6.2 Hz, 2H), 1.80 (m, 4H), 1.58 (m, 2H), 1.45 (q, J=7.5 Hz, 2H), 0.96 (t, J=7.3 Hz, 3H); IR (KBr) 3283, 3100, 2957, 2870, 2782, 1670, 1606, 1528, 1347, 1311, 1162, 1092, 854, 746, 737, 686 cm$^{-1}$; MS (EI) m/e 496.1902 (496.1893 calcd for $C_{24}H_{28}N_6O_4S$). Anal calcd for $C_{24}H_{28}N_6O_4*HCl*0.85H_2O$: C, 52.57; H, 5.64; N, 15.33. Found: C, 52.57; H, 5.46; N, 15.33.

EXAMPLE 10

N¹-[4-(4-Amino-2-butyl-1H-imidazo[4,5-c]quinolin-1-yl)butyl]-4-amino-1-benzenesulfonamide Hydrochloride

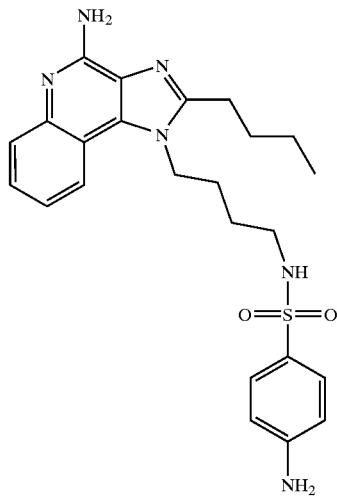

A solution of N¹-[4-(4-Amino-2-butyl-1H-imidazo[4,5-c]quinolin-1-yl)butyl]-4-nitro-1-benzenesulfonamide hydrochloride (0.38 g) in methanol (250 ml) was charged with a catalytic amount of 10% palladium on carbon (0.085 g). The reaction was placed under an atmosphere of hydrogen (50 psi; 3.44×10⁵ Pa)) and shaken on a Parr apparatus for 2 hours. The reaction mixture was filtered and the solvent removed in vacuo. The solid product was recrystallized from 2-propanol to provide 0.34 g of N¹-[4-(4-amino-2-butyl-1H-imidazo[4,5-c]quinolin-1-yl)butyl]-4amino-1-benzenesulfonamide hydrochloride as an off white powder, m.p. 203.1–205.0° C. ¹H NMR (300 MHz, DMSO-$d_6$) δ 8.65 (very broad s, 2H), 8.21(d, J=8.0 Hz, 1H), 7.82 (m, 1H), 7.71 (t, J=7.7 Hz, 1H), 7.58 (t, J=7.7 Hz, 1H), 7.38 (d, J=8.7 Hz, 2H), 7.13 (t, J=5.9 Hz, 1H), 6.60 (d, J=8.7 Hz, 2H), 5.92 (broad s, 2H), 4.55 (t, J=7.6 Hz, 2H), 2.96 (t, J=7.6 Hz, 2H), 2.70 (q, J=6.4 Hz, 2H), 1.81 (m, 4H), 1.58–1.43 (m, 4H), 0.96 (t, J=7.4 Hz, 3H); IR (KBr) 3430, 3316, 3215, 3046, 2955, 2868, 2679, 1671, 1594, 1334, 1157, 1091, 851, 776, 759 cm⁻¹; MS (EI) m/e 466.2145 (466.2151 calcd for $C_{24}H_{30}N_6O_2S$). Anal calcd for $C_{24}H_{30}N_6O_2S$*HCl: C, 57.30; H, 6.21; N, 16.71. Found: C, 57.36; H, 6.31; N, 16.21.

EXAMPLE 11

N⁵-[4-(4-Amino-2-butyl-1H-imidazo[4,5-c]quinolin-1-yl)butyl]-5-isoquinolinesulfonamide

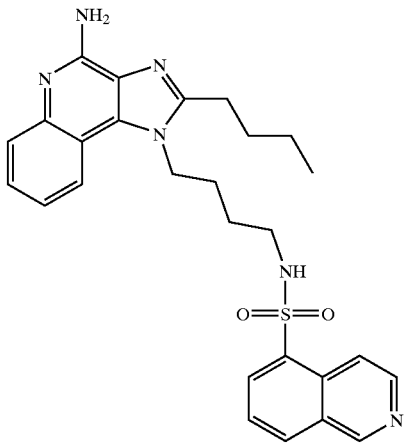

A suspension of isoquinoline-5-sulfonyl chloride hydrochloride (0.83 g in 50 ml of pyridine, 3.1 mmol) was added dropwise to a stirring solution of 1-(4-aminobutyl)-2-butyl-1H-imidazo[4,5-c]quinoline-4-amine (1.0 g, 3.2 mmol) and dichloromethane (175 ml). The solution turned a bright yellow color and was maintained at room temperature for 4 hours. An additional 0.18 g of isoquinoline-5-sulfonyl chloride hydrochloride was added and the reaction was maintained an additional 60 hours. The yellow solution was concentrated in vacuo, dissolved in dichloromethane, and washed sequentially with saturated aqueous sodium bicarbonate and water. The organic fraction was dried (MgSO₄), filtered, and concentrated in vacua. The residue was purified by flash column chromatography (silica gel, 9:1 dichloromethane/methanol) to provide 0.7 g of N⁵-[4-(4-amino-2-butyl-1H-imidazo[4,5-c]quinolin-1-yl)butyl]-5-isoquinolinesulfonamide as a white crystalline solid, m.p. 96.0° C. (decomposition). ¹H NMR (300 MHz, DMSO-$d_6$) δ 9.44 (d, J=0.7 Hz, 1H), 8.64(d, J=6.1 Hz, 1H), 8.41–8.35 (m, 2H), 8.30 (dd, J=7.4, 1.2 Hz, 1H), 8.11 (t, J=5.6 Hz, 1H), 7.92 (d, J=7.6 Hz, 1H), 7.75 (t, J=7.7 Hz, 1H ), 7.61 (dd, J=8.3, 1.2 Hz, 1H), 7.41 (dt, J=7.7, 1.2 Hz, 1H), 7.22 (dt, J=7.6, 1.2 Hz, 1H ), 6.47 (broad s, 2H ), 4.38 (t, J=7.5 Hz, 2H ), 2.86–2.74 (m, 4H), 1.78–1.63 (m, 4H), 1.50–1.34 (m, 4H), 0.94 (t, J=7.4 Hz, 3H); MS (EI) m/e 502.2151 (502.2151 calcd for $C_{27}H_{30}N_6O_2S$). Anal calcd for $C_{27}H_{30}N_6O_2S$: C, 64.52; H, 6.02; N, 16.72. Found: C, 64.03; H, 6.03; N, 16.55.

EXAMPLE 12

N-[4-(4-Amino-2-(4-methoxybenzyl)-1H-imidazo[4,5-c]quinolin-1-yl]butyl]methanesulfonamide

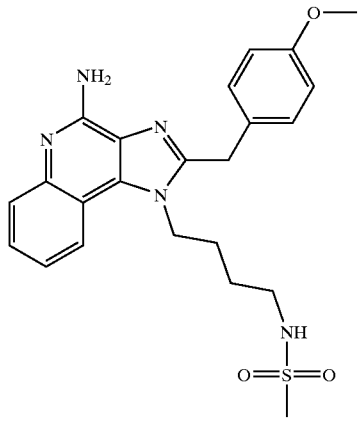

Methanesulfonic anhydride (0.19 g, 1.1 mmol) was added to a stirring solution of 1-(4-aminobutyl)-2-(4-methoxybenzyl)-1H-imidazo[4,5-c]quinolin-4-amine (0.4 g, 1.07 mmol), dichloromethane (75 ml) and acetonitrile (100 ml). The reaction was maintained at room temperature for 60 hours. The solvent was removed in vacuo and the residue was purified by flash column chromatography (silica gel, 9:1 dichloromethane\methanol). The fractions containing product were combined, washed with saturated aqueous sodium bicarbonate, dried (MgSO₄), filtered, and concentrated to provide 0.3 g of N-[4-(4-amino-2-(4-methoxybenzyl)-1H-imidazo[4,5-c]quinolin-1-yl]butyl]methanesulfonamide as a white solid, m.p. 78.1–79.5° C. ¹H NMR (300 MHz, DMSO-$d_6$) δ 7.99 (d, J=7.6 Hz, 1H), 7.62 (dd, J=8.3. 1.2 Hz, 1H), 7.42 (m, 1H), 7.27–7.21 (m, 3H), 6.98 (t, J=5.7 Hz, 1H), 6.89 (d, J=8.7 Hz, 2H), 6.58 (broad s, 2H), 4.45 (broad s, 2H), 4.33 (s, 2H), 3.72 (s, 3H), 2.87 (m, 5H), 1.55 (broad s, 2H); MS (CI) m/e 454 (M+H).

EXAMPLE 13

N¹-[4-(4-Amino-1H-imidazo[4,5-c]quinolin-1-y)butyl]-1-butanesulfonamide

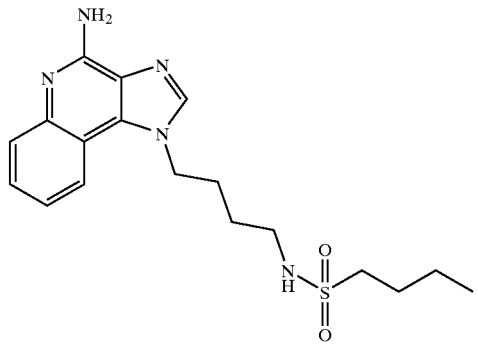

A solution of 1-(4-aminobutyl)-1H-imidazo[4,5-c]quinolin-4-amine (9.3 mg, 36 μmol) in 10 mL of dichloromethane in a screw-capped test tube was cooled down to −50° C. Butanesulfonyl chloride (45 μmol) was added as a 0.3 M solution in dichloromethane, with argon bubbling through the mixture during addition and for an additional 15 seconds. The mixture was allowed to stand at −50° C. overnight. Aminomethyl polystyrene resin (ca. 90 mg, 0.62 meq/g, 100–200 mesh, Bachem) was added and the mixture was warmed to reflux and shaken at about 600 rpm for 3 hours. The mixture was filtered through a Poly-Prep column (Bio-Rad #731–1550) to remove resin. Solvent was removed in vacua and the residue was purified by semi-preparative hplc on a Gilson system (Rainin Microsorb C18 column, 21.4×250 mm, 8 micron particle size, 60A pore, 10 mL/min., gradient elution from 2–95% B in 25 mm., hold at 95% B for 5 mm., where A=0.1% trifluoroacetic acid/water and B=0.1% trifluoroacetic acid/acetonitrile, peak detection at 254 nm for triggering fraction collection). The semi-prep hplc fractions were analyzed by LC-APCI/MS and the appropriate fractions were combined and lyophilized. The solid was dissolved in ca. 3 mL of 2:1 dichloromethane-methanol and shaken with ca. 80 mg (300 μmol) of diisopropylaminomethyl-polystyrene resin (Argonaut PS-DIEA, 3.86 mmol/g) for ~2 h to liberate the free amine, and then filtered and dried in vacua to give the product as a solid. MS (APCI) m/e 376.16 (M+H).

EXAMPLE 14

N¹-{4-[4-Amino-2-(2-methoxyethyl)-6,7,8,9-tetrahydro-1H-imidazo[4,5-c]quinolin-1-yl]butyl}-4-fluoro-1-benzenesulfonamide

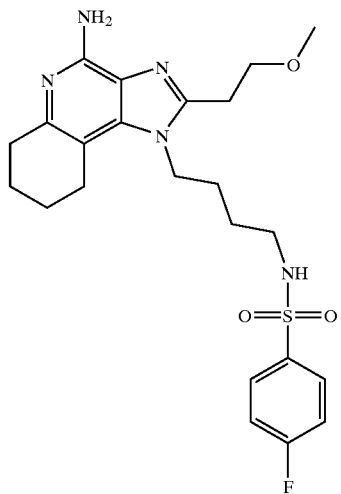

According to the general method of Example 5, 1-(4-aminobutyl)-2-(2-methoxyethyl)-6,7,8,9-tetrahydro-1H-imidazo[4,5-c]quinolin-4-amine and 4-fluorobenzenesulfonyl chloride were combined. Recrystallization from 4:1 n-propyl acetate\methanol provided N¹-{4-[4-amino-2-(2-methoxyethyl)-6,7,8,9-tetrahydro-1H-imidazo[4,5-c]quinolin-1-yl]butyl}-4-fluoro-1-benzenesulfonamide as a white crystalline solid, m.p. 191.0–193.0° C. ¹H NMR (300 MHz, DMSO-$d_6$) δ 7.86–7.81 (m, 2H), 7.67 (broad s, 1H), 7.45–7.39 (m, 2H), 5.65 (broad s, 2H), 4.15 (m, 2H), 3.76 (t, J=6.7 Hz, 2H), 3.27 (s, 3H), 3.00 (t, J=6.7 Hz, 2H), 2.90 (broad s, 2H), 2.78 (m, 2H), 2.65 (broad s, 2H), 1.75 (broad s, 4H), 1.61 (m, 2H), 1.43 (m, 2H); MS (Cl) m/e 476 (M+H). Analysis: Calculated for $C_{23}H_{30}FN_5O_3S$: % C, 58.09; % H, 6.36; % N, 14.73; Found: % C, 58.37; % H, 6.35; % N, 14.60.

EXAMPLE 15

N-[4-(4-Amino-2-phenyl-1H-imidazo[4,5-c]quinolin-1-yl)butyl]-4-fluoro-1-benzenesulfonamide

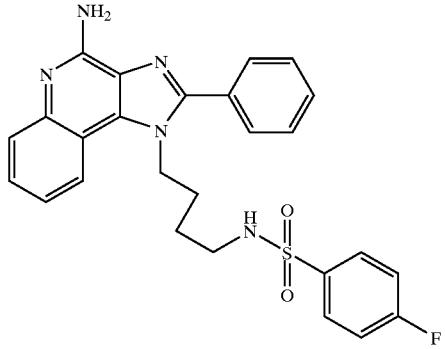

Part A

A solution of benzoyl chloride (5.3 g, 37.7 mmol) in dichloromethane (100 mL) was slowly added to a solution of tert-butyl N-{4-[(3-aminoquinolin-4-yl)amino]butyl}carbamate (12.5 g, 37.7 mmol) in dichloromethane (250 mL) at ambient temperature. The reaction mixture was maintained at ambient temperature overnight. The resulting precipitate was isolated by filtration and dried to provide 11.0 g of tert-butyl N-(4-{[3-(benzoylamino)quinolin-4-yl]amino}butyl)carbamate hydrochloride as a white solid.

Part B

Triethylamine (7.26 g, 71.7 mmol) was added to a solution of the material from Part A in ethanol (200 mL) and heated at reflux for 2 days. The reaction mixture was concentrated to provide an orange syrup. HPLC mass spec analysis showed that the syrup contained the desired product and starting material. The syrup was taken up in dichloromethane (100 mL) and then cooled in an ice bath. Triethylamine (5 mL) and benzoyl chloride (1.9 mL) were added. The reaction mixture was maintained at ambient temperature for 2 days at which time analysis by HPLC indicated that the reaction was not complete. The reaction mixture was concentrated under vacuum. The residue was taken up in isopropyl alcohol (150 mL). Triethylamine (5 mL) was added and the reaction mixture was heated at reflux overnight. The reaction mixture was concentrated under vacuum. The residue was purified by flash chromatography (silica gel; eluting with 10% methanol in dichloromethane). The fractions containing product were combined and concentrated under vacuum. The residue was recrystallized from acetonitrile to provide 6.7 g of tert-butyl N-[4-(2-phenyl-1H-imidazo[4,5-c]quinolin-1-yl)butyl]carbamate as a solid, m.p. 158–159° C.

Part C

3-Chloroperoxybenzoic acid (1.05 eq of 65%) was slowly added in small portions to a solution of tert-butyl N-[4-(2-phenyl-1H-imidazo[4,5-c]quinolin-1-yl)butyl]carbamate (6.56 g, 15.75 mmol) in dichloromethane (120 mL). After 3 hours the reaction was quenched with 1% aqueous sodium bicarbonate (200 mL). The layers were separated. The aqueous layer was extracted with dichloromethane (2×50 mL). The organic fractions were combined, dried over magnesium sulfate and then concentrated under vacuum to provide a pale orange syrup. The syrup was triturated with diethyl ether to provide 6.8 g of 1-[4-(tert-butylcarbamyl)butyl]-2-phenyl-1H-imidazo[4,5-c]quinoline-5N-oxide as a pale tan solid, m.p. 178–181° C.

Part D

A solution of 1-[4-(tert-butylcarbamyl)butyl]-2phenyl-1H-imidazo[4,5-c]quinoline-5N-oxide (6.8 g, 15.75 mmol) in dichloromethane (100 mL) was chilled in an ice bath. Concentrated ammonium hydroxide (30 mL) was added. Tosyl chloride (3.0 g, 15.75 mmol) was added in small portions over a period of 30 minutes. The reaction mixture was allowed to warm to ambient temperature overnight. The reaction was quenched with water (350 mL). The layers were separated. The aqueous layer was extracted with dichloromethane. The organic fractions were combined, dried over magnesium sulfate and then concentrated under vacuum to provide a tan solid. This material was purified by flash chromatography (silica gel eluting with 10% methanol in dichloromethane) to provide 4.8 g of product. The bulk of the material was carried onto the next step. A small portion was recrystallized from toluene to provide tert-butyl N-[4-(4-amino-2-phenyl-1H-imidazo[4,5-c]quinolin-1-yl)butyl]carbamate as a solid, m.p. 182–183° C. Analysis: Calculated for $C_{25}H_{29}N_5O_2$: % C, 69.58; % H, 6.77; % N, 16.22; Found: % C, 69.86; % H, 6.95; % N, 15.80.

Part E

The material from Part D was dissolved in methanol (15 mL) and 1 N hydrochloric acid (100 mL) and then heated at reflux for 2 hours. The reaction mixture was concentrated under vacuum to a volume of about 50 mL. Addition of concentrated animonium hydroxide to pH 12 did not produce a precipitate. The pH was adjusted to 7 with 1 N-hydrochloric acid. The mixture was extracted with dichloromethane and then with ethyl acetate. The aqueous layer was concentrated to dryness. The residue was dissolved in water (50 mL) and then extracted continuously with refluxing chloroform for 36 hours. The chloroform extract was concentrated under vacuum to provide a light tan solid. This material was recrystallized from acetonitrile to provide 2.5 g of 1-(4-aminobutyl)-2-phenyl-1H-imidazo[4,5-c]quinolin-4-amine as an off white solid, m.p. 175–177C. Analysis: Calculated for $C_{20}H_{21}N_5$: % C, 72.48; % H, 6.39; % N, 21.13; Found: % C, 72.72; % H, 6.32; % N, 20.71.

Part F 1-(4-Aminobutyl)-2-phenyl-1H-imidazo[4,5-c]quinolin-4-amine (0.331 g, 1.0 mmol) was dissolved in anhydrous acetonitrile (35 mL) and the solution was cooled to 40° C. A solution of 4-fluorobenzenesulfonyl chloride (0.194 g, 1.0 mmol) in anhydrous dichloromethane (10 mL) was slowly added. The reaction was allowed to slowly warm to ambient temperature over the weekend. The reaction was quenched by the addition of aqueous saturated sodium bicarbonate solution. The layers were separated and the organic layer was concentrated to provide a pale yellow solid. This material was recrystallized from isopropyl alcohol and then further purified by flash chromatography (silica gel eluting with 10% methanol in dichloromethane). The pure fractions were combined and concentrated. The residue was recrystallized from isopropyl alcohol to provide 0.2 g of N-[4-(4-amino-2-phenyl-1H-imidazo[4,5-c]quinolin-1-yl)butyl]-4-fluoro-1-benzenesulfonamide as a pale yellow solid, m.p. 214–216° C. Analysis: Calculated for $C_{26}H_{24}FN_5O_2S$: % C, 63.79; % H, 4.94; % N, 14.30; Found: % C, 63.19; % H, 4.85; % N, 13.90. Mass spec M+1=490.2.

EXAMPLE 16

N-[4-(4-Amino-2-phenyl-1H-imidazo[4,5-c] quinolin-1-yl)butyl]methanesulfonamide

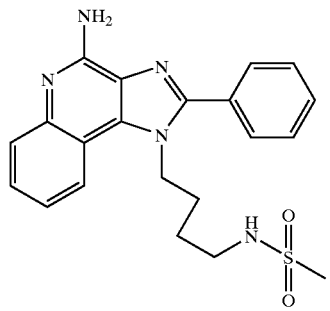

Using the general method of Example 15 Part F, 1-(4-aminobutyl)-2-phenyl-1H-imidazo[4,5-c]quinolin-4-amine (0.331 g, 1.0 mmol) was reacted with methanesulfonic anhydride to provide 0.14 g of N-[4-(4-Amino-2-phenyl-1H-imidazo[4,5-c]quinolin-1-yl)butyl]methanesulfonamide as a white solid, m.p. 234–235° C. Mass spec M+1=410.2.

EXAMPLES 17–33

The compounds shown in the Table below were prepared using the synthetic method described in Reaction Scheme II above.

1-(2-Aminoethyl)-2-butyl-1H-imidazo[4,5-c]quinolin-4-amine (25 mg) was placed in a 2 dram (7.4 mL) vial. Diisopropylethylamine (11 μL, 1.2 eq), dichloromethane (1 mL) and the sulfonyl chloride (1.1 eq) were added in order. The vial was placed on a shaker for about 2 hours and then on a sonicator for about 0.5 hours. The reaction mixture was allowed to stand at ambient temperature overnight and analyzed by LC/MS to confirm the formation of the desired product. The solvent was removed and the residue was purified by semi-preparative HPLC (Capcell Pak C18 column, 35 mm×20 mm, 5 micron particle size, 20 mL/min., gradient elution from 5–95% B in 10 mm., hold at 95% B for 2 mm., where A=0.1% trifluoroacetic acid/water and B=0.1% trifluoroacetic acid/acetonitrile, peak detection at 254 nm for triggering fraction collection). The semi-prep HPLC fractions were analyzed by LC-APCI/MS and the appropriate fractions were combined and lyophilized to provide the trifluoroacetate salt of the desired sulfonamide.

-continued

| Example # | Structure of the Free Base | Observed Mass |
|---|---|---|
| 17 | | 390.2 |
| 18 | | 460.2 |
| 19 | | 430.1 |
| 20 | | 424.1 |
| 21 | | 504.0 |
| 22 | | 492.0 |
| 23 | | 438.1 |
| 24 | | 534.0 |
| 25 | | 480.2 |
| 26 | | 466.2 |

-continued

| Example # | Structure of the Free Base | Observed Mass |
|---|---|---|
| 27 | | 454.1 |
| 28 | | 438.1 |
| 29 | | 450.1 |
| 30 | | 475.1 |
| 31 | | 474.2 |

-continued

| Example # | Structure of the Free Base | Observed Mass |
|---|---|---|
| 32 | | 474.1 |
| 33 | | 517.2 |

EXAMPLE 34
N-[2-(4-Amino-2-butyl-1H-imidazo[4,5-c]quinolin-1-yl)ethyl]methanesulfonamide Trifluoroacetate

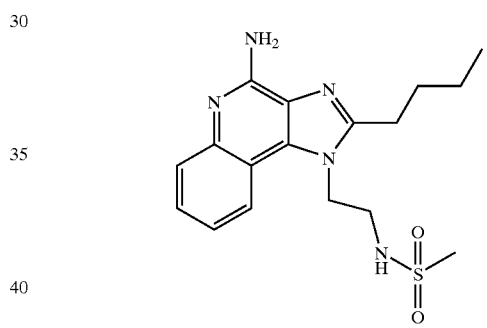

This compound was prepared using the method of Examples 17–33 above except that 1.1 eq of methanesulfonic anhydride was used in place of the sulfonyl chloride. (Observed Mass=362.2)

EXAMPLE 35
N-[2-(4-Amino-2-butyl-1H-imidazo[4,5-c]quinolin-1-yl)ethyl]trifluoromethanesulfonamide Trifluoroacetate

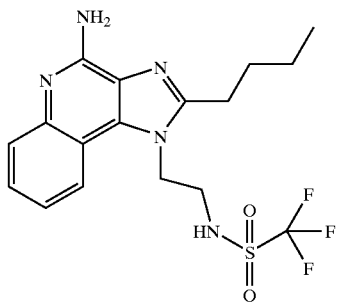

This compound was prepared using the method of Examples 17–33 above except that 1.1 eq of trifluoromethanesulfonic anhydride was used in place of the sulfonyl chloride. (Observed Mass=416.1)

EXAMPLES 36–48

The compounds shown in the Table below were prepared using the synthetic method described in Reaction Scheme II above.

1-(4-Aminobutyl)-2-butyl-1H-imidazo[4,5-c]quinolin-4-amine (25 mg) was placed in a 2 dram (7.4 mL) vial. Diisopropylethylamine (14 µL, 1.0 eq), dichloromethane (1 mL) and the sulfonyl chloride (1.0 eq) were added in order. The vial was placed on a shaker for about 30 minutes at which time almost everything was in solution. Some time later a precipitate formed. A small amount of methanol was added and the precipitate dissolved. The reaction mixture was left on the shaker for an additional hour and then it was put on a sonicator for about 0.5 hours. The reaction mixture was analyzed by LC/MS to confirm the formation of the desired product. The solvent was removed and the residue was purified by semi-preparative HPLC (Capcell Pak C18 column, 35 mm×20 mm, 5 micron particle size, 20 mL/min., gradient elution from 5–95% B in 10 min., hold at 95% B for 2 min., where A=0.1% trifluoroacetic acid/water and B=0.1% trifluoroacetic acid/acetonitrile, peak detection at 254 run for triggering fraction collection). The semi-prep HPLC fractions were analyzed by LC-APCI/MS and the appropriate fractions were combined and lyophilized to provide the trifluoroacetate salt of the desired sulfonamide.

| Example # | Structure of Free Base | Observed Mass |
|---|---|---|
| 36 | | 390.1 |
| 37 | | 482.1 |
| 38 | | 418.1 |
| 39 | | 452.1 |
| 40 | | 466.1 |

EXAMPLES 41–52

The compounds shown in the Table below were prepared using the synthetic method described in Reaction Scheme II above.

1-(4-Aminobutyl)-2-butyl-1H-imidazo[4,5-c]quinolin-4-amine (25 mg) was placed in a 2 dram (7.4 mL) vial. Diisopropylethylamine (14 µL, 1.0 eq), dichloromethane (1 mL) and the sulfonyl chloride (1.0 eq) were added in order. The vial was placed on a sonicator at ambient temperature for about 60 minutes. The reaction mixture was analyzed by LC/MS to confirm the formation of the desired product. The solvent was removed and the residue was purified by semi-preparative HPLC (Capcell Pak C18 column, 35 mm×20 mm, 5 micron particle size, 20 mL/min., gradient elution from 5–95% B in 10 mm., hold at 95% B for 2 mm., where A=0.1 % trifluoroacetic acid/water and B=0.1% trifluoroacetic acid/acetonitrile, peak detection at 254 nm for triggering fraction collection). The semi-prep HPLC fractions were analyzed by LC-APCI/MS and the appropriate fractions were combined and lyophilized to provide the trifluoroacetate salt of the desired sulfonamide.

-continued
| Example # | Structure of Free Base | Observed Mass |
|---|---|---|
| 41 | 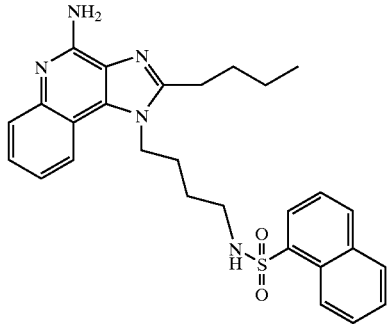 | 502.1 |
| 42 | 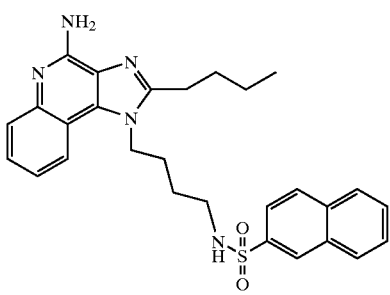 | 502.1 |
| 43 | 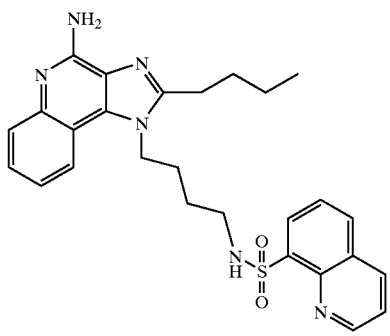 | 503.2 |
| 44 | 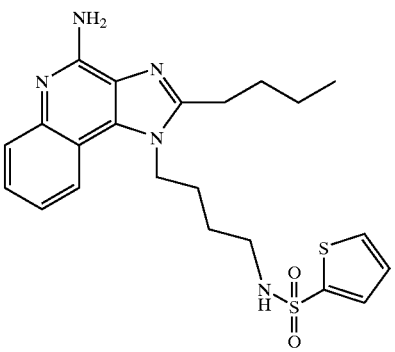 | 458.1 |
| 45 | 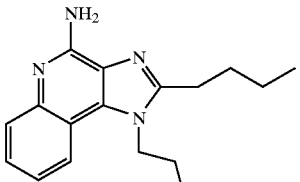 | 494.2 |
| 46 | 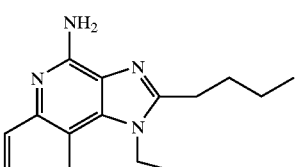 | 578.2 |
| 47 | 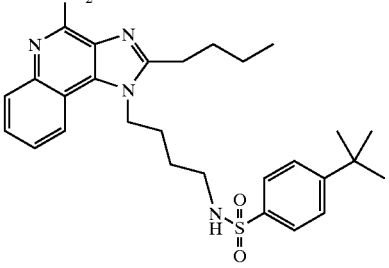 | 508.3 |
| 48 | 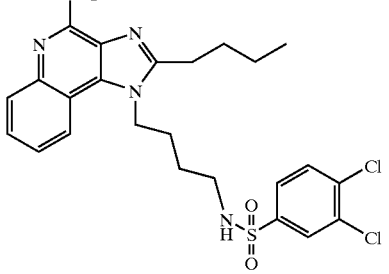 | 520.1 |

-continued

| Example # | Structure of Free Base | Observed Mass |
|---|---|---|
| 49 | | 466.2 |
| 50 | | 478.2 |
| 51 | | 418.2 |
| 52 | | 560.1 |

EXAMPLE 53

N-[2-(4-Amino-2-butyl-1H-imidazo[4,5-c]quinolin-1-yl)butyl]trifluoromethanesulfamide Trifluoroacetate

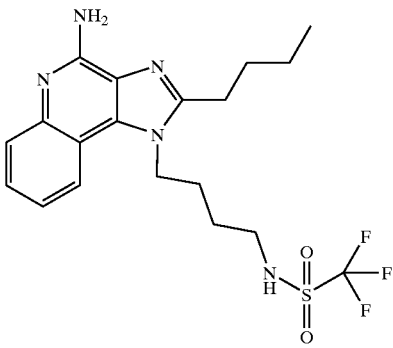

This compound was prepared using the method of Examples 41–52 above except that 1.0 eq of trifluoromethanesulfonic anhydride was used in place of the sulfonyl chloride. (Observed Mass=444.1)

EXAMPLES 54–71

The compounds shown in the Table below were prepared using the synthetic method described in Reaction Scheme IV above.

Part A

A catalytic amount of platinum (IV) oxide was added to a solution of 1-(4-aminobutyl)-1H-imidazo[4,5-c]quinolin-4amine (2.75 g, 10.8 mmol) in trifluoroacetic acid (150 mL). The reaction mixture was placed under a hydrogen atmosphere at 50 psi ($3.44 \times 10^5$ Pa). After 1 week analysis by mass spectroscopy indicated the presence of both starting material and the tetrahydro product. Fresh catalyst was added to the reaction mixture and hydrogenation was continued at 50 psi ($3.44 \times 10^5$ Pa). After 2 weeks the reaction mixture was filtered to remove the catalyst. The filtrate was concentrated under vacuum. The residue was dissolved in 1N hydrochloric acid (120 mL) and the solution was stirred at ambient temperature for 1 hour. The solution was made basic (pH 10) by the addition of 50% sodium hydroxide and then extracted with dichloromethane (5×100 mL). The extracts were combined and concentrated under vacuum to provide 2.08 g of 1-(4-aminobutyl)-6,7,8,9-tetrahydro-1H-imidazo[4,5-c]quinolin-4-amine as a white solid.

Part B 1-(4-Aminobutyl)-6,7,8,9-tetrahydro-1H-imidazo[4,5-c]quinolin-4-amino (25 mg) was placed in a 2 drain (7.4 ml) vial. Diisopropylethylaniine (11 μL, 1.2 eq), dichloromethane (1 mL) and the sulfonyl chloride (1.1 eq) were added in order. The vial was placed on a shaker for about 6 hours. The reaction mixture was allowed to stand at ambient temperature overnight and was analyzed by LC/MS to confirm the formation of the desired product. The solvent was removed and the residue was purified by semi-preparative HPLC (Capcell Pak C18 column, 35 mm×20 mm, 5 micron particle size, 20 mL/min., gradient elution from 5–95% B in 10 mm., hold at 95% B for 2 min., where A=0.1% trifluoroacetic acid/water and B=0.1% trifluoroacetic acid/acetonitrile, peak detection at 254 nm for triggering fraction collection). The semi-prep HPLC fractions were analyzed by LC-APCI/MS and the appropriate fractions were combined and lyophilized to provide the trifluoroacetate salt of the desired sulfonamide.

| Example # | Structure of Free Base | Observed Mass |
|---|---|---|
| 54 | 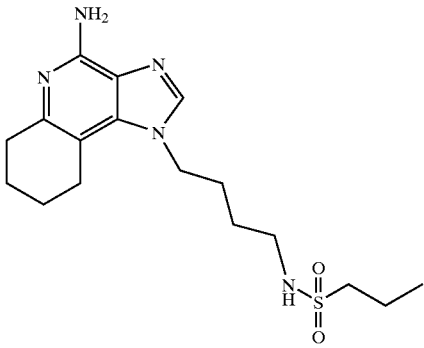 | 366.2 |
| 55 | 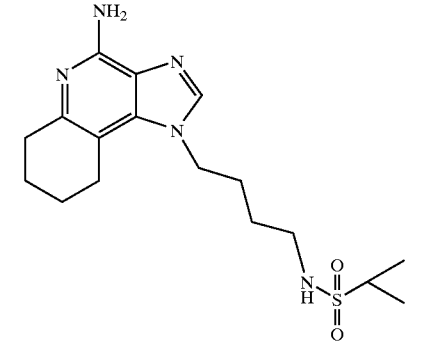 | 366.1 |
| 56 | 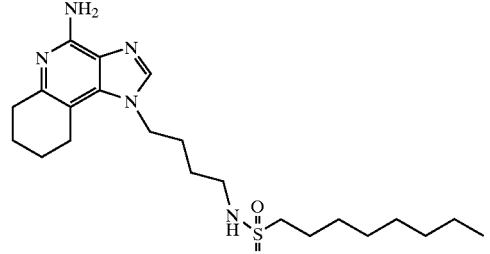 | 436.2 |
| 57 | 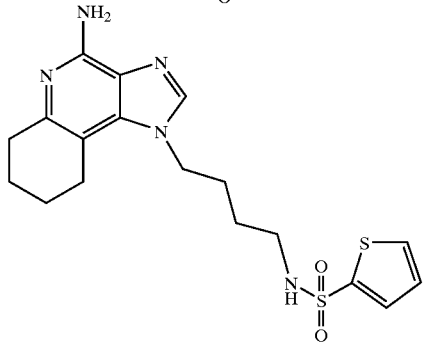 | 406.1 |
| 58 | 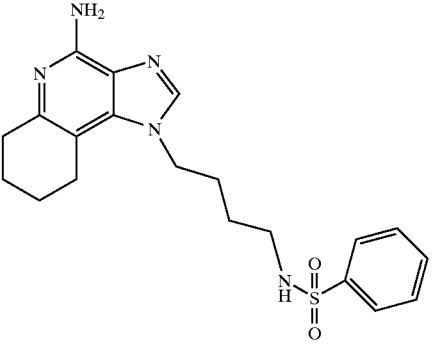 | 400.1 |

-continued

| Example # | Structure of Free Base | Observed Mass |
|---|---|---|
| 59 | | 434.0 |
| 60 | | 468.0 |
| 61 | | 526.0 |
| 62 | | 456.1 |

-continued

| Example # | Structure of Free Base | Observed Mass |
|---|---|---|
| 63 | | 442 |
| 64 | | 414 |
| 65 | | 430 |
| 66 | | 508.0 |

-continued

| Example # | Structure of Free Base | Observed Mass |
|---|---|---|
| 67 | | 414.1 |
| 68 | | 426.1 |
| 69 | | 451.1 |
| 70 | | 450.1 |

| Example # | Structure of Free Base | Observed Mass |
|---|---|---|
| 71 | | 493.1 |

EXAMPLE 72

N-[4-(4-Amino-6,7,8,9-tetrahydro-1H-imidazo[4,5-c]quinolin-1-yl)butyl]methanesulfonamide Trifluoroacetate

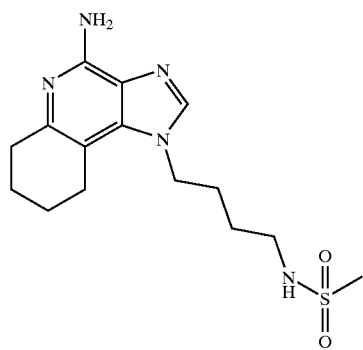

This compound was prepared using the method of Examples 54–71 above except that 1.1 eq of methanesulfonic anhydride was used in place of the sulfonyl chloride. (Observed Mass=338.2)

EXAMPLES 73–201

The compounds in the table below were prepared according the synthetic method of Reaction Scheme II above using the following general method.

The 1H-imidazo[4,5-c]quinolin-4-amine (50 mg) was placed in a 2 dram (7.4 mL) vial. Diisopropylethylamine (1.2 eq) in dichloromethane (~1 mL) was added. A solution containing the sulfonyl chloride (1.1 eq.) in dichloromethane (~1 mL) was added. The vial was placed on a shaker for about 2–16 (usually 2) hours at ambient temperature. The reaction mixture was analyzed by LC/MS to confirm the formation of the desired product. The solvent was removed and the residue was purified by semi-preparative HPLC (Capcell Pak C18 column, 35 mm×20 mm, 5 micron particle size, 20 mL/min., gradient elution from 5–95% B in 10 mm., hold at 95% B for 2 mm., where A=0.1% trifluoroacetic acid/water and B=0.1 % trifluoroacetic acid/acetonitrile, peak detection at 254 nm for triggering fraction collection). The semi-prep HPLC fractions were analyzed by LC-APCI/MS and the appropriate fractions were combined and lyophilized to provide the trifluoroacetate salt of the desired sulfonamide.

| Example # | Structure of the Free Base | APCI-MS m/e |
|---|---|---|
| 73 | | 526.2 |

-continued

| Example # | Structure of the Free Base | APCI-MS m/e |
|---|---|---|
| 74 | | 432.2 |
| 75 | | 600.3 |
| 76 | | 578.2 |
| 77 | | 530.1 |

-continued

| Example # | Structure of the Free Base | APCI-MS m/e |
|---|---|---|
| 78 | | 530, 532.0 |
| 79 | | 565.0 |
| 80 | | 520.1 |
| 81 | | 512.1 |

-continued

| Example # | Structure of the Free Base | APCI-MS m/e |
| --- | --- | --- |
| 82 | (4-amino-2-butyl-1H-imidazo[4,5-c]quinolin-1-yl)butyl sulfonamide with 2-chloroethyl group | 452.1 |
| 83 | (4-amino-2-butyl-1H-imidazo[4,5-c]quinolin-1-yl)butyl sulfonamide with 3-nitrophenyl group | 497.1 |
| 84 | (4-amino-2-butyl-1H-imidazo[4,5-c]quinolin-1-yl)butyl sulfonamide with 4-carboxyphenyl group | 496.1 |
| 85 | (4-amino-2-butyl-1H-imidazo[4,5-c]quinolin-1-yl)butyl sulfonamide with 4-(trifluoromethoxy)phenyl group | 536.1 |

-continued

| Example # | Structure of the Free Base | APCI-MS m/e |
|---|---|---|
| 86 | | 531.0, 533.0 |
| 87 | | 470.1 |
| 88 | | 497.1 |
| 89 | | 526.2 |

-continued

| Example # | Structure of the Free Base | APCI-MS m/e |
| --- | --- | --- |
| 90 | | 542.0 |
| 91 | | 536.1 |
| 92 | | 520.0, 522.0 |
| 93 | | 488.1 |

| Example # | Structure of the Free Base | APCI-MS m/e |
|---|---|---|
| 94 | | 471.1 |
| 95 | | 470.1 |
| 96 | | 528.1 |
| 97 | | 511.1 |

-continued

| Example # | Structure of the Free Base | APCI-MS m/e |
|---|---|---|
| 98 | | 508.1 |
| 99 | | 537.9 |
| 100 | | 516.0, 518.0 |
| 101 | | 492.0, 494.0 |

-continued
| Example # | Structure of the Free Base | APCI-MS m/e |
|---|---|---|
| 102 | 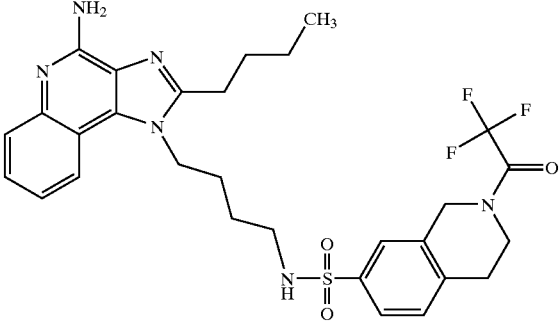 | 603.1 |
| 103 | 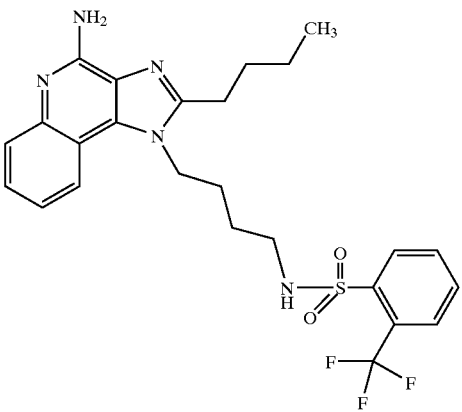 | 520.1 |
| 104 | 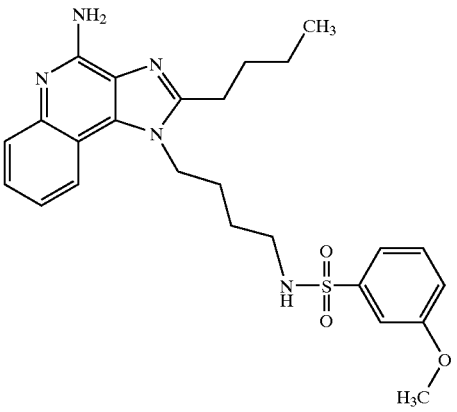 | 482.1 |
| 105 | 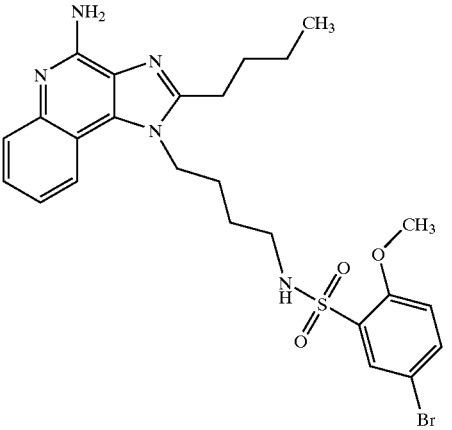 | 560.0, 562 |

-continued

| Example # | Structure of the Free Base | APCI-MS m/e |
|---|---|---|
| 106 | | 484.1 |
| 107 | | 522.1 |
| 108 | | 364.1 |
| 109 | | 432.0 |
| 110 | | 519.1 |

-continued

| Example # | Structure of the Free Base | APCI-MS m/e |
|---|---|---|
| 111 | | 392.2 |
| 112 | | 460.1 |
| 113 | | 468.2 |
| 114 | | 547.3 |

-continued
| Example # | Structure of the Free Base | APCI-MS m/e |
|---|---|---|
| 115 | 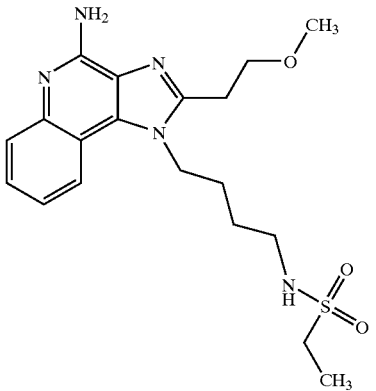 | 406.1 |
| 116 | 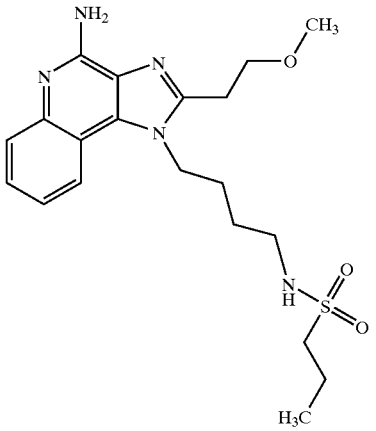 | 420.1 |
| 117 | 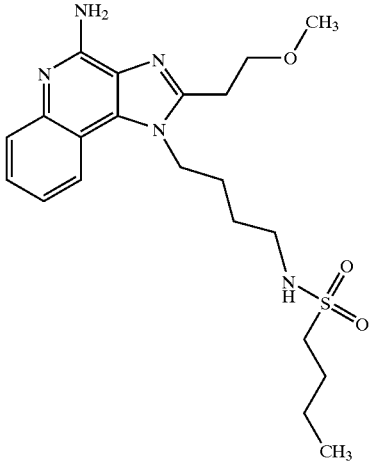 | 434.1 |

-continued

| Example # | Structure of the Free Base | APCI-MS m/e |
|---|---|---|
| 118 | | 454.1 |
| 119 | | 468.1 |
| 120 | | 472.1 |

-continued
| Example # | Structure of the Free Base | APCI-MS m/e |
|---|---|---|
| 121 | 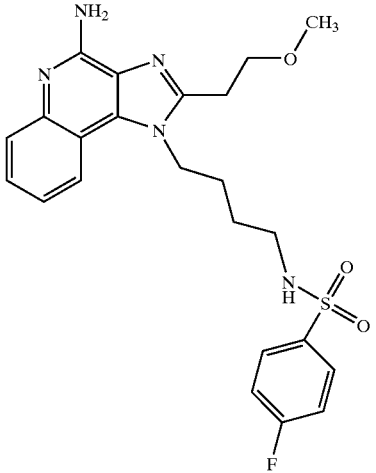 | 472.1 |
| 122 | 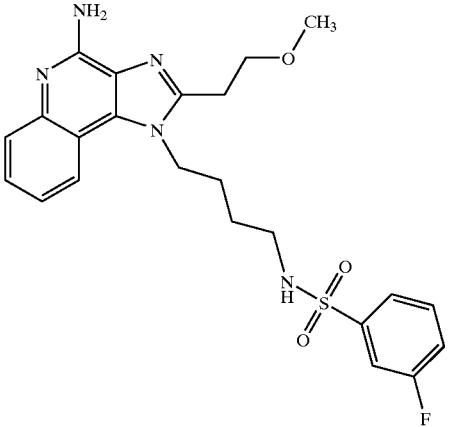 | 472.1 |
| 123 | 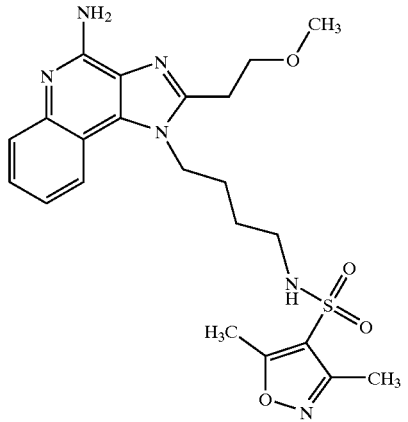 | 473.1 |

-continued

| Example # | Structure of the Free Base | APCI-MS m/e |
|---|---|---|
| 124 | 4-amino-2-(2-methoxyethyl)-1-{4-[(3-methoxyphenyl)sulfonylamino]butyl}-1H-imidazo[4,5-c]quinoline | 484.1 |
| 125 | 4-amino-2-(2-methoxyethyl)-1-{4-[(4-methoxyphenyl)sulfonylamino]butyl}-1H-imidazo[4,5-c]quinoline | 484.1 |
| 126 | 4-amino-1-{4-[(3-chlorophenyl)sulfonylamino]butyl}-2-(2-methoxyethyl)-1H-imidazo[4,5-c]quinoline | 488.1 |

-continued

| Example # | Structure of the Free Base | APCI-MS m/e |
|---|---|---|
| 127 | | 488.1 |
| 128 | | 488.0 |
| 129 | | 490.1 |

-continued
| Example # | Structure of the Free Base | APCI-MS m/e |
|---|---|---|
| 130 | 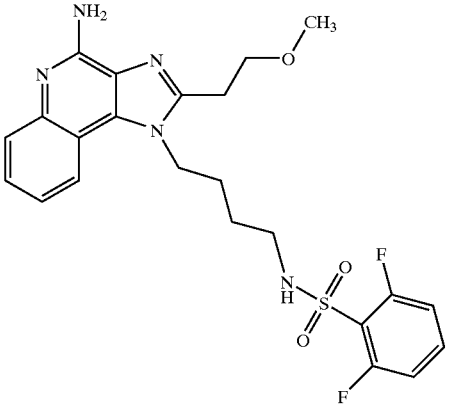 | 490.1 |
| 131 | 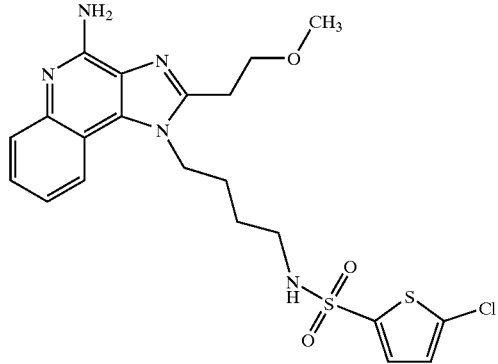 | 494.0 |
| 132 | 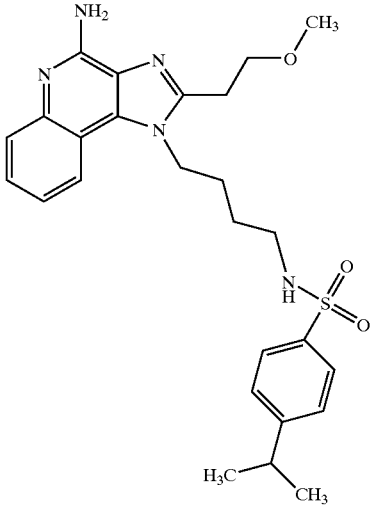 | 496.2 |

-continued
| Example # | Structure of the Free Base | APCI-MS m/e |
|---|---|---|
| 133 | 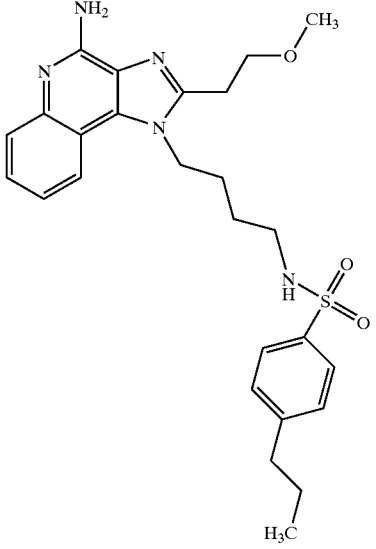 | 496.1 |
| 134 | 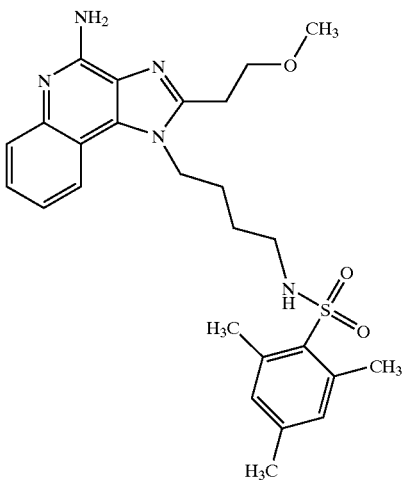 | 496.2 |
| 135 | 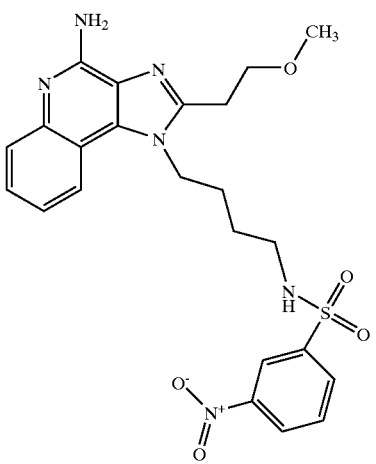 | 499.1 |

| Example # | Structure of the Free Base | APCI-MS m/e |
|---|---|---|
| 136 | 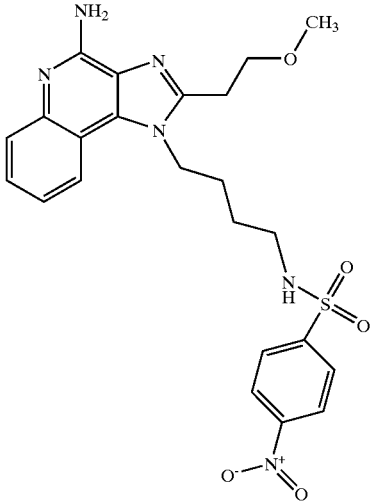 | 499.1 |
| 137 | 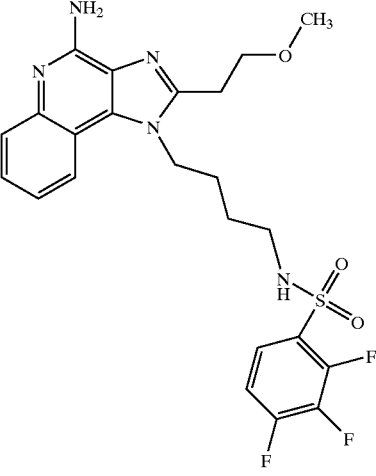 | 508.1 |
| 138 | 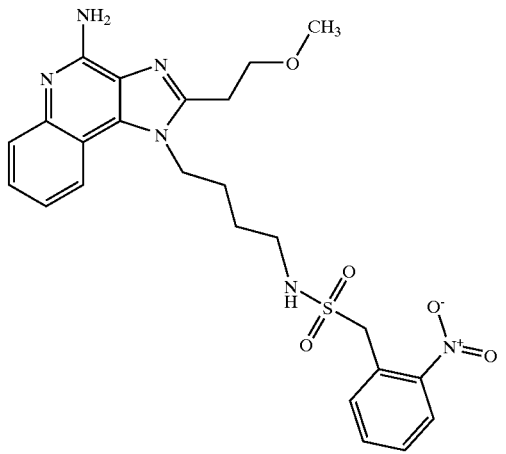 | 513.1 |

-continued
| Example # | Structure of the Free Base | APCI-MS m/e |
|---|---|---|
| 139 | 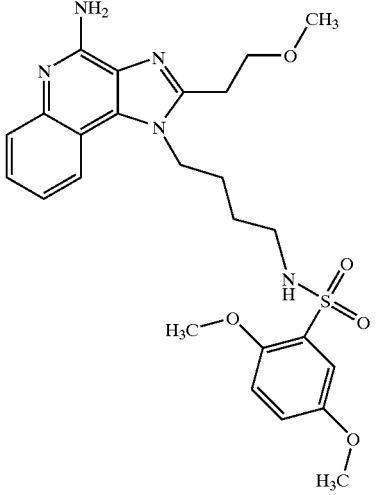 | 514.1 |
| 140 | 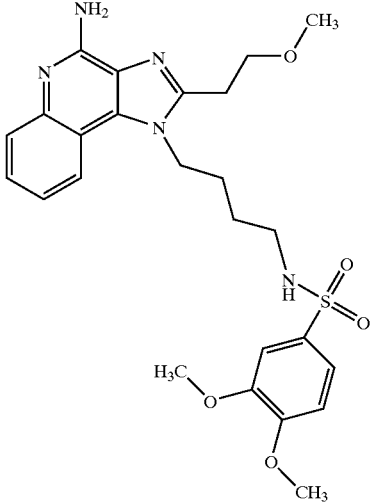 | 514.1 |
| 141 | 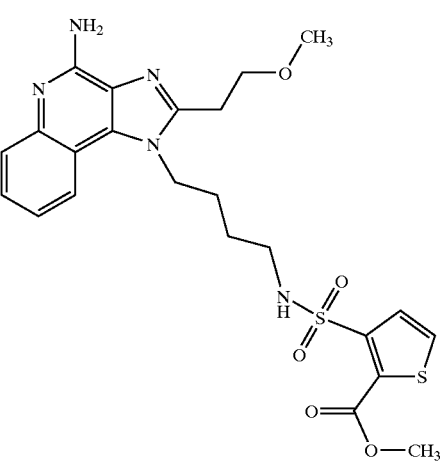 | 518.0 |

-continued
| Example # | Structure of the Free Base | APCI-MS m/e |
|---|---|---|
| 142 | 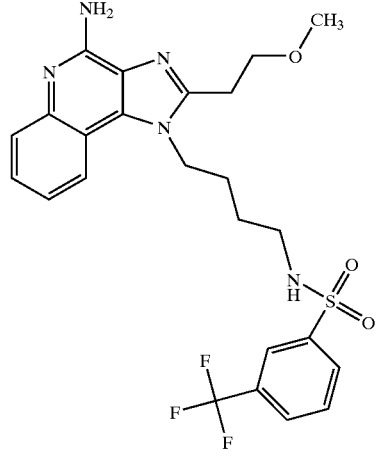 | 522.1 |
| 143 | 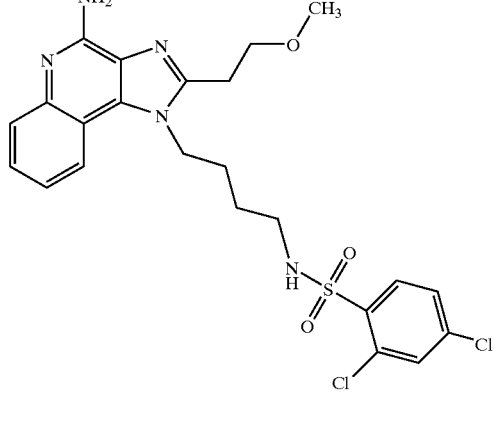 | 522.0, 524.0 |
| 144 | 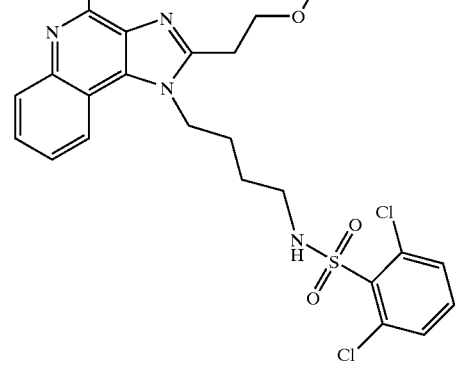 | 522.0, 524.0 |

| Example # | Structure of the Free Base | APCI-MS m/e |
|---|---|---|
| 145 | 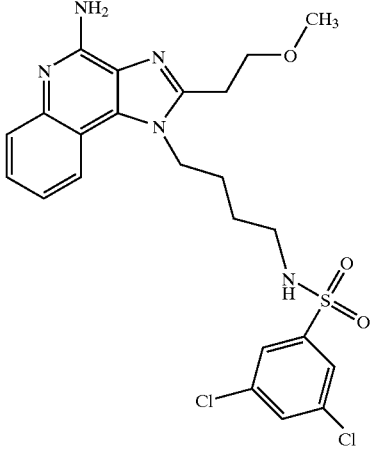 | 522.0, 524.0 |
| 146 | 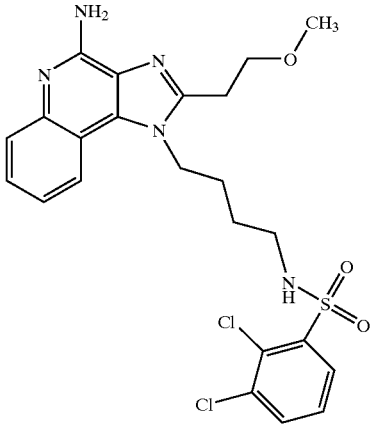 | 522.0, 524.0 |
| 147 | 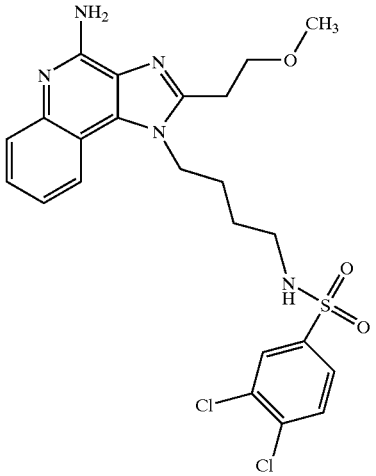 | 522.0, 524.0 |

-continued

| Example # | Structure of the Free Base | APCI-MS m/e |
|---|---|---|
| 148 | | 528.2 |
| 149 | | 528.0, 530.0 |
| 150 | | 528.0, 530.0 |
| 151 | | 532, 534.0 |

-continued

| Example # | Structure of the Free Base | APCI-MS m/e |
|---|---|---|
| 152 | | 532, 534.0 |
| 153 | | 538.1 |
| 154 | | 538.1 |

| Example # | Structure of the Free Base | APCI-MS m/e |
|---|---|---|
| 155 | 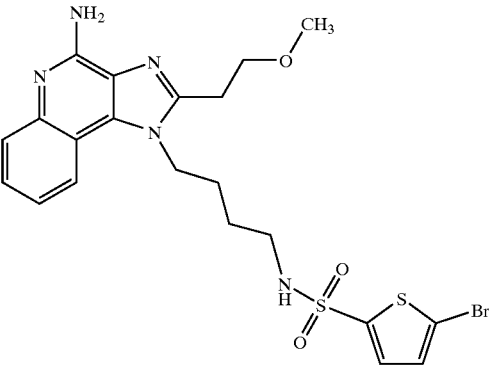 | 538, 540.0 |
| 156 | 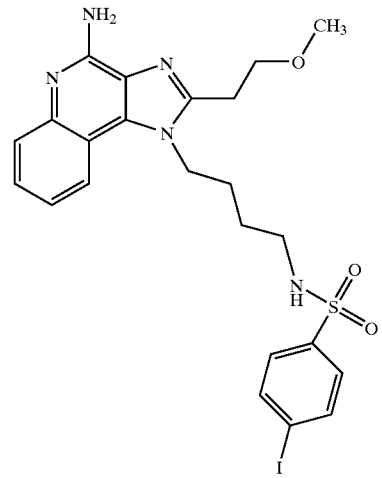 | 580.0 |
| 157 | 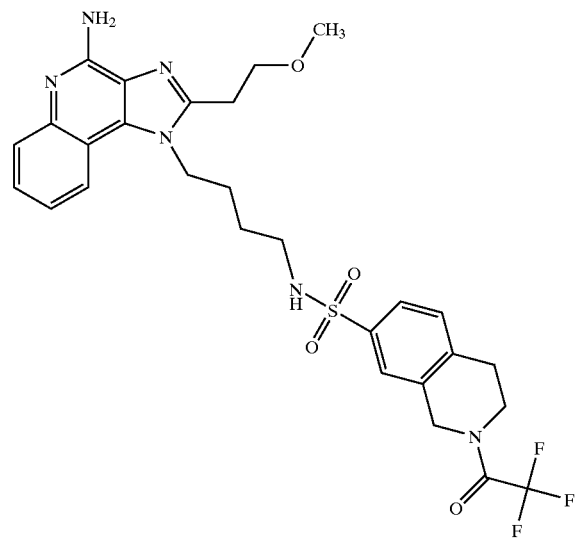 | 605.1 |

-continued

| Example # | Structure of the Free Base | APCI-MS m/e |
|---|---|---|
| 158 | | 454.2 |
| 159 | | 468.2 |
| 160 | | 479.2 |

-continued

| Example # | Structure of the Free Base | APCI-MS m/e |
|---|---|---|
| 161 | | 532.2 |
| 162 | | 479.1 |
| 163 | | 486.1 |

-continued

| Example # | Structure of the Free Base | APCI-MS m/e |
|---|---|---|
| 164 | | 490.2 |
| 165 | | 498.1 |
| 166 | | 498.1 |
| 167 | | 502.1 |

-continued

| Example # | Structure of the Free Base | APCI-MS m/e |
|---|---|---|
| 168 | | 502.1 |
| 169 | | 504.2 |
| 170 | | 504.1 |

-continued
| Example # | Structure of the Free Base | APCI-MS m/e |
|---|---|---|
| 171 | 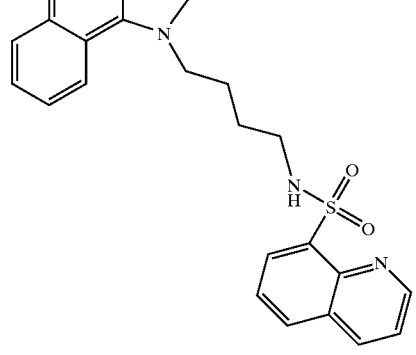 | 505.2 |
| 172 | 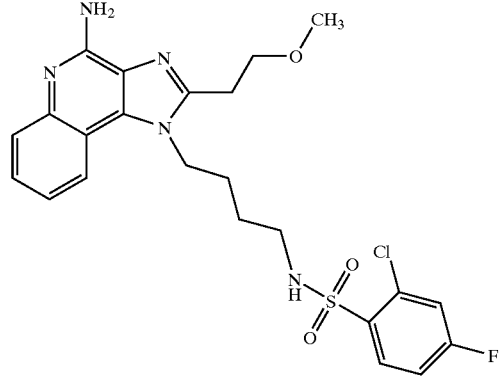 | 506.1 |
| 173 | 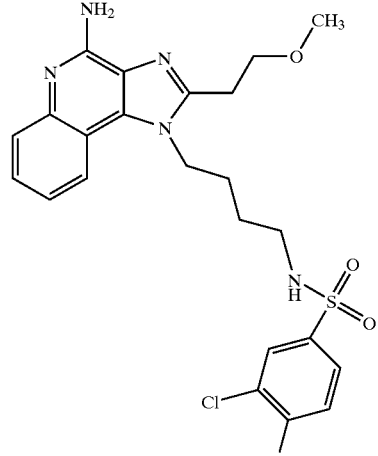 | 506.2 |

-continued
| Example # | Structure of the Free Base | APCI-MS m/e |
|---|---|---|
| 174 | 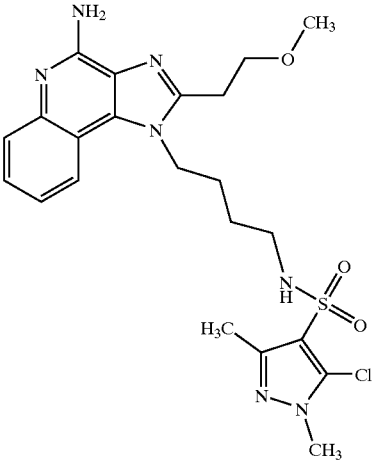 | 506.2 |
| 175 | 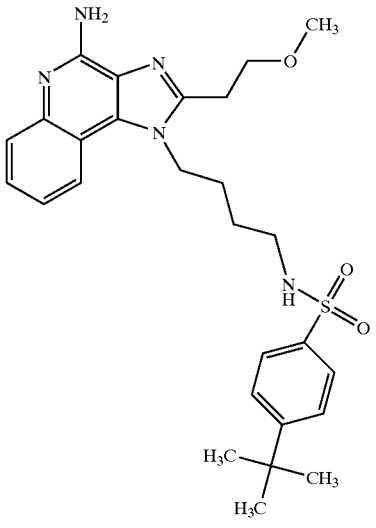 | 510.3 |
| 176 | 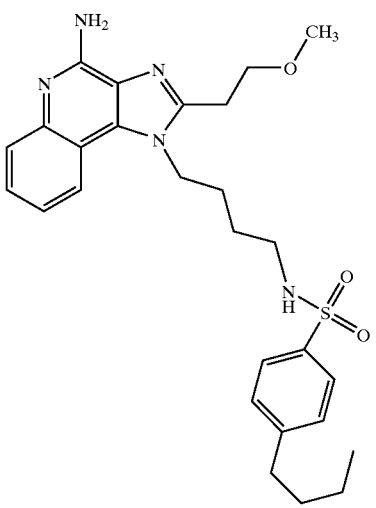 | 510.2 |

-continued
| Example # | Structure of the Free Base | APCI-MS m/e |
|---|---|---|
| 177 | 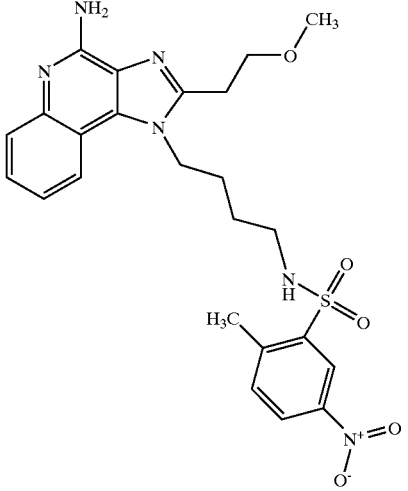 | 513.2 |
| 178 | 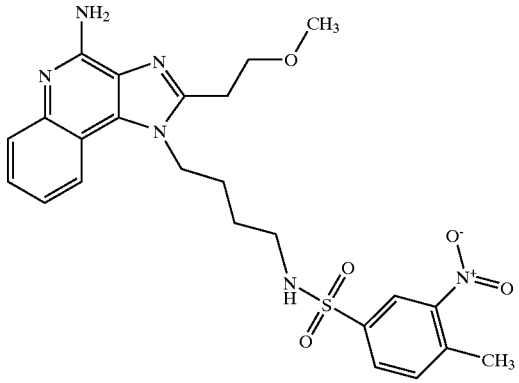 | 513.2 |
| 179 | 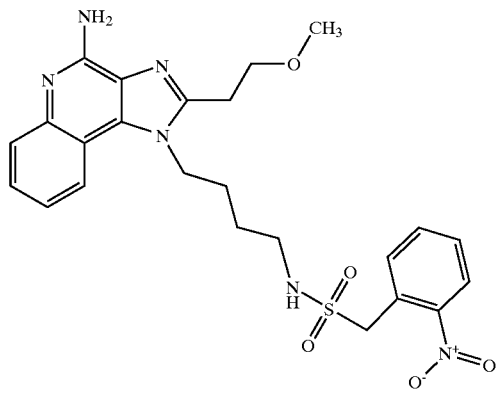 | 513.2 |

| Example # | Structure of the Free Base | APCI-MS m/e |
|---|---|---|
| 180 | 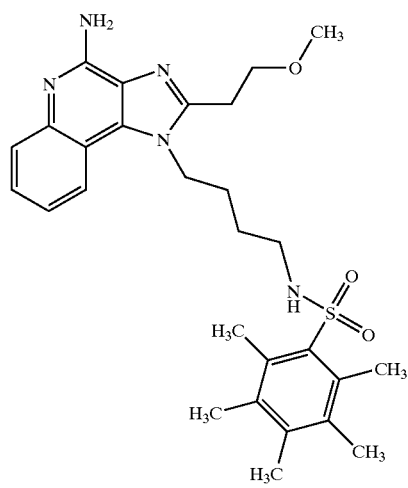 | 524.2 |
| 181 | 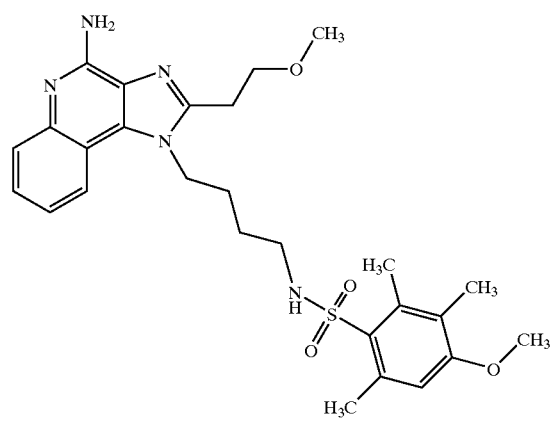 | 526.2 |
| 182 | 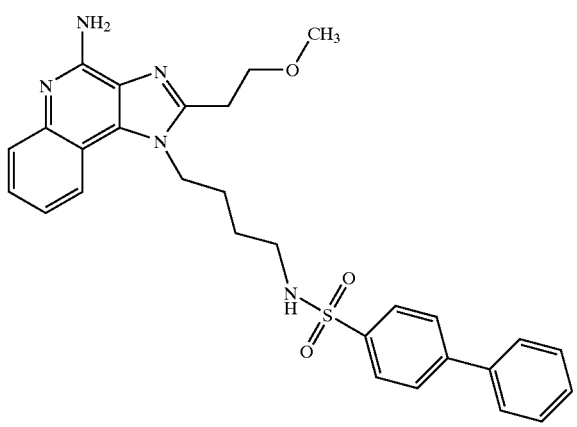 | 530.2 |

-continued
| Example # | Structure of the Free Base | APCI-MS m/e |
|---|---|---|
| 183 | 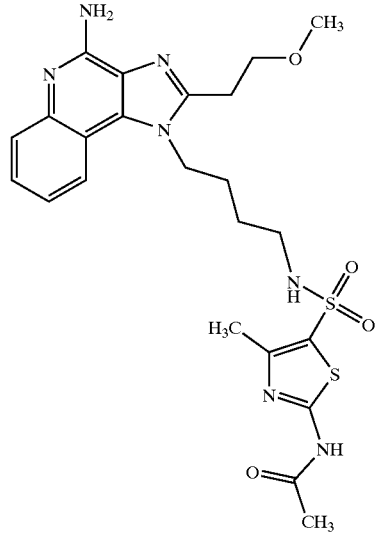 | 532.2 |
| 184 | 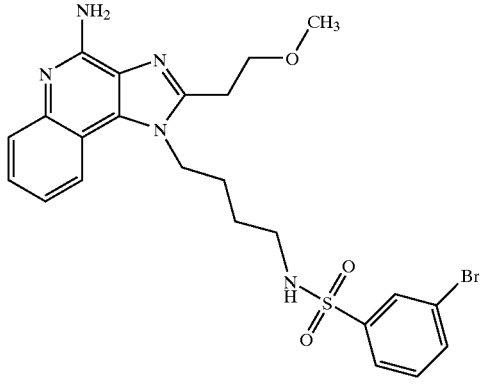 | 534.1 |
| 185 | 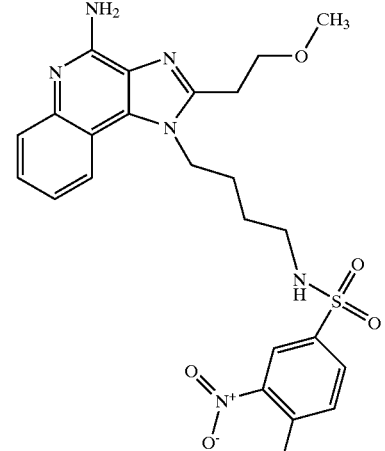 | 533.1 |

-continued
| Example # | Structure of the Free Base | APCI-MS m/e |
|---|---|---|
| 186 | 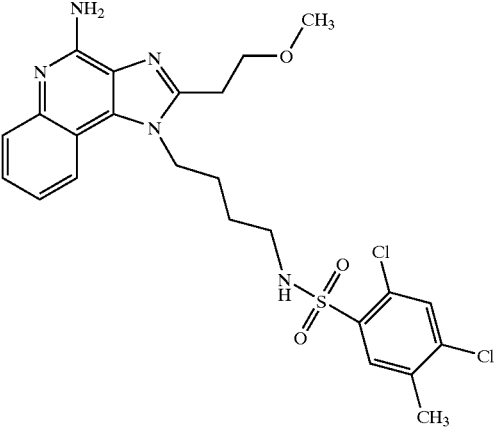 | 536.1, 538.1 |
| 187 | 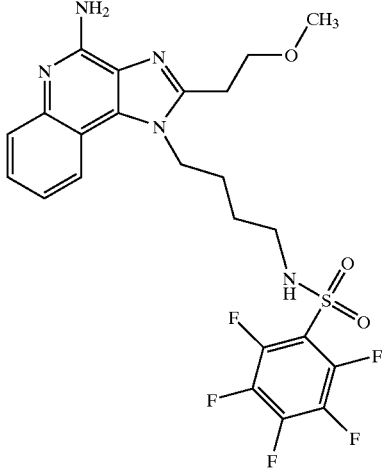 | 544.1 |
| 188 | 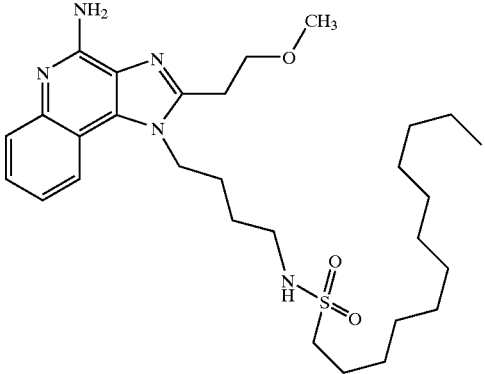 | 546.3 |

-continued
| Example # | Structure of the Free Base | APCI-MS m/e |
|---|---|---|
| 189 | 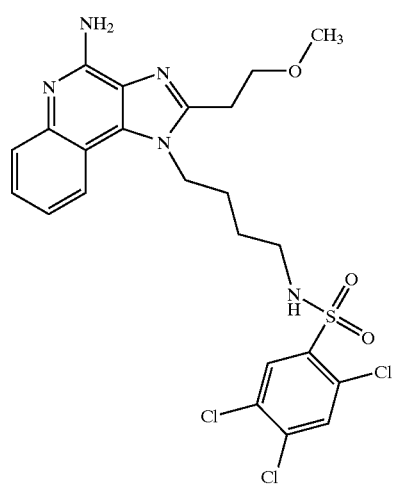 | 556, 558.1 |
| 190 | 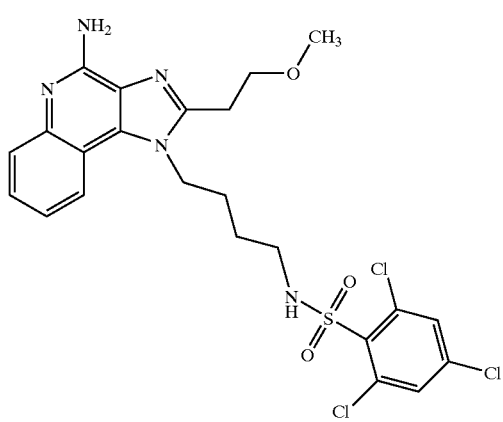 | 556, 558.1 |
| 191 | 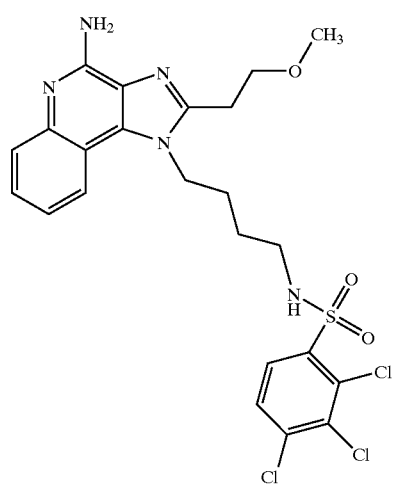 | 556, 558.1 |

-continued

| Example # | Structure of the Free Base | APCI-MS m/e |
|---|---|---|
| 192 | | 562, 564.1 |
| 193 | | 567.2 |
| 194 | | 580.3 |

-continued

| Example # | Structure of the Free Base | APCI-MS m/e |
|---|---|---|
| 195 | | 593.2 |
| 196 | | 606.0, 608.0, 609.9 |
| 197 | | 610.0, 612.0, 614.0 |

-continued
| Example # | Structure of the Free Base | APCI-MS m/e |
|---|---|---|
| 198 | 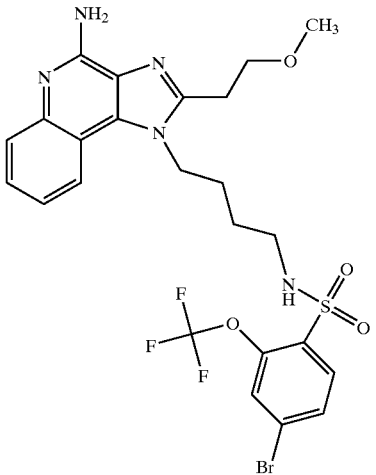 | 616, 618.1 |
| 199 | 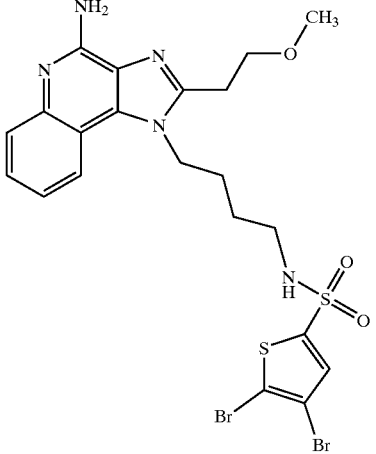 | 616.0, 617.9, 620.0 |
| 200 | 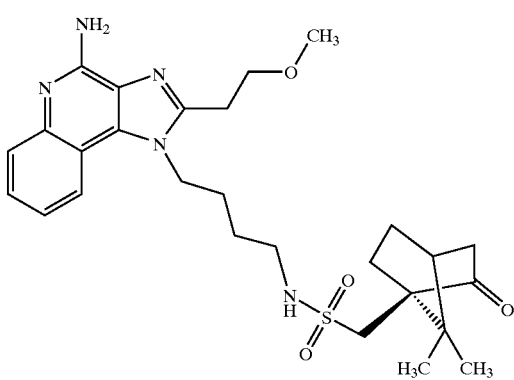 | 528.3 |

-continued

| Example # | Structure of the Free Base | APCI-MS m/e |
|---|---|---|
| 201 | (structure shown: 4-amino-2-(4-methoxybenzyl)-1-[4-(thiophene-2-sulfonamido)butyl]-1H-imidazo[4,5-c]quinoline) | 522.2 |

EXAMPLES 202–213

The examples in the table below were prepared according to the synthetic method of Reaction Scheme VI above.

Part A

The tetrahydroquinoline amine starting materials were prepared as follows.

A catalytic amount of platinum (IV) oxide was added to a solution of 1-(4-aminobutyl)-2-butyl-1H-imidazo[4,5-c]quinolin-4-amine (2.2 g, 7.06 mmol) in trifluoroacetic acid (200 mL). The reaction mixture was hydrogenated at 50 psi ($3.44 \times 10^5$ Pa) on a Parr apparatus for 6 days. The reaction mixture was filtered to remove the catalyst and the filtrate was concentrated under vacuum. The residue was combined with 1 N hydrochloric acid (100 mL) and heated on a steam bath for 2 hours. The mixture was cooled, made basic with animonium hydroxide and then extracted with dichloromethane. The extract was concentrated under vacuum to provide of 1-(4-aminobutyl)-2-butyl-6,7,8,9-tetrahydro-1H-imidazo[4,5-c]quinolin-4-amine as a solid, m.p. 63–67° C.

A catalytic amount of platinum (IV) oxide was added to a solution of 1-(4-aminobutyl)-2-methoxyethyl-1H-imidazo[4,5-c]quinolin-4-amine (7.7 g, 24.5 mmol) in trifluoroacetic acid (250 mL). The reaction mixture was hydrogenated at 50 psi ($3.44 \times 10^5$ Pa) on a Parr apparatus. The progress of the reaction was monitored by LC/MS. Additional catalyst was added 7, 11, and 17 days after the start of the reaction. After 25 days the reaction was complete. The reaction mixture was filtered through a layer of Celite®filter aid to remove the catalyst and the filtrate was concentrated under vacuum. The residue was combined with 1 N hydrochloric acid (100 mL) and stirred overnight. The mixture was made basic (pH=11) with ammonium hydroxide and then extracted with dichloromethane (3×300 mL). The extracts were combined and concentrated under vacuum to provide 3.5 g of 1-(4-aminobutyl)-6,7,8,9-tetrahydro-2-methoxyethyl-1H-imidazo[4,5-c]quinolin-4-amine as a solid.

Part B

The tetrahydroimidazoquinoline amines from Part A were reacted with the appropriate sulfonyl chloride using the method of Examples 73–201 above to provide the desired sulfonamide.

| Example # | Structure of the Free Base | APCI-MS m/e |
|---|---|---|
| 202 | (structure shown: 4-amino-2-propyl-1-[4-(methanesulfonamido)butyl]-6,7,8,9-tetrahydro-1H-imidazo[4,5-c]quinoline) | 394.20 |

-continued

| Example # | Structure of the Free Base | APCI-MS m/e |
|---|---|---|
| 203 | | 422.1 |
| 204 | | 462.1 |
| 205 | | 470.1 |
| 206 | | 549.2 |

-continued
| Example # | Structure of the Free Base | APCI-MS m/e |
|---|---|---|
| 207 | 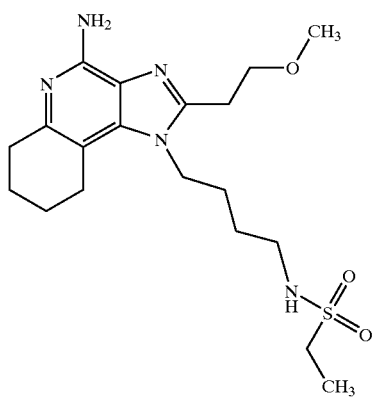 | 410.2 |
| 208 | 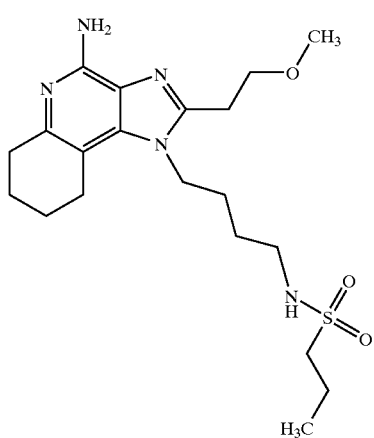 | 424.2 |
| 209 | 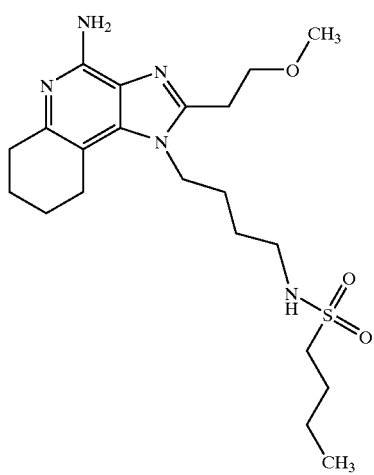 | 438.2 |

-continued
| Example # | Structure of the Free Base | APCI-MS m/e |
|---|---|---|
| 210 | 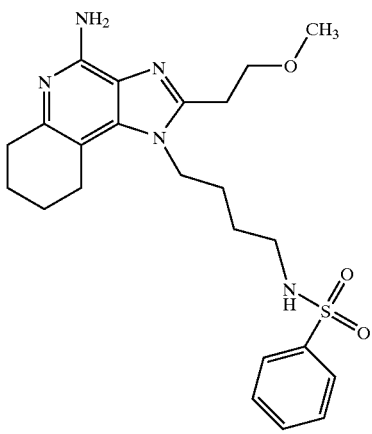 | 458.1 |
| 211 | 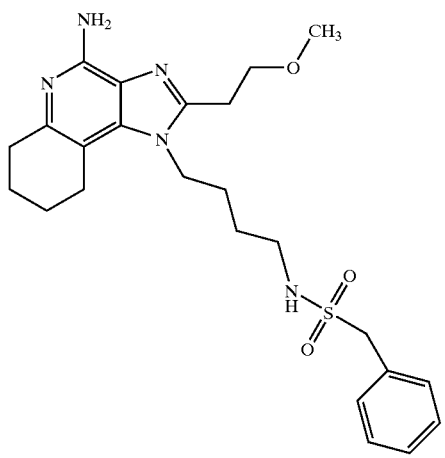 | 472.2 |
| 212 | 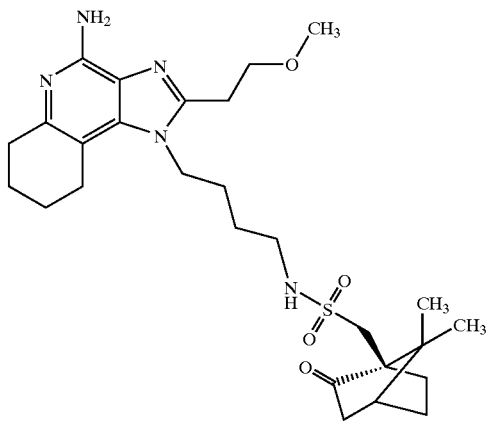 | 532.2 |

| Example # | Structure of the Free Base | APCI-MS m/e |
|---|---|---|
| 213 | 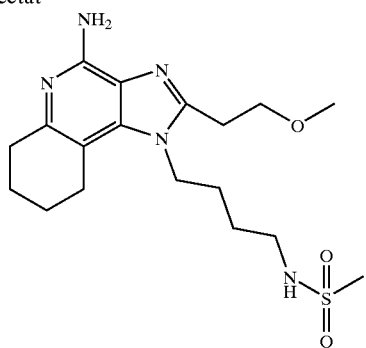 | 551.2 |

EXAMPLE 214

N-[4-(4-Amino-6,7,8,9-tetrahydro-2-(2-methoxyethyl)-1H-imidazo[4,5-c]quinolin-1-yl)butyl]methanesulfonamide Trifluoroacetat

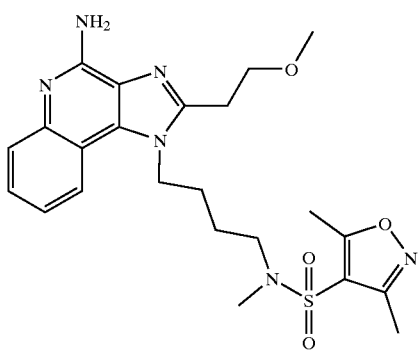

This compound was prepare using the method of Examples 202–213 above except that methanesulfonic anhydride was used in place of the sulfonyl chloride.

EXAMPLE 215

N-[4-(4-Amino-2-(2-methoxyethyl)-1H-imidazo[4,5-c]quinolin-1-yl)butyl]-N-methyl -3,5-dimethylisooxazolo-4-sulfonamide Trifluoroacetate Part A Using the general method of Example DC001, 1-(4-aminobutyl)-2-(2-methoxyethyl)-1H-imidazo[4,5-c] quinolin-4-amine was reacted with 3,5-dimethyloxazole-4-sulfonyl chloride to provide N-[4-(4-amino -2-(2-methoxyethyl)-1H-imidazo[4,5-c]quinolin-1-yl)butyl]-3,5-dimethylisooxazolo-4-sulfonamide trifluoroacetate.

Part B

Sodium hydride (5.8 mg) was added to a solution of the material from Part A (25.4 mg) in dimethylformamide. Iodomethane (3.2 μL) was added and the reaction mixture was shaken at ambient temperature for 2 hours. The reaction mixture was analyzed by LC/MS to confirm the formation of the desired product. The solvent was removed and the residue was purified by semi-preparative HPLC (Capcell Pak C18 column, 35 mm×20 mm, 5 micron particle size, 20 mL/min., gradient elution from 5–95% B in 10 mm., hold at 95% B for 2 mm., where A=0.1% trifluoroacetic acid/water and B=0.1% trifluoroacetic acid/acetonitrile, peak detection at 254 nm for triggering fraction collection). The semi-prep HPLC fractions were analyzed by LC-APCI/MS and the appropriate fractions were combined and lyophilized. The lyophilized material was purified a second time by semi-preparative HPLC using the same conditions except that the gradient elution from 5–95% B was run for 60 minutes instead of 10 minutes. The semi-prep HPLC fractions were analyzed by LC-APCI/MS and the appropriate fractions were combined and lyophilized to provide the trifluoroacetate salt of the desired amide.

EXAMPLE 216

N-[4-(4-Amino -2-(2-methoxyethyl)-1H-imidazo[4,5-c]quinolin-1-yl)butyl]-N-methyltrifluoromethanesulfonamide Trifluoroacetate

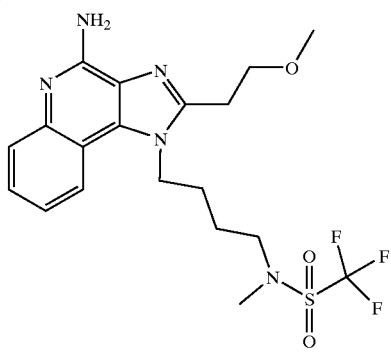

This compound was prepared using the general method of Example 215 above, except that trifluoromethanesulfonic anhydride was used in place of the sulfonyl chloride in Part A.

EXAMPLES 217–221

The examples in the table below were prepare using the following general method. The 1H-imidazo[4,5-c]quinolin-4-amine or the 6,7,8,9-tetrahydro-1H-imidazo[4,5-c]quinolin-4-amine (50 mg) was placed in a 2 dram (7.4 mL) vial. Dichloromethane (2 mL) and diisopropylethylamine (1.2 eq) were added. Dimethylsulfamoyl chloride (1.1 eq) was added. The vial was placed on a shaker for about 2–4 hours at ambient temperature. The reaction mixture was analyzed by LC/MS to confirm the formation of the desired product. The solvent was removed and the residue was purified by semi-preparative HPLC (Capcell Pak C18 column, 35 mm×20 mm, 5 micron particle size, 20 ml/min., gradient elution from 5–95% B in 10 mm., hold at 95% B for 2 mm., where A=0.1 % trifluoroacetic acid/water and B0.1 % trifluoroacetic acid/acetonitrile, peak detection at 254 nm for triggering fraction collection). The semi-prep HPLC fractions were analyzed by LC-APCI/MS and the appropriate fractions were combined and lyophilized to provide the trifluoroacetate salt of the desired sulfamide.

| Example # | Structure of the Free Base | APCI-MS m/e |
|---|---|---|
| 217 | (structure) | 393.1 |
| 218 | (structure) | 421.2 |
| 219 | (structure) | 483.3 |
| 220 | (structure) | 423.2 |
| 221 | (structure) | 425.1 |

EXAMPLES 222–228

The examples in the table below were prepared according to the synthetic method shown in Reaction Scheme V above.

1-(4-Aminobutyl)-2-(2-methoxyethyl)-1H-imidazo[4,5-c]quinolin-4-amine (50 mg) was placed in a 2 dram (7.4 mL) vial. 4-(Dimethylamino)pyridine (19 mg, 1.0 eq) and dichloromethane (800 µL) were added. The vial was sealed and cooled to −78° C. in a dry ice/acetone bath. Sulfuryl chloride (186 µL of 1 M in dichloromethane) was added. The vial was put on a shaker for about 30 minutes and then cooled back down to −78° C. A separate vial was charged with the amine of formula $R_4R_5NH$ (2.0 eq), triethylamine (2.0 eq) and dichloromethane (1 mL) and cooled to −78° C. (2.0 The amine/triethylamine solution was added to the first vial. The vial was placed on a shaker at ambient temperature for about 1 hour. The reaction mixture was analyzed by LC/MS to confirm the formation of the desired product. The solvent was removed and the residue was purified by semi-preparative HPLC (Capcell Pak C18 column, 35 mm×20 mm, 5 micron particle size, 20 mL/min., gradient elution from 5–95% B in 10 mm., hold at 95% B for 2 min., where A=0.1 % trifluoroacetic acid/water and B=0.1 % trifluoroacetic acid/acetonitrile, peak detection at 254 nm for triggering fraction collection). The semi-prep HPLC fractions were analyzed by LC-APCI/MS and the appropriate fractions were combined and lyophilized to provide the trifluoroacetate salt of the desired sulfamide.

| Example # | Structure of the Free Base | APCI-MS m/e |
|---|---|---|
| 222 | (structure) | 449.2 |
| 223 | (structure) | 475.3 |
| 224 | (structure) | 469.1 |
| 225 | (structure) | 490.2 |
| 226 | (structure) | 497.1 |
| 227 | (structure) | 533.2 |
| 228 | (structure) | 479.1 |

EXAMPLES 229–231

The examples in the table below were prepared using the method of Examples 222–228 above except that the amine of formula $R_4R_5NH$ was reacted with the sulfuryl chloride to provide the sulfamoyl chloride intermediate which was then reacted with 2.0 eq of 1-(4-aminobutyl)-2-(2-methoxyethyl)-1H-imidazo[4,5-c]quinolin-4-amine.

| Example # | Structure of the Free Base | APCI-MS m/e |
|---|---|---|
| 229 | | 447.1 |
| 230 | | 449.2 |
| 231 | | 483.2 |

CYTOKINE INDUCTION IN HUMAN CELLS

An in vitro human blood cell system was used to assess cytokine induction by compounds of the invention. Activity is based on the measurement of interferon and tumor necrosis factor (α) (IFN and TNF, respectively) secreted into culture media as described by Testerman et. al. In "Cytokine Induction by the Immunomodulators Imiquimod and S-27609", Journal of Leukocyte Biology, 58, 365–372 (September, 1995).

Blood Cell Preparation for Culture

Whole blood is collected by venipuncture into EDTA vacutainer tubes from healthy human donors. Peripheral blood mononuclear cells (PBMCs) are separated from whole blood by density gradient centrifugation using Histopaque®-1077 (Sigma Chemicals, St. Louis, Mo.). The PBMCs are suspended at 3–4×10$^6$ cells/mL in RPMI 1640 medium containing 10% fetal bovine serum, 2 mM L-glutamine and 1% penicillin/streptomycin solution (RPMI complete). The PBMC suspension is added to 48 well flat bottom sterile tissue culture plates (Costar, Cambridge, Mass. or Becton Dickinson Labware, Lincoln Park, N.J.) containing an equal volume of RPMI complete media containing test compound.

Compound Preparation

The compounds are solubilized in dimethyl sulfoxide (DMSO). The DMSO concentration should not exceed a final concentration of 1% for addition to the culture wells.

Incubation

The solution of test compound is added at 60 μM to the first well containing RPMI complete and serial (three fold or ten fold) dilutions are made. The PBMC suspension is then added to the wells in an equal volume, bringing the test compound concentrations to the desired range. The final concentration of PBMC suspension is 1.5–2×10$^6$ cells/mL. The plates are covered with sterile plastic lids, mixed gently and then incubated for 18 to 24 hours at 37° C. in a 5% carbon dioxide atmosphere.

Separation

Following incubation the plates are centrifuged for 5–10 minutes at 1000 rpm (~200×g) at 4° C. The cell culture supernatant is removed with a sterile polypropylene pipet and transferred to sterile polypropylene tubes. Samples are maintained at −30 to −70° C. until analysis. The samples are analyzed for interferon (α) and tumor necrosis factor (α) by ELISA Interferon (α) and Tumor Necrosis Factor (α) Analysis by ELISA Interferon (α) concentration is determined by ELISA using a Human Multi-Species kit from PBL Biomedical Laboratories, New Brunswick, N.J.

Tumor necrosis factor (α) (TNF)concentration is determined using ELISA kits available from Genzyme, Cambridge, Mass.; R&D Systems, Minneapolis, Minn.; or Pharmingen, San Diego, Calif.

The table below lists the lowest concentration found to induce interferon and the lowest concentration found to induce tumor necrosis factor for each compound. A "" indicates that no induction was seen at any of the tested concentrations (0.12, 0.37, 1.11, 3.33, 10 and 30 μM). A "*" indicates that no induction was seen at any of the tested concentrations (0.0001, 0.001, 0.01, 0.1, 1 and 10 μM).

Cytokine Induction in Human Cells

| Example Number | Lowest Effective Concentration (μM) | |
|---|---|---|
| | Interferon | Tumor Necrosis Factor |
| 1 | 0.12 | 3.33 |
| 2 | ** | ** |
| 3 | 0.01 | ** |
| 6 | 0.00017 | 1.11 |
| 7 | 0.01 | ** |
| 9 | 0.04 | ** |
| 11 | 0.01 | 1.11 |
| 13 | 10 | ** |
| 17 | 1.11 | 3.33 |
| 18 | 3.33 | ** |
| 19 | 0.12 | 3.33 |
| 20 | 0.12 | 3.33 |
| 21 | 1.11 | 30 |
| 22 | 0.37 | ** |

-continued

Cytokine Induction in Human Cells

| Example Number | Lowest Effective Concentration ($\mu$M) | |
|---|---|---|
| | Interferon | Tumor Necrosis Factor |
| 23 | 0.12 | 10 |
| 24 | 0.12 | 30 |
| 25 | 3.33 | ** |
| 26 | 10 | ** |
| 27 | 1.11 | 30 |
| 28 | 1.11 | 30 |
| 29 | 0.37 | 10 |
| 30 | 1.11 | ** |
| 31 | 1.11 | ** |
| 32 | 1.11 | ** |
| 33 | 1.11 | 10 |
| 34 | 0.04 | 0.37 |
| 35 | 1.11 | 10 |
| 36 | 0.0015 | 3.33 |
| 37 | 0.01 | 1.11 |
| 38 | 0.0015 | 0.37 |
| 40 | 0.0015 | 3.33 |
| 41 | 0.01 | ** |
| 42 | 0.01 | ** |
| 43 | 0.04 | ** |
| 44 | 0.0015 | 1.11 |
| 45 | 0.37 | ** |
| 46 | 0.37 | ** |
| 47 | 0.37 | ** |
| 48 | 0.37 | 10 |
| 50 | 0.12 | ** |
| 51 | 0.0015 | 0.37 |
| 52 | 0.12 | 10 |
| 53 | 0.01 | 3.33 |
| 54 | 10 | ** |
| 55 | 3.33 | ** |
| 56 | ** | ** |
| 57 | 3.33 | ** |
| 58 | 3.33 | ** |
| 59 | 3.33 | ** |
| 60 | ** | ** |
| 61 | 3.33 | ** |
| 62 | ** | ** |
| 63 | ** | ** |
| 64 | 3.33 | ** |
| 65 | 3.33 | ** |
| 66 | ** | 30 |
| 67 | 10 | ** |
| 68 | 10 | ** |
| 69 | 10 | ** |
| 70 | ** | ** |
| 71 | ** | 30 |
| 72 | 3.33 | ** |
| 73 | 0.001 | 0.1 |
| 74 | 0.001 | 0.01 |
| 75 | *** | *** |
| 76 | *** | *** |
| 77 | 0.001 | 1 |
| 78 | 0.001 | 0.1 |
| 79 | 0.01 | 1 |
| 80 | 1 | 10 |
| 81 | 0.001 | 1 |
| 82 | 0.001 | 1 |
| 83 | 0.001 | 1 |
| 84 | 1 | 10 |
| 85 | 1 | *** |
| 86 | 0.01 | 1 |
| 87 | 0.001 | 1 |
| 88 | 0.01 | 1 |
| 89 | 0.001 | 1 |
| 90 | 0.01 | 1 |
| 91 | 0.01 | 1 |
| 92 | 0.1 | 10 |
| 93 | 0.001 | 0.1 |
| 94 | 0.001 | 1 |
| 95 | 0.001 | 1 |
| 96 | 1 | *** |
| 97 | 0.1 | 10 |
| 98 | 1 | *** |
| 99 | 0.1 | 10 |
| 100 | 0.01 | 10 |
| 101 | 0.01 | 10 |
| 102 | 0.001 | 10 |
| 103 | 0.1 | 10 |
| 104 | 0.01 | *** |
| 105 | 1 | 10 |
| 106 | 1 | 1 |
| 107 | 1 | *** |
| 108 | 0.1 | 10 |
| 109 | 1 | 10 |
| 110 | 10 | *** |
| 111 | 0.001 | 10 |
| 112 | 0.0001 | *** |
| 113 | 0.0001 | *** |
| 114 | 0.01 | *** |
| 116 | 0.001 | 1 |
| 117 | 0.0001 | 1 |
| 120 | 0.0001 | 1 |
| 121 | 0.0001 | 10 |
| 122 | 0.0001 | 1 |
| 123 | 0.0001 | 10 |
| 127 | 0.0001 | 10 |
| 128 | 0.0001 | 1 |
| 131 | 0.0001 | 1 |
| 138 | 0.0001 | 10 |
| 148 | 0.0001 | 1 |
| 152 | 0.0001 | 10 |
| 154 | 0.001 | 10 |
| 158 | 0.0001 | 1 |
| 159 | 0.0001 | 0.1 |
| 160 | 0.001 | 1 |
| 161 | 0.01 | 10 |
| 184 | 0.0001 | 1 |
| 200 | 0.01 | 0.1 |
| 202 | 0.0001 | 1 |
| 203 | 0.0001 | 1 |
| 204 | 0.0001 | 1 |
| 205 | 0.0001 | 1 |
| 206 | 1 | *** |
| 207 | 0.001 | 1 |
| 208 | 0.0001 | 1 |
| 209 | 0.0001 | 0.1 |
| 210 | 0.0001 | 1 |
| 211 | 0.0001 | 1 |
| 212 | 0.0001 | 0.01 |
| 213 | 0.0001 | 1 |
| 214 | 0.01 | 10 |
| 215 | 0.01 | 1 |
| 217 | 1 | *** |
| 218 | 0.0001 | 1 |
| 220 | 0.0001 | 1 |
| 221 | 0.0001 | 1 |
| 224 | 0.0001 | 10 |
| 226 | 0.0001 | 0.1 |
| 227 | 0.001 | *** |
| 229 | 0.0001 | 0.1 |
| 230 | 0.0001 | 1 |
| 231 | 0.0001 | 1 |

EXAMPLE 1-PD

Treatment of Mice with an IRM

Studies in mice infected with bacteria known to cause periodontitis were performed to determine the potential utility of the IRM compounds in this disease.

Preparation and Maintenance of Bacterial Cultures

An isolate of *Porphyromonas gingivalis* from the subgingival pocket of a patient with adult periodontitis and noninsulin dependent diabetes was used. The isolate is deposited with American Type Culture Collection, 10801 University Blvd., Manassas, Va. 20110–2209 USA as ATCC Accession No.53977 (strain A7A1-28). The organisms were propagated in an anaerobic jar (Becton Dickinson Microbiology Systems, Cockeysville, Md.) under an atmosphere of 5% $CO_2$ 10% $H_2$ and 85% $N_2$ at 37° C. on PRAS (prereduced anaerobically sterilized) Brucella agar plates (Anaerobe Systems, Morgan Hill, Calif.). Broth cultures were grown in BHTS media, a 50% mixture of Tripticase Soy and Brain Heart Infusion broth supplemented with 5% Yeast Extract (all from Becton Dickinson Microbiology Systems), 10 µg/L hemin, 1 µg/L metadione and 5% horse serum (Sigma Chemical, St. Louis. Mo.). Species were maintained by weekly transfer on plates. Frozen stocks were made by re-suspending log-phase cultures in 15% glycerol in BHTS and maintaining at −70° C. for several months.

Oral Infection of Mice with *Porphyromonas gingivalis*

90 conventional BALB/c specific pathogen-free mice (Charles River Labs, Wilmington, Mass.) were divided into three groups of about 30 mice per group. As shown in Table 1, Groups II and III, but not I, were infected with *P. gingivalis* as described below. Groups I and II were administered an IRM compound as described below.

TABLE 1

Experimental Protocol

| Group/Treatment | Infected with *P.gingivalis* |
|---|---|
| I/IRM | NO |
| II/IRM | YES |
| III/NONE | YES |

All mice were kept in an animal colony, where they were caged away from other animals. All mice were kept on a 12-hour light/dark cycle and received distilled water ad libitum. Mice within experiments were sex- and age-matched (12–18 weeks at the start of various experiments).

The mice in Groups I–III were given sulphamethoxazole/trimethoprim, 10 ml per pint in deionized water, ad libitum for 10 days before experimentation, followed by 4 days without antibiotics. The mice of Groups II–III were then infected by gavage with $10^9$ colony-forming units of live *P. gingivalis*, in 100 µl of phosphate buffered saline (PBS) with 2% carboxymethylcellulose, three times at 2 to 4 day intervals as described in Klausen et al, "Two complementary methods of assessing periodontal bone level in rats", *Scandinavian Journal of Dental Research,*97, 494–9 (1989).

Figure 2:
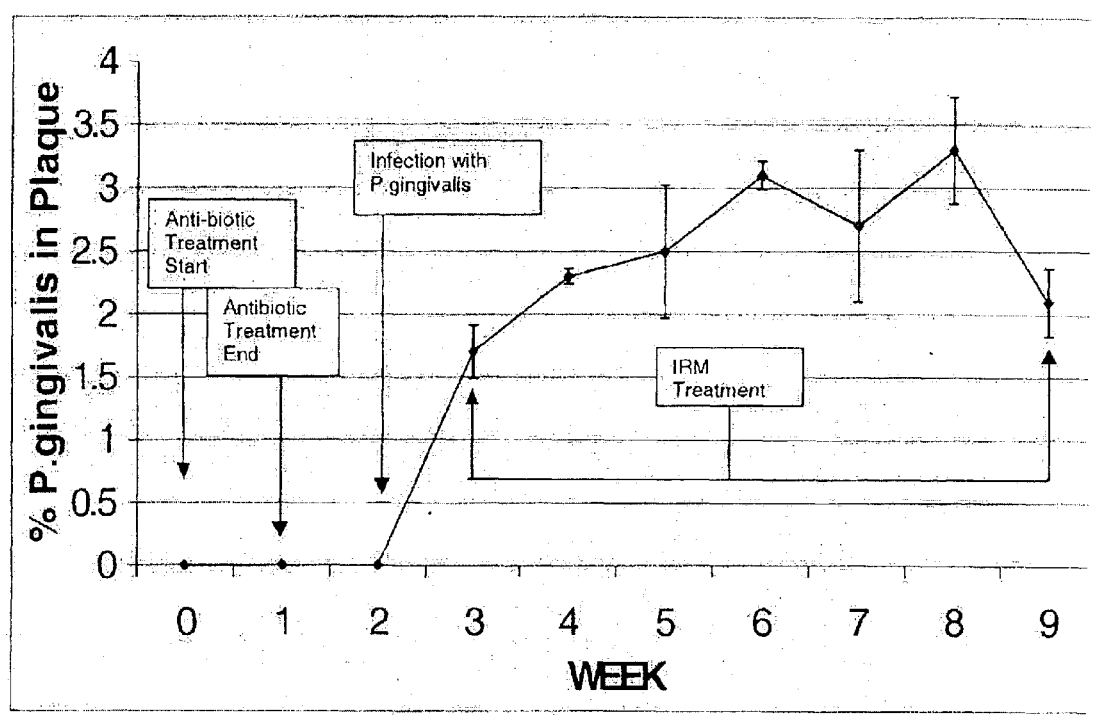
FIG. 2 is a graph showing the proportion of *Porphyromonas gingivalis* in the plaque of infected mice.

As shown in FIG. 2, two weeks prior to infection there was no evidence of *P. gingivalis* in any of the subject animals, a result that continued up to infection. The proportion of *P. gingivalis* in samples collected the first week after infection reached about 2%. See below. It remained between 2% and 5% during the remainder of the experiment. There was no significant difference between the levels of *P. gingivalis* in the IRM treated or untreated animals at any point in the experiment.

Bacterial Isolation from Plague of Infected Mice

Subgingival plaque samples were obtained from the molars of mice from all three groups using sterile fine paper points (Johnson and Johnson Dental Products Co. East Windsor, N.J.). The points were placed in 1 ml of water that was then tested for total bacteria and *P. gingivalis* levels by quantitative PCR similar to that described for *Bacteroides forsythus* in Shelburne et al, "Quantitation of *Bacteroides forsythus* in subgingival plaque: comparison of immunoassay and quantitative polymerase chain reaction", *J. Microbial. Methods,* 39:97–107 (2000).

Treatment with Resiquimod

The mice of Groups I and II were dosed by oral gavage twice weekly for seven weeks with either 1 mg/kg or 0.1 mg/kg of resiquimod (4-amino-2-ethoxymethyl-αα-dimethyl-1H-imidazo[4,5-c]quinoline-1-ethanol) in 100 µl of PBS. Animals were sacrificed at 43 days after treatment began.

Measurement of Alveolar Bone Loss

Bone loss around the maxillary molars was assessed by a morphometric method developed for studies of bone loss in mice. Baker P. J., et al., "Oral infection with *Porphyromonas gingivalis* and induced alveolar bone loss in immunocompetent and severe combined immunodeficient mice,"*Arch. Oral Biol.,* 39(12):1035–40 (December 1994). Jaws were de-fleshed after a 5-minute treatment in boiling water at 15 p.s.i. (1.05 Kg/cm$^2$), immersed overnight in 3% hydrogen peroxide, air-dried and stained with 1% methylene blue. The bone level, that is, the distance from the cemento-enamel junction (CEJ) to the alveolar bone crest on the maxillary molars, was measured under a dissecting microscope (×30). 14 measurements of he bone level were made per mouse. All measurements of bone level were done three times in a random fashion. Values for horizontal bone levels in µm per site were generated by computer analysis of calibrated lines from the CEJ to the alveolar bone crest image acquired by video camera.

Results

Figure 3:
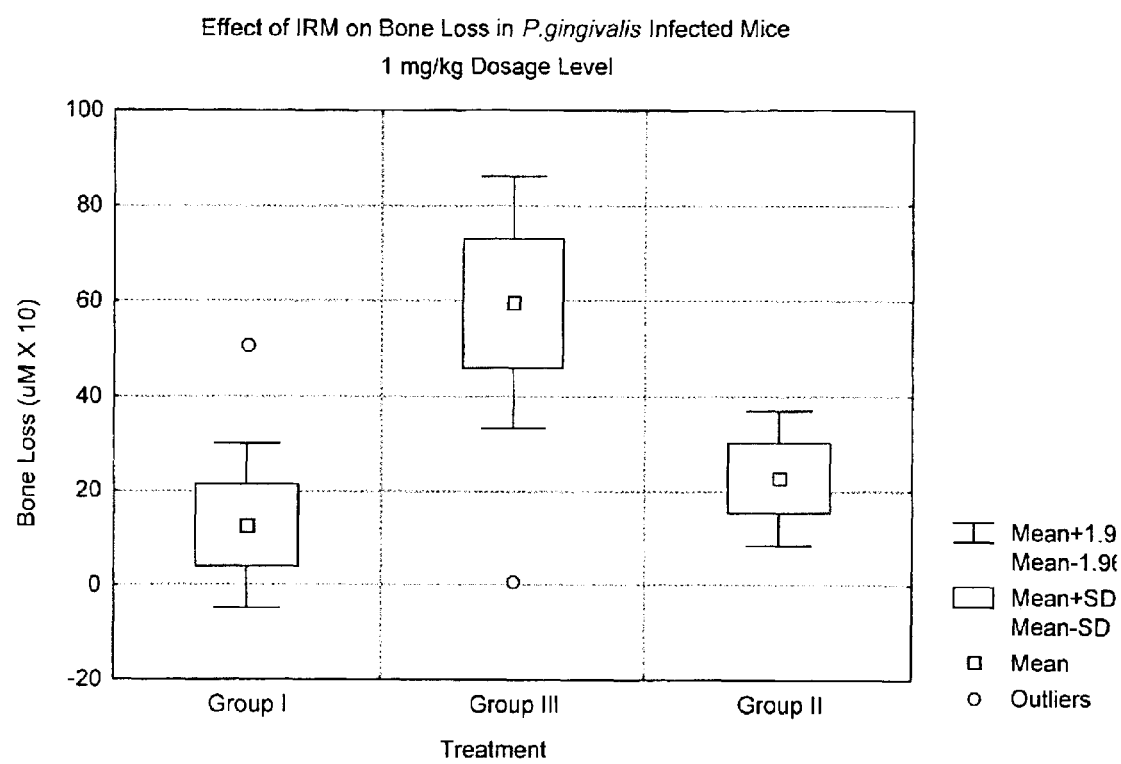
FIG. 3 is a graph showing bone loss in infected mice.

In animals treated with resiquimod there was substantially less bone loss than in untreated animals (FIG. 3), and the difference was significant at a level appropriate for this model (p<0.01). There was no difference between the animals treated with 1 mg/kg doses of resiquimod and those treated with 0.1 mg/kg.

Interestingly, there was no reduction in the levels of *P. gingivalis* in the plaque of the subject animals that correlated with the difference in bone loss or the treatment (or non-treatment) of the mice. This indicates that the reduction in bone loss is due to modification of some host response, not the elimination of the bacteria, although they are clearly required to initiate the disease.

EXAMPLE 2-PD

Treatment of Naturally Occurring Periodontal Disease in a Dog with an IRM Gel Compostion One dog with naturally occurring periodontal disease was identified by clinical signs including Gingival Index (scored 0–3 by observation), Bleeding Index (scored 0–3 by observation, and Probing Depth (measured to the nearest mm using a North Carolina Probe). The animal was treated with a gel composition containing resiquimod, prepared as described below, in addition to the standard treatment of scaling and root planing. Therapeutic efficacy was determined by a trained examiner measuring the aforementioned indicies around the affected teeth.

Preparation of IRM Gel Composition Containing the IRM Resiquimod

Propylene glycol (700 g) and the IRM resiquimod (4-amino-2-ethoxymethyl-αα-dimethyl-1H-imidazo[4,5-c] quinoline-1-ethanol, 7.0 g) were added to a 1000 mL glass beaker. The resulting mixture was heated (about 56° C.) with stirring until all of the resiquimod was dissolved. The resulting solution was added to the mixing bowl of a ROSS LDM-4 mixer. Triacetin (11,963.0 g) was added to the mixing bowl and the resulting mixture was mixed for 10 minutes at 36 rpm. Colloidal silicon dioxide (1,330.0 g, AEROSIL® 200 from Degussa, Frankfurt, Germany) was added in five parts. After each addition the resulting mixture was mixed at ambient pressure for 1 to 2 minutes at 36 rpm and then under vacuum (about 18 in Hg; $4.0 \times 10^4$ Pa) for about 9 minutes at 36 rpm. The sides of the mixing bowl and the mixing blades were scraped. The formulation was mixed under vacuum (about 17 in Hg; $4.3 \times 10^4$ Pa) for about 10 minutes at 36 rpm. The resulting gel contained 0.05% resiquimod, 5.0% propylene glycol, 9.5% colloidal silicon dioxide, and 85.45% triacetin.

Treatment with an IRM Gel Composition

The animal was sedated with xylazine at a dose of about 1 mg/kg and its teeth cleaned of supragingival and subgingival plaque. The teeth affected by periodontitis were scaled and root planed to remove plaque and calculus from both supragingival (enamel) and subgingival (root) tooth surfaces using an ultrasonic Cavitron®(Dentsply, York, Pa.) and curets. The Cavitron was used to remove gross debris and the curets were used to smooth the root surface. A clean, smooth root surface resulting from the root planing allows epithelial and connective tissue attachment to the root surface during the healing process.

During the scaling procedure, there was no deliberate attempt to remove tooth substance along with the calculus. Root planing was performed to remove residual embedded calculus and portions of cementum from the roots of the teeth to produce a smooth, hard, clean surface. The primary objective of scaling and root planing is to restore gingival health by completely removing material from the tooth surface that provokes gingival inflammation; that is, plaque, calculus and altered cementum. Scaling and root planing were not done as separate procedures in this Example. The difference between scaling and root planing is only a matter of degree. The nature of the tooth surface determines the degree to which the root surface is scaled or planed.

Depending on the size of the periodontitis lesion, about 10–50 μl of the resiquimod gel composition prepared as described above was applied to sites affected by periodontitis. The composition was placed in the periodontal pocket adjacent to each site using a blunt 27 ga. needle and syringe filled with the composition. In this example a single application of the gel was used.

After treatment the animal was treated with yohimbine at about 0.1 mg/kg to reverse the sedation and the animal was returned to its cage.

Clinical Measurements

The pockets were examined at weekly intervals for the indicies measured at the time of treatment. Measurement of attachment loss was performed using a standard North Carolina Periodontal probe marked at 1 mm intervals. The probe, which is about 1 mm in diameter was inserted into the periodontal pocket to the base. The depth of the pocket (PD) was noted and the probe was withdrawn. The depth of the probe was noted at this time. At the same time the gingival index (GI) a measure of the redness of the gingival tissue (0=no redness to 3=very red, distended) was noted along with the bleeding index (BI) which is a measurement of the tendency of the pocket to bleed upon probing (0=no bleeding to 3=substantial bleeding). These are all standard measurements in dental practice for the evaluation of human periodontal disease.

Results

Figure 4A:
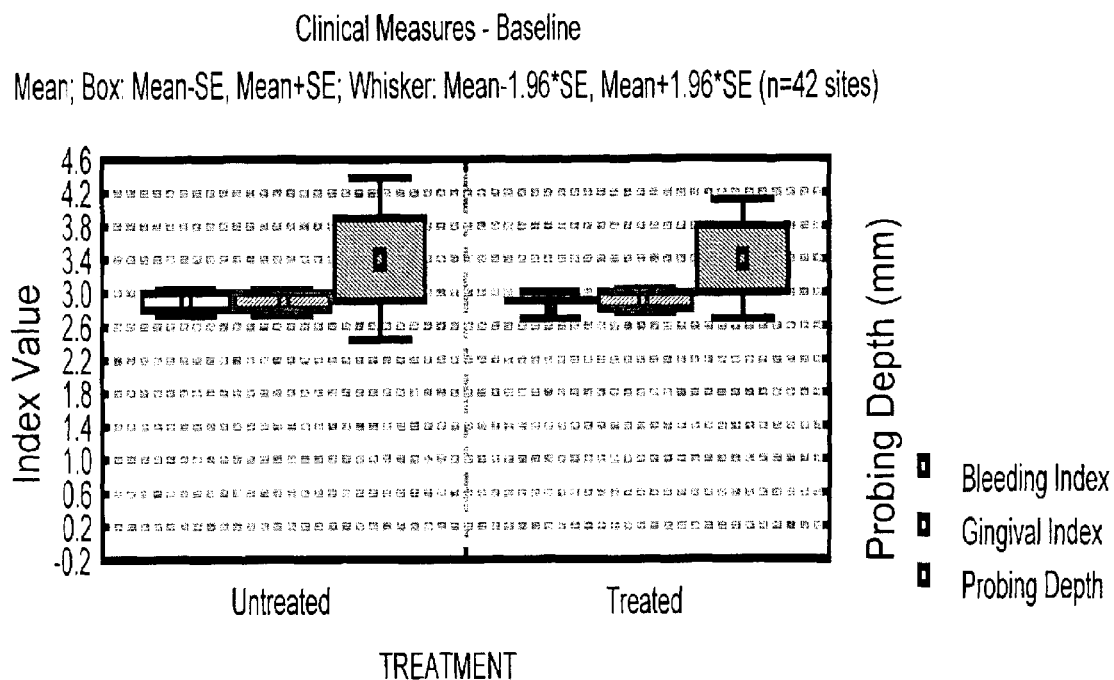
FIG. 4a is a graph of bleeding index, gingival index and probing depth of a dog pre-treatment.
Figure 4B:
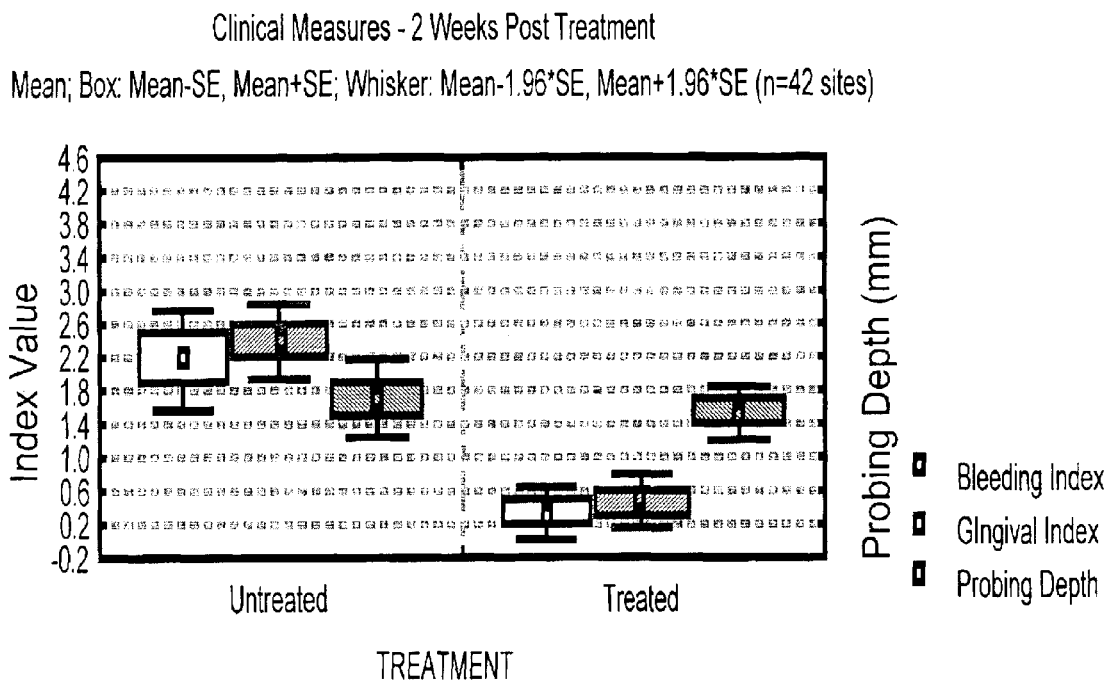
FIG. 4b is a graph of bleeding index, gingival index and probing depth of a dog at two weeks post-treatment.

Referring to FIGS. 4a and 4b, there was an over all improvement in PD, BI and GI as a result of the mechanical cleaning of the teeth (compare left hand panels of Baseline graph (FIG. 4a) and 2 Week Post-Treatment graph (FIG. 4b). There was improvement in the BI and GI of the treated sites compared to untreated sites that is statistically significant (p<0.01). (Compare left and right panels of the 2 Week Post-Treatment graph, FIG. 4b). This is due to the IRM treatment.

There was no significant difference in the PD of the treated compared to untreated sites (compare left and right panels of 2 Week Post-Treatment graph, FIG. 4b). The inventors believe this is due to two-weeks being an insufficient time post-treatment for rebuilding the tooth attachment cellular apparatus.

The study was not a terminal study and thus bone loss was not determined

EXAMPLE 3-PD

Treatment of Chronic Adult Periodontal Disease in a Human Patient with an IRM Containing Transmucosal Patch A human patient affected with chronic adult periodontal disease can be identified by clinical signs typically including BI, GI, Probing Depth. The human can be treated with a transmucosal patch containing an IRM, prepared as described in Example 4 below, in addition to the standard treatment of scaling and root planing.

The patient's teeth can be cleaned of supragingival plaque. The teeth affected by periodontitis can be scaled and root planed to remove plaque and calculus from both supragingival and subgingival tooth surfaces using known instruments, such as, for example, an ultrasonic Cavitron and curets. The Cavitron is used to remove gross debris and the curets are used to smooth the root surface Depending on the size of the periodontitis lesion, a transmucosal patch containing about 0.05–1.0% of IRM per patch, and prepared, for example, as described in Example A-PD below, can be adhered to the patient's gingiva proximate the sites affected by periodontitis. The transmucosal patches can remain adhered to the gingiva for about 1–24 hours. In a typical situation the patch will remain adhered for about 1–3 hours. The patches can be applied two times a week for three weeks. The patient can be reexamined at 1 month after completion of treatment and at three month intervals thereafter. Treatment can be repeated as necessary.

EXAMPLE 4-PD

Preparation of a Transmucosal Patch Containing the IRM 4-amino-2-ethoxymethyl-α,α-dimethyl-1H-imidazo[4,5-c]quinoline-1-ethanol A transmucosal patch suitable for gingival application was prepared containing the IRM compound 4-amino-2-ethoxymethyl-α,α-dimethyl-1H-imidazo[4,5-c]quinoline-1-ethanol (resiquimod).

Isooctyl acrylate (20.03 g), acrylic acid (19.98 g), methoxy polyethylene glycol 550 monomethacrylate (19.07 g), polyethylene glycol 400 diacrylate (0.72 g), polyacrylic acid (5.73 g of a solution containing 17.5% by weight of polyacrylic acid in water), polyoxyethylene 10 oleyl ether (21.78 g of Brij® 97), propylene glycol (10.00), water (2.89 g), resiquimod (0.10 g) and 2-hydroxy-1-(4-(2-hydroxyethoxy) phenyl)-2-methyl-1-propanone (0.55 g of Irgacure® 2959) were combined in a glass jar and then mixed on a platform shaker until a clear liquid composition was obtained. The composition contained 0.10% by weight of resiquimod.

The liquid was knife coated at a wet thickness of 25 mil (635 μM) onto the non-woven polypropylene side of a trilaminate backing and the exposed surface was covered with a clear polyester (1.5 mil, 38 μM) silicone coated release liner. The coated composition was then exposed to UVA light for 8 minutes so that the composition was exposed to a total energy of 2677 mJ/cm². The release liner was removed and the exposed surface of the cured composition was laminated to a silicone coated polyester release liner (5 mil, 127 μM). Patches (2.05 cm²) were cut from the laminate.

The present invention has been described with reference to several embodiments thereof. The foregoing detailed description and examples have been provided for clarity of understanding only, and no unnecessary limitations are to be understood therefrom. It will be apparent to those skilled in the art that many changes can be made to the described embodiments without departing from the spirit and scope of the invention. Thus, the scope of the invention should not be limited to the exact details of the compositions and structures described herein, but rather by the language of the claims that follow.

From the foregoing detailed description and examples, it will be evident that modifications and variations can be made in the methods of the invention without departing from the spirit or scope of the invention. Therefore, it is intended that all modifications and variations not departing from the spirit of the invention come within the scope of the claims and their equivalents.

What is claimed is:

1. A compound of Formula I:

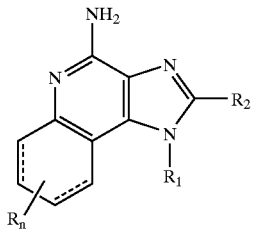

(I)

wherein
$R_1$ is -alkyl-$NR_3$—$SO_2$—X—$R_4$;
$R_2$ is selected from the group consisting of:
-alkyl;
-alkyl-O-alkyl;
$R_3$ is hydrogen;
$R_4$ is alkyl;
X is a bond; and
n is 0;
or a pharmaceutically acceptable salt thereof.

* * * * *

UNITED STATES PATENT AND TRADEMARK OFFICE
CERTIFICATE OF CORRECTION

PATENT NO. : 6,825,350 B2
APPLICATION NO. : 10/166321
DATED : November 30, 2004
INVENTOR(S) : Stephen L. Crooks It is certified that error appears in the above-identified patent and that said Letters Patent is hereby corrected as shown below:

Title page,
Foreign Patent Documents, last JP reference, Delete ""2002-247884" and insert -- 2000-247884 --, therefore;
Other Publications, "Wozniak" reference, Delete "Animation" and insert -- Amination --, both times;

Column 1,
Line 45, After "J" Insert -- . --;

Column 4,
Line 16, After/below "-S(O)$_{0-2}$-alkyl;" insert -- -S(O)$_{0-2}$-(alkyl)$_{0-1}$-aryl; --;
Line 20, Delete "-S(O)$_{0-2}$(alkyl)$_{0-1}$-heterocyclyl;" and insert -- -S(O)$_{0-2}$(alkyl)$_{0-1}$-heterocyclyl; --, therefor;

Column 6,
Line 18, Delete "benezenesulfonyl" and insert -- benzenesulfonyl --, therefore;
Line 20-21, Delete "animating" and insert -- aminating --, therefore;
Line 22, Delete "animonium" and insert -- ammonium --, therefore;
Line 23, Delete "animonium" and insert -- ammonium --, therefore;

Column 7,
Line 51, Delete "Scheme m" and insert -- Scheme III --, therefore;
Line 54, Delete "Scheme HI" and insert -- Scheme III --, therefore;

Column 9,
Line 24-25, Delete "Formula XLV" and insert -- Formula XIV --, therefore;
Reaction Scheme V, Structure VIII, Delete " 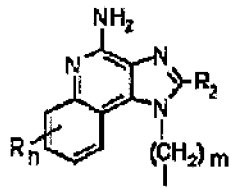 " and insert -- 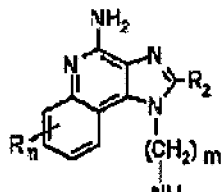 -- therefore;

Column 11,
Line 33, Delete "[14,5-c]" and insert -- [4,5-c] --, therefore;

Column 13,
Line 49, Delete "nitric" and insert -- nitrile --, therefore;

UNITED STATES PATENT AND TRADEMARK OFFICE
CERTIFICATE OF CORRECTION

PATENT NO. : 6,825,350 B2
APPLICATION NO. : 10/166321
DATED : November 30, 2004
INVENTOR(S) : Stephen L. Crooks It is certified that error appears in the above-identified patent and that said Letters Patent is hereby corrected as shown below:

Column 15,
Line 18, After "thrombocythaemia" insert -- ; --;
Line 50, Delete "100μg/kg" and insert -- 10μg/kg --, therefore;

Column 16,
Line 66, After "(1996)" insert -- . --;

Column 20,
Line 1, Delete "60° C." and insert -- 60° C --, therefore;
Line 2, Delete "30° C." and insert -- 30° C --, therefore;
Line 3, Delete "naphthaleneslfonyl" and insert -- naphthalenesulfonyl --, therefore;
Line 6, Delete "60° C." and insert -- 60° C --, therefore;
Line 10, Delete "N$^1$-(4-(4" and insert -- N$^1$-[4-(4 --, therefore;
Line 48, Delete "vacua" and insert -- vacuo --, therefore;
Line 52, Delete "(MgSO$_4$," and insert -- (MgSO$_4$), --, therefore;
Line 66, After "57.74; H" insert -- , --;

Column 21,
Line 3, Delete "phenylmethanesulfonainide" and insert
        -- phenylmethanesulfonamide --, therefore;

Column 22,
Line 19, Delete "C$_{21}$H$_{29}$N$_5$O$_2$S" and insert -- C$_{24}$H$_{29}$N$_5$O$_2$S --, therefore;
Line 20, After "C$_{24}$H$_{29}$N$_5$O$_2$S" insert -- : --;
Line 26, Delete "N$^1$-[4" and insert -- N-[4 --, therefore;
Line 47, Delete "4amine" and insert -- 4-amine --, therefore;
Line 50, Delete "dichioroinethane" and insert -- dichloromethane --, therefore;
Line 62, After "(m, 7H)" insert -- , --;

Column 23,
Line 37, After "(m, 2H)" insert -- , --;

Column 24,
Line 1, After "solution" insert -- of --;
Line 8, Delete "vacua" and insert -- vacuo --, therefore;
Line 53, Delete "combine" and insert -- combined --, therefore;
Line 65, Delete "C$_{24}$H$_{28}$N$_6$O$_4$" and insert -- C$_{24}$H$_{28}$N$_6$O$_4$S --, therefore;

Column 25,
Line 34, Delete "4amino" and insert -- 4-amino --, therefore;

UNITED STATES PATENT AND TRADEMARK OFFICE
CERTIFICATE OF CORRECTION

PATENT NO. : 6,825,350 B2  
APPLICATION NO. : 10/166321  
DATED : November 30, 2004  
INVENTOR(S) : Stephen L. Crooks Page 3 of 5

It is certified that error appears in the above-identified patent and that said Letters Patent is hereby corrected as shown below:

Column 26,
Line 12, Delete "vacua" and insert -- vacuo --, therefore;
Line 63, Delete "J=8.3." and insert -- J=8.3, --, therefore;

Column 27,
Line 29, Delete "vacua" and insert -- vacuo --, therefore;
Line 32, Delete "25 mm" and insert -- 25 min --, therefore;
Line 33, Delete "5 mm" and insert -- 5 min --, therefore;
Line 42, Delete "vacua" and insert -- vacuo --, therefore;

Column 29,
Line 16, Delete "2phenyl" and insert -- 2-phenyl --, therefore;
Line 41, Delete "animonium" and insert -- ammonium --, therefore;
Line 43, Delete "N-hydrochloric" and insert -- N hydrochloric --, therefore;
Line 57, Delete "40° C" and insert -- 4° C --, therefore;

Column 30,
Line 61, Delete "10 mm" and insert -- 10 min --, therefore;
Line 62, Delete "2 mm" and insert -- 2 min --, therefore;

Column 35,
Line 30, Delete "254 run" and insert -- 254 nm --, therefore;

Column 36,
Line 61, Delete "10 mm" and insert -- 10 min --, therefore; and Delete
 "2 mm" and insert --2 min --, therefore;

Column 40,
Line 2, Delete "N-[2" and insert -- N-[4 --, therefore;
Line 3, Delete "trifluoromethanesulfamide" and insert
 -- trifluoromethanesulfonamide --, therefore;
Line 33, Delete "4amine" and insert -- 4-amine --, therefore;
Line 51, Delete "4-amino" and insert -- 4-amine --, therefore and Delete
 "2 drain (7.4 ml)" and insert -- 2 dram (7.4 mL) --, therefore;
Line 52, Delete "Diisopropylethylaniine" and insert
 -- Diisopropylethylamine --, therefore;
Line 61, Delete "10 mm" and insert -- 10 min --, therefore;

UNITED STATES PATENT AND TRADEMARK OFFICE
CERTIFICATE OF CORRECTION

PATENT NO. : 6,825,350 B2
APPLICATION NO. : 10/166321
DATED : November 30, 2004
INVENTOR(S) : Stephen L. Crooks It is certified that error appears in the above-identified patent and that said Letters Patent is hereby corrected as shown below:

Column 50,
Line 36, Delete "10 mm" and insert -- 10 min --, therefore;
Line 37, Delete "2 mm" and insert -- 2 min --, therefore;

Column 127,
Line 41, Delete "animonium" and insert -- ammonium --, therefore;

Column 135,
Line 28, Delete "Trifluoroacetat" and insert -- Trifluoroacetate --, therefore;

Column 136,
Line 37, Delete "10 mm" and insert -- 10 min --, therefore;
Line 38, Delete "2 mm" and insert -- 2 min --, therefore;

Column 137,
Line 20, Delete "20 ml/min" and insert -- 20 mL/min --, therefore;
Line 21, Delete "10 mm" and insert -- 10 min --, therefore;
Line 22, Delete "2 mm" and insert -- 2 min --, and Delete "B0.1" and insert -- B=0.1 --. therefore;

Column 138,
Line 53, After "-78° C." delete "(2.0";
Line 61, Delete "10 mm" and insert -- 10 min --, therefore;

Column 146,
Line 7, Delete "-αα-" and insert -- -α,α- --, therefore;
Line 24, Delete "he" and insert -- the --, therefore;
Line 48, Delete "Compostion" and insert -- Composition --, therefore;
Line 62, Delete "-αα-" and insert -- -α,α- --, therefore;

UNITED STATES PATENT AND TRADEMARK OFFICE
CERTIFICATE OF CORRECTION

PATENT NO. : 6,825,350 B2
APPLICATION NO. : 10/166321
DATED : November 30, 2004
INVENTOR(S) : Stephen L. Crooks It is certified that error appears in the above-identified patent and that said Letters Patent is hereby corrected as shown below:

Column 148,
Line 37, Delete "A-PD" and insert -- 4-PD --, therefore;
Line 38, Delete "sites" and insert -- site --, therefore.

Signed and Sealed this

Twenty-second Day of May, 2007

JON W. DUDAS
*Director of the United States Patent and Trademark Office*

UNITED STATES PATENT AND TRADEMARK OFFICE
CERTIFICATE OF CORRECTION

PATENT NO. : 6,825,350 B2
APPLICATION NO. : 10/166321
DATED : November 30, 2004
INVENTOR(S) : Stephen L. Crooks It is certified that error appears in the above-identified patent and that said Letters Patent is hereby corrected as shown below:

Title page,
Foreign Patent Documents, last JP reference, Delete "2002-247884" and insert
-- 2000-247884 --, therefore;
Other Publications, "Wozniak" reference, Delete "Animation" and insert
-- Amination --, both times;

Column 1,
Line 45, After "J" insert -- . --;

Column 4,
Line 16, After/below "-S(O)$_{0-2}$-alkyl;" insert -- -S(O)$_{0-2}$–(alkyl)$_{0-1}$-aryl; --;
Line 20, Delete "-S(O)$_{0-2}$(alkyl)$_{0-1}$-heterocyclyl; and insert
-- -S(O)$_{0-2}$–(alkyl)$_{0-1}$-heterocyclyl; --, therefor ;

Column 6,
Line 18, Delete "benezenesulfonyl" and insert -- benzenesulfonyl --, therefore;
Line 20-21, Delete "animating" and insert -- aminating --, therefore;
Line 22, Delete "animonium" and insert -- ammonium --, therefore;
Line 23, Delete "animonium" and insert -- ammonium --, therefore;

Column 7,
Line 51, Delete "Scheme m" and insert -- Scheme III --, therefore;
Line 54, Delete "Scheme HI" and insert -- Scheme III --, therefore;

Column 9,
Line 24-25, Delete "Formula XLV" and insert -- Formula XIV --, therefore;
Reaction Scheme V, Structure VIII,

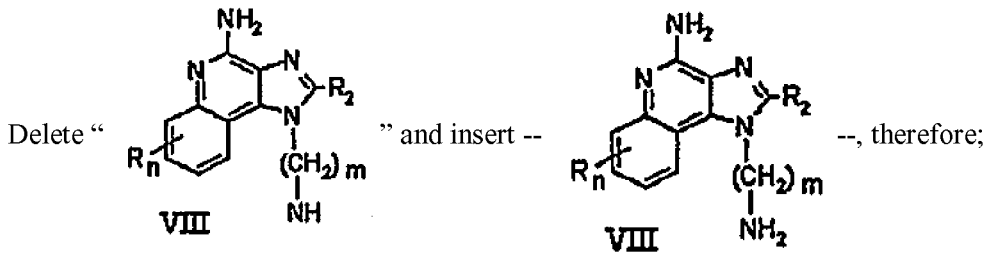

Column 11,
Line 33, Delete "[14,5-c]" and insert -- [4,5-c] --, therefore;

Column 13,
Line 49, Delete "nitric" and insert -- nitrile --, therefore;

UNITED STATES PATENT AND TRADEMARK OFFICE
CERTIFICATE OF CORRECTION

PATENT NO. : 6,825,350 B2
APPLICATION NO. : 10/166321
DATED : November 30, 2004
INVENTOR(S) : Stephen L. Crooks It is certified that error appears in the above-identified patent and that said Letters Patent is hereby corrected as shown below:

Column 15,
Line 18, After "thrombocythaemia" insert -- ; --;
Line 50, Delete "100µg/kg" and insert --10µg/kg --, therefore;

Column 16,
Line 66, After "(1996)" insert -- . --;

Column 20,
Line 1, Delete "60° C." and insert -- 60° C --, therefore;
Line 2, Delete "30° C." and insert -- 30° C --, therefore;
Line 3, Delete "naphthaleneslfonyl" and insert -- naphthalenesulfonyl --, therefore;
Line 6, Delete "60° C." and insert -- 60° C --, therefore;
Line 10, Delete "$N^1$-(4-(4" and insert -- $N^1$-[4-(4 --, therefore;
Line 46, Delete "vacua" and insert -- vacuo --, therefore;
Line 52, Delete "(MgSO₄," and insert -- (MgSO₄), --, therefore;
Line 66, After "57.74; H" insert -- , -- ;

Column 21,
Line 3, Delete "phenylmethanesulfonainide" and insert
-- phenylmethanesulfonamide --, therefore;

Column 22,
Line 19, Delete "$C_{21}H_{29}N_5O_2S$" and insert -- $C_{24}H_{29}N_5O_2S$ --, therefore;
Line 20, After "$C_{24}H_{29}N_5O_2S$" insert -- : --;
Line 26, Delete "$N^1$-[4" and insert -- N-[4 --, therefore;
Line 47, Delete "4amine" and insert -- 4-amine --, therefore;
Line 50, Delete "dichioroinethane" and insert -- dichloromethane --, therefore;
Line 62, After "(m, 7H)" insert -- , --;

Column 23,
Line 37, After "(m, 2H)" insert -- , --;

UNITED STATES PATENT AND TRADEMARK OFFICE
CERTIFICATE OF CORRECTION

PATENT NO. : 6,825,350 B2
APPLICATION NO. : 10/166321
DATED : November 30, 2004
INVENTOR(S) : Stephen L. Crooks It is certified that error appears in the above-identified patent and that said Letters Patent is hereby corrected as shown below:

Column 24,
Line 1, After "solution" insert -- of --;
Line 8, Delete "vacua" and insert -- vacuo --, therefore;
Line 53, Delete "combine" and insert -- combined --, therefore;
Line 65, Delete "$C_{24}H_{28}N_6O_4$" and insert -- $C_{24}H_{28}N_6O_4S$ --, therefore;

Column 25,
Line 34, Delete "4amino" and insert -- 4-amino --, therefore;

Column 26,
Line 12, Delete "vacua" and insert -- vacuo --, therefore;
Line 63, Delete "J=8.3." and insert -- J=8.3, --, therefore;

Column 27,
Line 29, Delete "vacua" and insert -- vacuo --, therefore;
Line 32, Delete "25 mm" and insert -- 25 min --, therefore;
Line 33, Delete "5 mm" and insert -- 5 min --, therefore;
Line 42, Delete "vacua" and insert -- vacuo --, therefore;

Column 29,
Line 16, Delete "2phenyl" and insert -- 2-phenyl --, therefore;
Line 41, Delete "animonium" and insert -- ammonium --, therefore;
Line 43, Delete "N-hydrochloric" and insert -- N hydrochloric therefore;
Line 57, Delete "40° C" and insert -- 4° C --, therefore;

Column 30,
Line 61, Delete "10 mm" and insert -- 10 min --, therefore;
Line 62, Delete "2 mm" and insert -- 2 min --, therefore;

Column 35,
Line 30, Delete "254 run" and insert -- 254 nm --, therefore;

Column 36,
Line 61, Delete "10 mm" and insert --10 min --, therefore; and Delete "2 mm" and insert -- 2 min --, therefore;

UNITED STATES PATENT AND TRADEMARK OFFICE
CERTIFICATE OF CORRECTION

PATENT NO. : 6,825,350 B2  
APPLICATION NO. : 10/166321  
DATED : November 30, 2004  
INVENTOR(S) : Stephen L. Crooks Page 4 of 5

It is certified that error appears in the above-identified patent and that said Letters Patent is hereby corrected as shown below:

Column 40,  
Line 2, Delete "N-[2" and insert -- N-[4 --, therefore;  
Line 3, Delete "trifluoromethanesulfamide" and insert  
    -- trifluoromethanesulfonamide --, therefore;  
Line 33, Delete "4amine" and insert -- 4-amine --, therefore;  
Line 51, Delete "4-amino" and insert --4-amine--, therefore and Delete  
    "2 drain (7.4 ml)" and insert -- 2 dram (7.4 mL) --, therefore;  
Line 52, Delete "Diisopropylethylanilne" and insert  
    -- Diisopropylethylamine --, therefore;  
Line 61, Delete "10 mm" and insert -- 10 min --, therefore;

Column 50,  
Line 36, Delete "10 mm" and insert -- 10 min --, therefore;  
Line 37, Delete "2 mm" and insert -- 2 min --, therefore;

Column 127,  
Line 41, Delete "animonium" and insert -- ammonium --, therefore;

Column 135,  
Line 28, Delete "Trifluoroacetat" and insert -- Trifluoroacetate --, therefore;

Column 136,  
Line 37, Delete "10 mm" and insert -- 10 min --, therefore;  
Line 38, Delete "2 mm" and insert -- 2 min --, therefore;

Column 137,  
Line 20, Delete "20 ml/min" and insert -- 20 mL/min --, therefore;  
Line 21, Delete "10 mm" and insert --10 min --, therefore;  
Line 22, Delete "2 mm" and insert -- 2 min --, and Delete "B0.1" and insert  
    -- B=0.1--, therefore;

Column 138,  
Line 53, After "-78° C." delete "(2.0";  
Line 61, Delete "10 mm" and insert --10 min --, therefore;

Column 146,  
Line 7, Delete "-αα-" and insert -- -α,α- --, therefore;  
Line 24, Delete "he" and insert -- the --, therefore;  
Line 48, Delete "Compostion" and insert -- Composition --, therefore;  
Line 62, Delete "-αα-" and insert -- -α,α- --, therefore;

UNITED STATES PATENT AND TRADEMARK OFFICE
CERTIFICATE OF CORRECTION

PATENT NO. : 6,825,350 B2
APPLICATION NO. : 10/166321
DATED : November 30, 2004
INVENTOR(S) : Stephen L. Crooks It is certified that error appears in the above-identified patent and that said Letters Patent is hereby corrected as shown below:

Column 148,
Line 37, Delete "A-PD" and insert -- 4-PD --, therefore;
Line 38, Delete "sites" and insert -- site --, therefore.

Signed and Sealed this

Twelfth Day of June, 2007

JON W. DUDAS
*Director of the United States Patent and Trademark Office*